United States Patent
Criminisi et al.

(10) Patent No.: US 12,141,924 B1
(45) Date of Patent: Nov. 12, 2024

(54) COHORT BASED BODY CHANGE JOURNEYS

(71) Applicant: Amazon Technologies, Inc., Seattle, WA (US)

(72) Inventors: Antonio Criminisi, Cambridge (GB); Brandon Michael Smith, Fremont, CA (US); Ridge Carpenter, Seattle, WA (US); Durga Venkata Kiran Yakkala, Eluru (IN); Noam Sorek, Zichron Yaccov (IL)

(73) Assignee: Amazon Technologies, Inc., Seattle, WA (US)

( * ) Notice: Subject to any disclaimer, the term of this patent is extended or adjusted under 35 U.S.C. 154(b) by 116 days.

(21) Appl. No.: 17/935,453

(22) Filed: Sep. 26, 2022

(51) Int. Cl.
*G06T 19/00* (2011.01)
*A61B 5/00* (2006.01)
*G06T 7/60* (2017.01)
*G06T 17/00* (2006.01)
*G16H 50/50* (2018.01)

(52) U.S. Cl.
CPC ............ *G06T 19/00* (2013.01); *A61B 5/4872* (2013.01); *G06T 7/60* (2013.01); *G06T 17/00* (2013.01); *G16H 50/50* (2018.01); *G06T 2200/24* (2013.01); *G06T 2207/30196* (2013.01); *G06T 2219/012* (2013.01)

(58) Field of Classification Search
CPC .......... G06T 19/00; G06T 7/60; G06T 17/00; G06T 2200/24; G06T 2207/30196; G06T 2219/012; G06T 11/206; A61B 5/4872; G16H 50/50
See application file for complete search history.

(56) References Cited

U.S. PATENT DOCUMENTS

| | | | |
|---|---|---|---|
| 10,037,820 B2 | 7/2018 | Wong et al. | |
| 10,702,216 B2 | 7/2020 | Sareen et al. | |
| 11,069,131 B2 | 7/2021 | Agrawal et al. | |
| 2019/0051008 A1* | 2/2019 | Barker | G16H 50/70 |
| 2020/0293174 A1 | 9/2020 | Diaz et al. | |
| 2020/0294677 A1 | 9/2020 | Godinho et al. | |
| 2023/0024672 A1 | 1/2023 | Bonutti et al. | |

* cited by examiner

*Primary Examiner* — Jeffery A Brier
(74) *Attorney, Agent, or Firm* — Athorus, PLLC

(57) ABSTRACT

Described are systems and methods directed to a body change journey that utilizes one or more current body measurement values, one or more goal body measurement values, and a cohort to determine a body change journey that a user can follow to progress from the current body measurement value to the goal body measurement value. The cohort may include a plurality of data of other bodies who have progressed from a starting body measurement value that is similar to the current body measurement value.

20 Claims, 32 Drawing Sheets

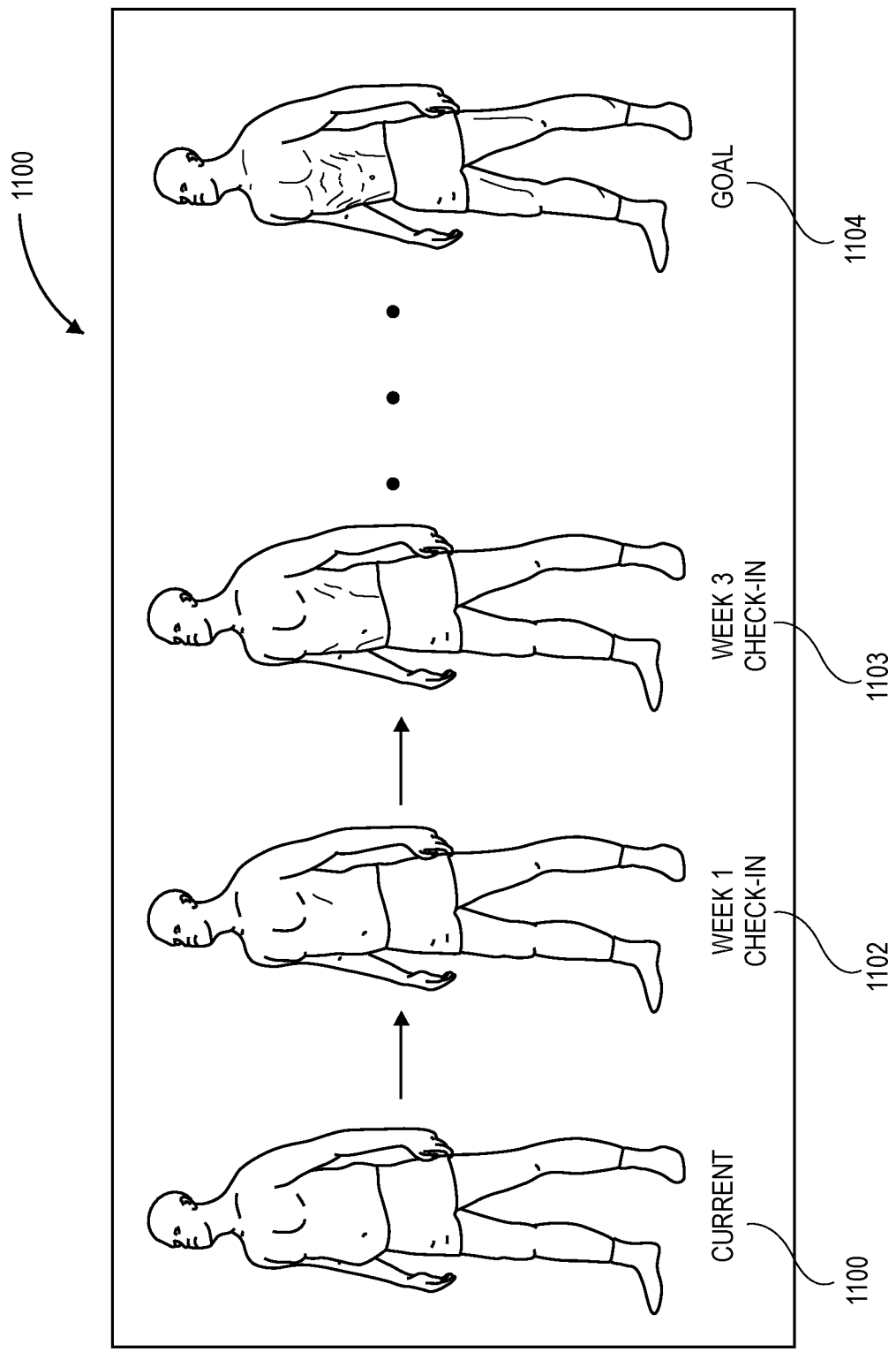

COHORT BASED BODY CHANGE JOURNEYS

BACKGROUND

Three-dimensional modeling of the human body currently requires large or expensive sensors, such as stereo imaging elements, three-dimensional scanners, depth sensing devices, etc. Likewise, many fitness applications require high friction of a user taking body measurements, entering data into the application, coordinating with health experts, etc. In addition, exercise programs do not consider or factor in body characteristics of the user.

BRIEF DESCRIPTION OF THE DRAWINGS

FIG. 11 is a block diagram illustrating predicted personalized 3D body models for a determined body change journey, in accordance with implementations of the present disclosure.

DETAILED DESCRIPTION

Figure 1:
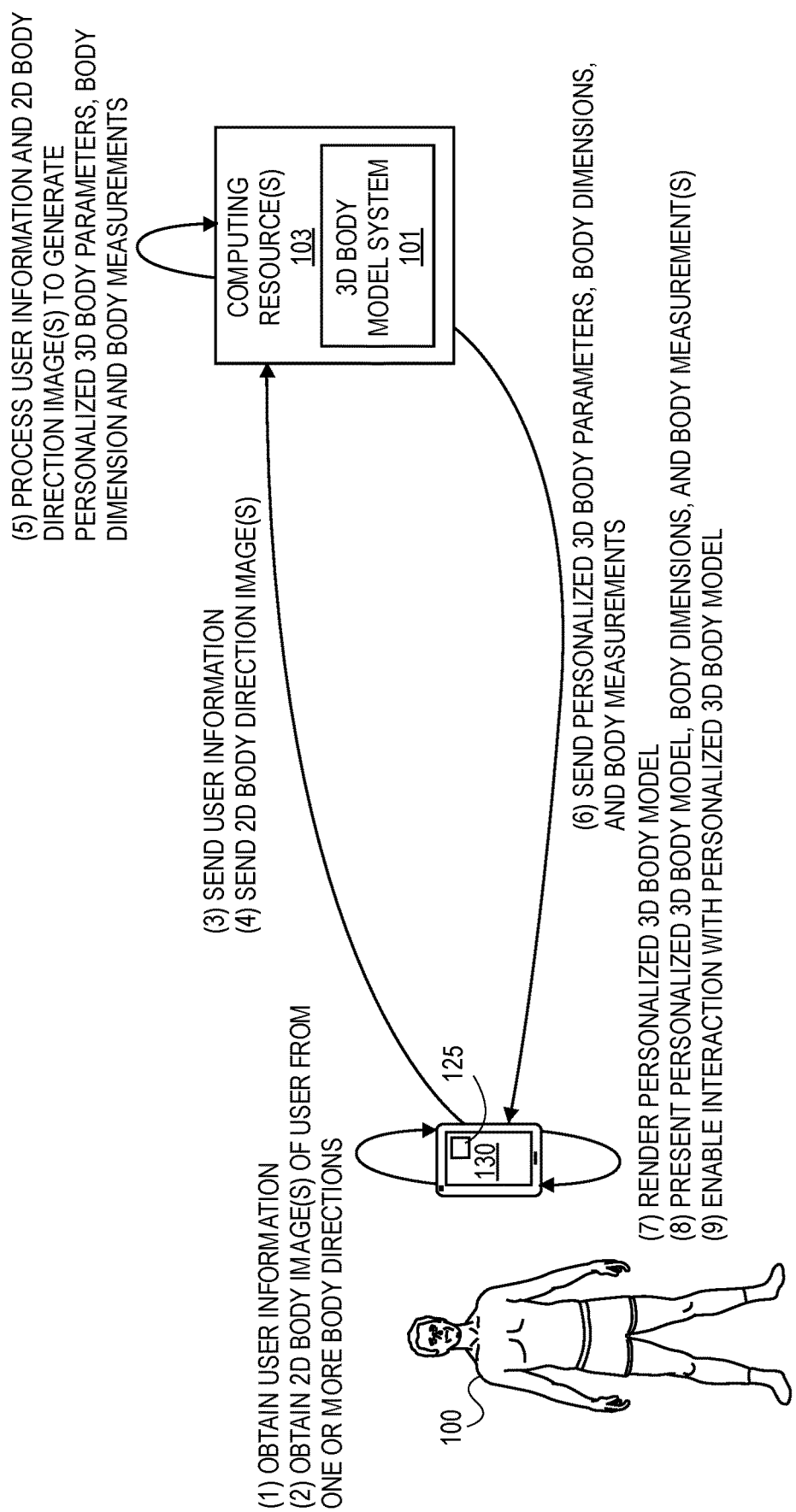
FIG. 1 is an example transition diagram of two-dimensional body image collection and processing to produce body dimensions, in accordance with implementations of the present disclosure.

As is set forth in greater detail below, implementations of the present disclosure are directed to a body change journey that utilizes collected two-dimensional ("2D") body images of a body of a user, generation and presentation of a personalized three-dimensional ("3D") body model of the body of the user based on those 2D body images, the generation and presentation of different predicted personalized 3D body models of the body of the user at different body measurements (e.g., different body fat percentages, different muscle mass amounts, different body weights, etc.), and the generation of a body change journey that guides the user from their current body composition to a selected goal body composition that may be represented by a goal personalized 3D body model of the body of the user.

Two-dimensional body images may be obtained from any device that includes a 2D camera, such as cell phones, tablets, laptops, etc. In other implementations, the 2D body images may be obtained from any other source, such as data storage. The 2D body images may be sent by an application executing on the device to remote computing resources that process the 2D body images to determine personalized 3D body features, to generate a personalized 3D body model of the body of the user, to determine body dimensions of the body represented in the 2D image, and/or to determine body measurements of the body of the user. Body measurements include, but are not limited to, body composition (e.g., weight, body fat, bone mass, body mass, body volume, etc.).

The application executing on the portable device receives the current body dimension information, current body measurement information, and personalized 3D body features, generates the personalized 3D body model, and presents some or all of the body dimensions, some or all of the body measurements, and/or the personalized 3D body model to the user. In some implementations, the user may interact with the personalized 3D body model to view different sides of the personalized 3D body model and/or to visualize differences in the personalized 3D body model and/or corresponding body dimensions if one or more body measurements change. For example, a user may provide a goal body measurement, such as a change in body fat, a change in weight, a change in lean body mass, a change in muscle mass, a change in fat free mass, a change in a waist-to-hip ratio, a change in body mass index, etc., and the disclosed implementations may generate one or more predicted personalized 3D body models and corresponding predicted body dimensions that represent a predicted appearance and predicted dimensions of the body of the user with the goal body measurement(s). In some implementations, the predicted appearance and/or predicted dimensions of the body may be presented as a 3D body slider and/or other adjustor that the user may interact with to view progressive changes to the body appearance and dimensions at different body measurements.

Still further, the disclosed implementations, using the current body measurements of the user and user selected predicted body measurements, referred to herein as goal body measurements, may generate a body change journey that the user can follow that helps guide the user from their current body composition to their specified goal body composition. Alternatively, rather than providing a goal body measurement, the user may provide a body change journey duration and a body measurement of interest. In such an example, the disclosed implementations may determine a predicted body measurement value for the body measurement of interest based on the duration of the body change journey specified by the user.

Regardless of whether the body change journey is generated based on a goal body measurement or a body change journey duration, periodic check-ins with visual updates of the predicted and actual changes in body measurements may be provided to encourage the user, adjust the body change journey if necessary, and to keep the user motivated toward a selected goal.

In still further implementations, the body change journey presented by the user may include median trends, average trends, trends or ranges above or below the average/median trends, etc., thereby indicating to the user how different interventions (e.g., change in activity, sleep, stress, food/alcohol consumption, etc.) can alter the expected trajectory of the user along the body change journey.

Body dimensions, as used herein, include any length, circumference, ratio, etc., of any part of a body. For example, body dimensions include, but are not limited to, shoulder circumference, chest circumference, waist circumference, hip circumference, inseam length, bicep circumference, leg circumference, waist to hip ratio, chest to waist ratio, waist to height ratio, etc. Body measurements include, but are not limited to, weight, body fat, bone mass, muscle mass, lean tissue, body mass, body volume, arm circumference, waist width, shoulder width, torso width, torso circumference, etc. Body parameters include, but are not limited to, shape vector of the body, pose, body height, arm length, leg length, torso length, etc. Body composition, as used herein, includes body measurements, body dimensions, and/or and body parameters.

Figure 2A:
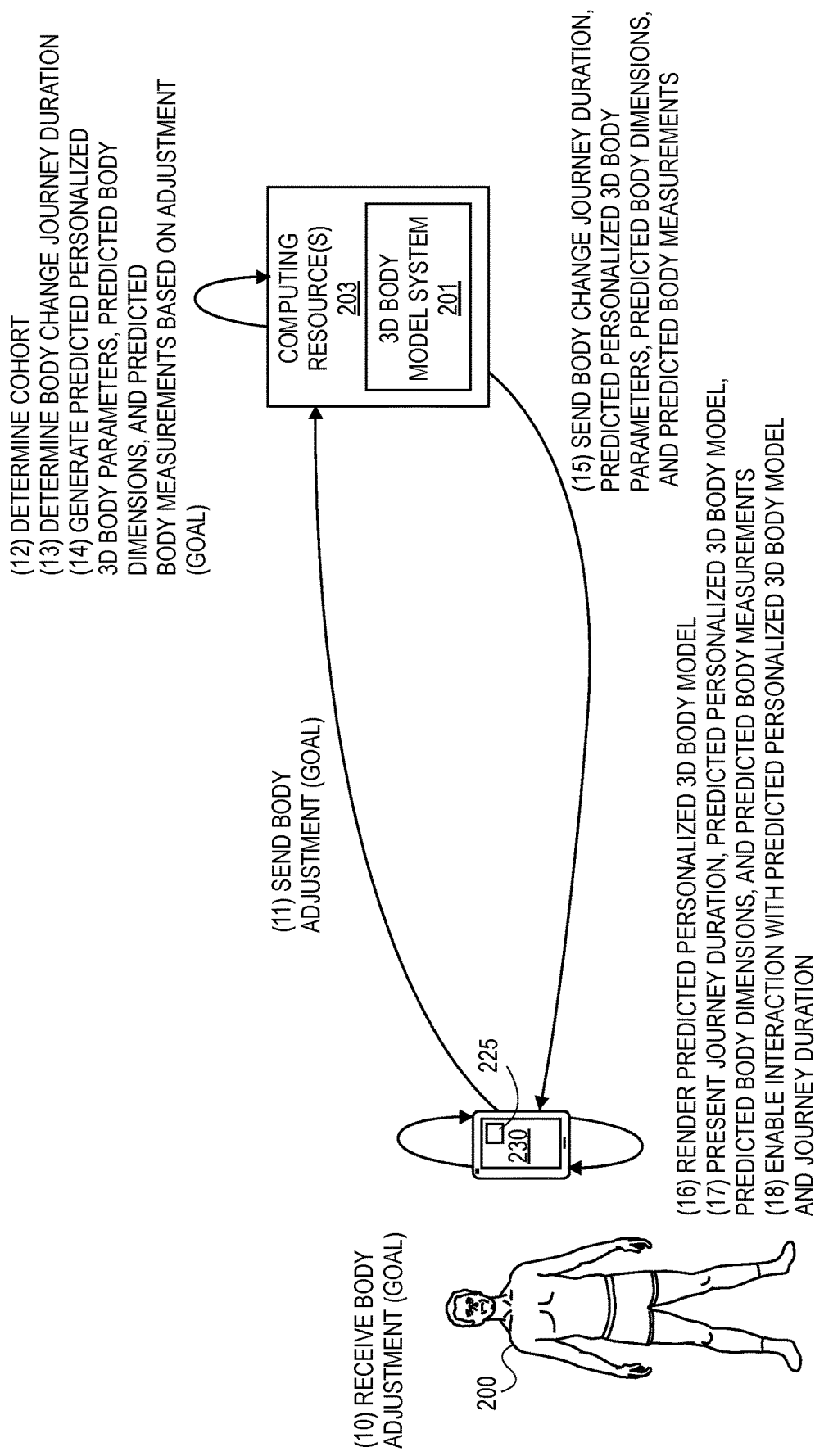
FIGS. 2A and 2B are example transition diagrams of generating a body change journey for a user, in accordance with implementations of the present disclosure.
Figure 2B:
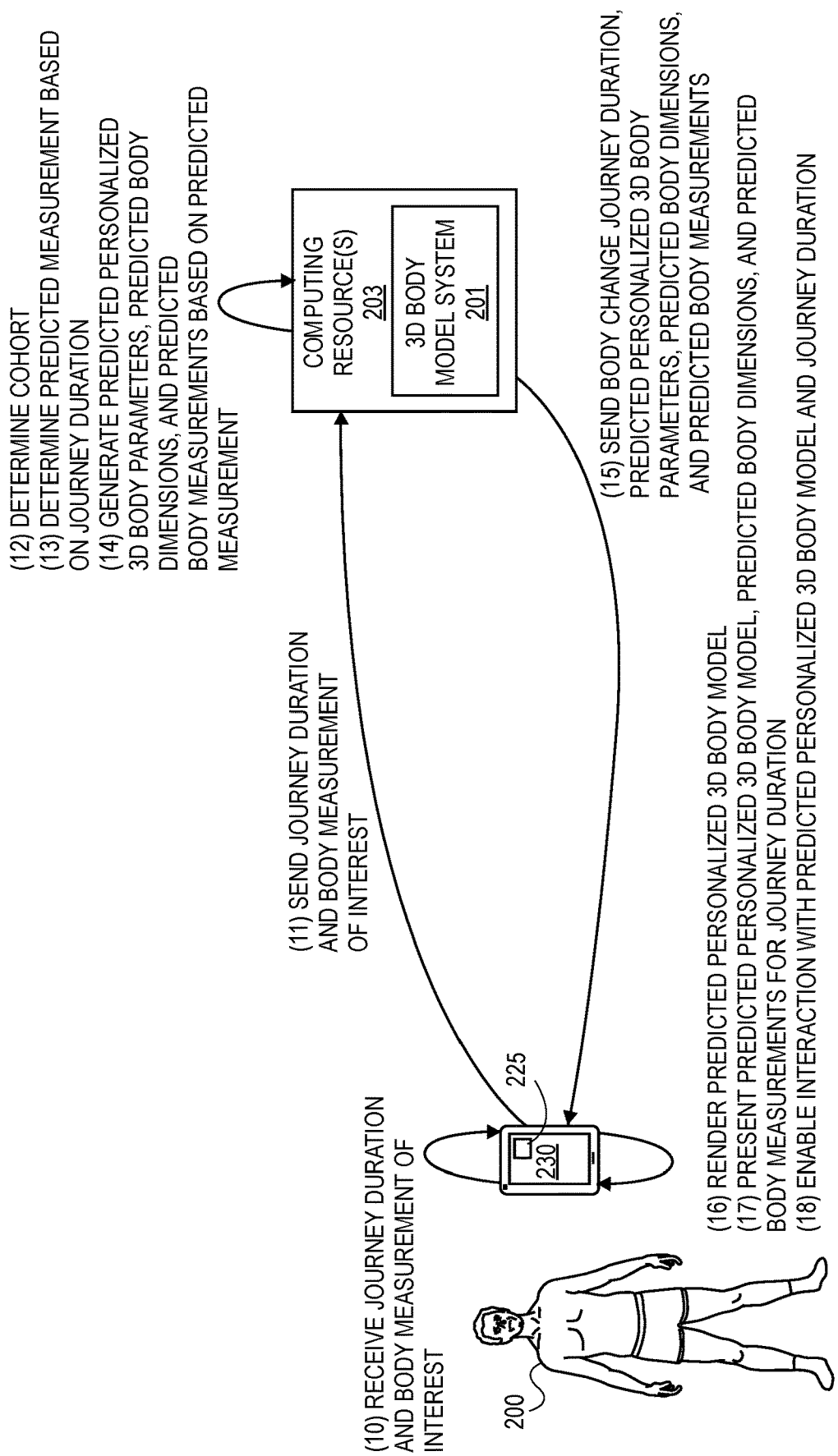
Figure 3:
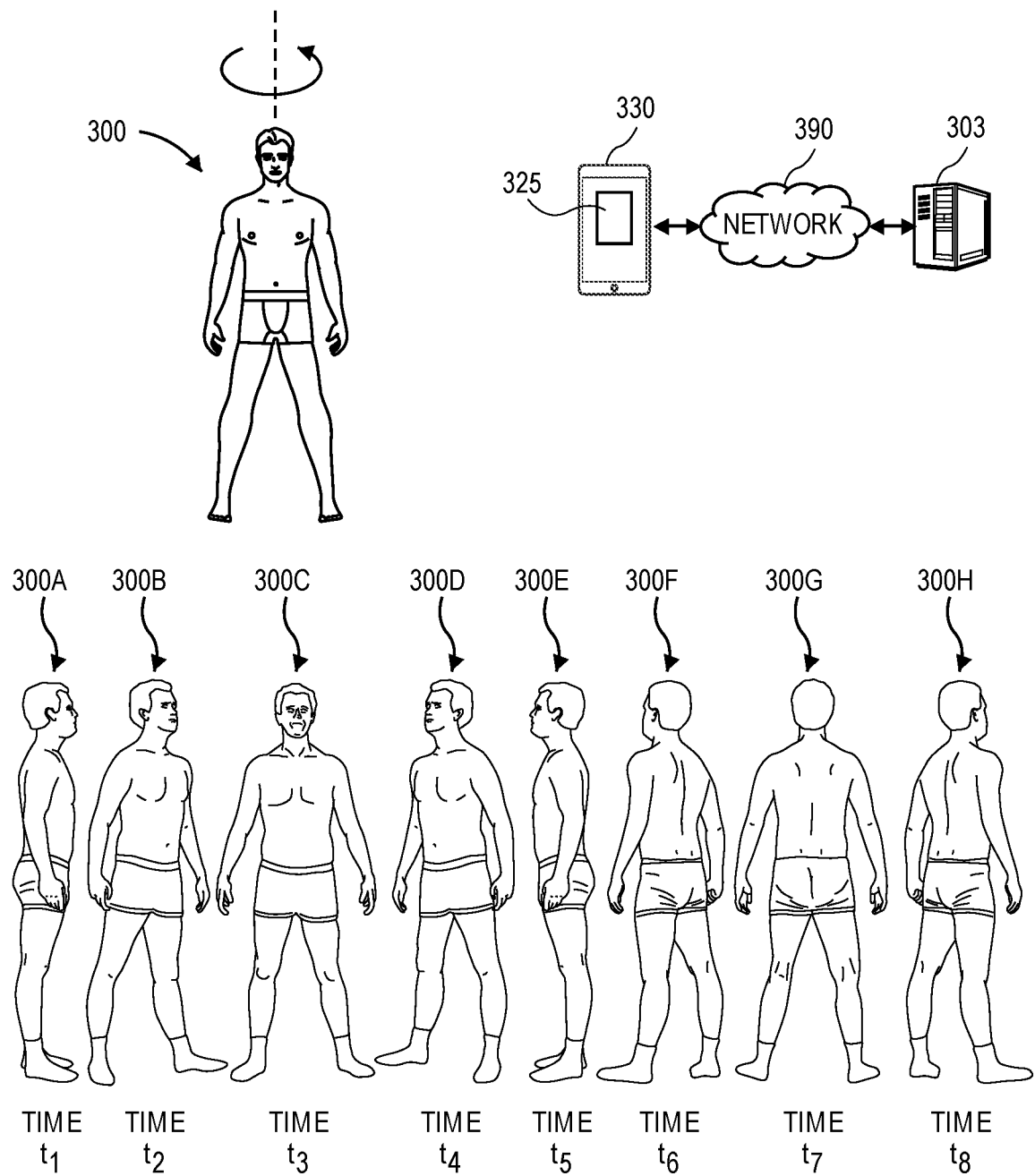
FIG. 3 illustrates different body directions of a body that may be captured in two-dimensional body images and used to produce body dimensions and/or a personalized three-dimensional body model, in accordance with implementations of the present disclosure.

FIG. 1 is a transition diagram of 2D body image collection and processing to produce a personalized 3D body model of a body of a user 100 and/or body dimensions of the body of the user that may be presented back to the user, FIGS. 2A and 2B are transition diagrams of a generation of a body change journey and corresponding predicted 3D body model and predicted body dimensions, in accordance with disclosed implementations. FIG. 3 illustrates examples of different orientations or body directions of a body 300, in accordance with implementations of the present disclosure.

In some implementations, a user 100/200/300 may execute an application 125/225/325 on a portable device 130/230/330, such as a cellular phone, tablet, laptop, etc., that includes an imaging element (e.g., camera) and interact with the application. The imaging element may be any conventional imaging element, such as a standard 2D Red, Green, Blue ("RGB") digital camera that is included on many current portable devices. Likewise, images, as discussed herein may be still images generated by the imaging element and/or images or frames extracted from video generated by the imaging element.

The user 100/200/300 may provide user information, such as username, password, etc., to the application 125/225/325 so that the application can identify the user and determine a user account associated with the user. Likewise, the user 100/200/300 may provide other user information, such as body information, including but not limited to weight, height, age, gender, ethnicity, etc. The user 100/200/300 may select which user information is provided or choose not to provide any user information. In addition, in some implementations, the user 100/200/300 may interact with the application 125/225/325 executing on the portable device 130/230/330 without providing any user identifying information (e.g., operate as a guest to the application).

Upon user identification and/or receipt of user information, the user 100/200/300 positions the portable device 130/230/330 such that a field of view of the imaging element of the portable device is substantially horizontal and facing toward the user. In some implementations, the application 125/225/325 executing on the portable device 130/230/330 may provide visual and/or audible instructions that guide the user 100/200/300 in the placement and positioning of the portable device 130/230/330. For example, the application may instruct the user 100/200/300 to place the portable device 130/230/330 between waist and head height of the user and in a substantially vertical direction (e.g., between 2 and 10 degrees of vertical) such that the imaging element is pointed toward the user and the field of view of the imaging element is substantially horizontal.

In some implementations, the application 125/225/325 may request that the user 100/200/300 wear a minimal amount of clothing, such as undergarments as shown in FIGS. 1, 2A, 2B, and 3. By wearing minimal clothing, processing of the 2D body image may be more accurate.

Once the portable device is properly positioned, 2D body images of the user 100/200/300 are captured by the imaging element of the portable device 130/230/330. The 2D body images are processed to determine that the user is in a defined pose, such as an "A Pose," and to determine a body direction of the body of the user with respect to the imaging element. The defined pose may be any body position that enables image capture of components of the body. In one example, the defined pose is an "A Pose" in which the arms are separated from the sides of the body and the legs are separated, for example by separating the feet of the body to about shoulder width. The A Pose allows image processing of 2D body images to distinguish between body parts (e.g., legs, arms, torso) from different angles and also aids in body direction determination. The body direction may be any direction or orientation of the body with respect to the imaging element. Example body directions include, but are not limited to, a front side body direction in which the body is facing the imaging element, a right side body direction in which the body is turned such that a right side of the body is facing the imaging element, a left side body direction in which a left side of the body is facing the imaging element, and a back side body direction in which a back of the body is facing the imaging element. As will be appreciated, any number of body directions and corresponding orientations of the body may be utilized with the disclosed implementations and the four discussed (front side, right side, back side, and left side) are provided only as examples.

In some implementations, the application 125/225/325 executing on the portable device 130/230/330 may guide the user 100/200/300 through different body directions and select one or more 2D images as representative of each body direction. For example, referring to FIG. 3, an application 325 executing on the portable device 330 may guide the user into the proper pose, such as the "A Pose" illustrated by the body 300 of the user and then guide the user through a series of body directions 300A, 300B, 300C, 300D, 300E, 300F, 300G, and 300H in which the users rotates their body to the requested body direction and remains in the "A Pose" while 2D body images are generated and one or more of those 2D body images are selected by the application 325 as a 2D body direction image corresponding to the current body direction of the body of the user. In the example illustrated in FIG. 3, eight different 2D body direction images are selected by the application 325 executing on the portable device 330, one for each respective body direction 300A, 300B, 300C, 300D, 300E, 300F, 300G, and 300H.

Returning back to FIG. 1, as each 2D body direction image is selected by the application, or after all 2D body direction images are selected, the 2D body direction images are sent from the application 125/225/325 executing on the portable device 130/230/330 via a network 390 (FIG. 3) to remote computing resources 103/203/303 for further processing. In addition, the user information provided to the application 125/225/325 by the user 100/200/300 may be sent from the application executing on the portable device 130/230/330 to the remote computing resources 103/203/303. In other implementations, all processing may be done on the portable device 130/230/330. In still other examples, as images are generated, the images may be sent to the remote computing resources 103/203/303 and processed by the remote computing resources 103/203/303 to select the body direction images.

The remote computing resources 103/203/303 may include a 3D body model system 101 that receives the user information and/or the 2D body direction images and processes those images using one or more neural networks, such as a convolutional neural network, to generate personalized 3D body features corresponding to a personalized 3D body model of the body of the user 100/200/300. In addition, one or more of the 2D body direction images, such as front side 2D body direction image may be processed to determine one or more additional body measurements, such as body fat percentage, body mass, bone density, muscle mass, etc. Still further, one or more of the 2D body direction images may be processed, as discussed further below, to determine one or more body dimensions of the user 100/200/300, such as shoulder circumference, waist circumference, waist-to-hip ratio, etc.

The 3D body model system 101, upon generating the personalized 3D body features, body dimensions and body measurement sends the personalized 3D body features, body dimensions, and body measurements back to the application 125/225/325 executing on the portable device 130/230/330. The application 125/225/325, upon receipt of the personalized 3D body features, body dimensions, and body measurements generates, from the personalized 3D body features, a personalized 3D body model that is representative of the body 100/200/300 of the user and presents the personalized 3D body model, one or more body dimensions, and one or more body measurements on a display of the portable device 130/230/330.

In addition to rendering and presenting the personalized 3D body model, one or more body dimensions, and/or one or more body measurements may be presented. In some implementations, the user 100/200/300 can interact with the presented personalized 3D body model, body dimensions, and body measurements. For example, the user 100/200/300 may view historical information that was previously collected for the user via the application 125/225/325. The user 100/200/300 may also interact with the presented personalized 3D body model to rotate and/or turn the presented personalized 3D body model. For example, if the portable device 130/230/330 includes a touch-based display, the user 100/200/300 may use the touch-based display to interact with the application 125/225/325 and rotate the presented personalized 3D body model to view different views (e.g., front, side, back) of the personalized 3D body model.

Likewise, in some implementations, the user may view body dimension information with respect to a larger population or cohort to which the user is associated (e.g., based on age, fitness level, height, weight, gender, etc.). For example, the user may view body dimension information relative to body dimension information of other people that are within five years of age of the user and of a same gender as the user.

In some implementations, as part of interaction with the application 125/225/325, the user 100/200/300 may provide one or more adjustments to body measurements, referred to herein as goals. For example, a user 100/200/300 may request to alter the body fat measurement value of the body by a defined amount (e.g., from 25% to 20%), alter the muscle mass by a defined amount, alter the body weight a defined amount, etc. In other implementations, in addition to altering one or more body measurements, the user 100/200/300 may specify one or more activities (e.g., exercise, nutrition, sleep) that should cause adjustments to one or more body measurements. In still other examples, the user may specify a time duration during which they are going to engage in one or more activities (e.g., exercise, diet) that should cause adjustments to one or more body measurements.

In the example illustrated in FIG. 2A, the user 100/200/300 provides a body fat measurement adjustment to a goal body fat measurement value. Alternatively, or in addition thereto, the user 100/200/300 may specify a time duration for which adjustments are to be considered. For example, the user 100/200/300 may specify that they are interested in a ninety-day body change journey and the system may indicate an expected change or trend in one or more body measurements that the user should expect during that period of time, as well as ranges above and/or below the expected change/trend.

Upon receipt of the goal body fat measurement value, the application 125/225/325 executing on the portable device 130/230/330 sends the goal body fat measurement value to the remote computing resources 103/203/303 for further processing. The remote computing resources 103/203/303 and the 3D body model system 101/201 may determine, based on the current body parameters determined for the body of the user 100/200/300 and/or other information about the user, a cohort indicative of other users that have or had similar body measurements. As discussed further below, a cohort may include a plurality of data for other bodies that are similar to the body of the user 100/200/300, some or all of which may also have historical data that may be utilized to determine a body change journey for the user. For example, data for bodies included in the cohort may have a starting body composition that is similar to a current body composition of the user 100/200/300 and a final body composition that is similar to a goal body composition of the user, above the goal body composition of the user, or below the goal body composition of the user. Such information may be combined, as discussed herein, to determine a trend line, such as a median trend line illustrating predicted changes in one or more body measurement values during the duration of the body change journey, and/or for predicting ranges above and/or below the trend line.

Based on the determined cohort and the received goal body fat measurement value, the remote computing resources 103/203/303 may determine a body change journey having a duration of time that is achievable for the user 100/200/300 to reach the goal body fat measurement. In addition, the remote computing resources 103/203/303 may process the received goal body fat measurement value along with other current body measurements and the personalized 3D body features to generate predicted personalized 3D body features, predicted body dimensions, and predicted body measurements that correspond to the goal body fat measurement value and/or the selected activity.

The remote computing resources 103/203/303 may then send the body change journey, predicted personalized 3D body features, predicted body dimensions, and predicted body measurements to the application 125/225/325 and the application 125/225/325 may render a predicted 3D body model based on the received predicted personalized 3D body features. Similar to the personalized 3D body model, the application 125/225/325 may present the predicted 3D body model, one or more predicted body dimensions, one or more of the predicted body measurements, and/or information regarding the body change journey that the user 100/200/300 can follow to achieve the specified goal to the user and enable interaction by the user with the predicted personalized 3D body model, predicted body dimensions, predicted body measurements, and/or body change journey.

As discussed further below, in some implementations, the user 100/200/300 may be able to alter views between the personalized 3D body model and the predicted personalized 3D body model. In other implementations, the application 125/225/325 may integrate the personalized 3D body model and the predicted personalized 3D body model to produce a 3D body slider and/or other adjustor (e.g., radio button, dial, etc.) that provides the user with a continuous view of different appearances of the body and/or different body dimensions of the body at different body measurements between the current body measurements and the predicted body measurements. The 3D body slider and/or other adjustor, which relates to any type of controller or adjustor that may be used to present different appearances of the body and/or different body dimensions of the body at different body measurements is referred to herein generally as a "3D body model adjustor."

As changes are made to the 3D body model, the body change journey may be updated to reflect those changes and continue to present an achievable body change journey for the user 100/200/300, based on information determined from the cohort with which the body of the user is associated. Alternatively, if the user 100/200/300 makes changes to the body change journey, such as extends or shortens the duration, increases or decreases the activity level of the user, etc., the 3D body model and/or 3D body measurements may also be updated to illustrate the predicted changes to the body of the user during the body change journey.

As an alternative to providing a goal body measurement and receiving a body change journey, in other implementations, a user 100/200/300 may specify a time duration for the body change journey and receive an indication of the body measurements that the body of the user should expect during the time duration. For example, and referring to FIG. 2B, the user 100/200/300 may provide a body change journey duration and a body measurement of interest and/or one or more activities that will be followed by the user during the duration.

Upon receipt of the body change journey duration, the application 125/225/325 executing on the portable device 130/230/330 sends the duration and any other information, such as body measurement of interest or activities, to the remote computing resources 103/203/303 for further processing. The remote computing resources 103/203/303 and the 3D body model system 101/201 may determine, based on the current body parameters determined for the body of the user 100/200/300 and/or other information about the user, a cohort indicative of other users that have similar body measurements. Likewise, based on the determined cohort and the received body change journey duration, the remote computing resources 103/203/303 may predict one or more body measurement values that may change during the duration of the body change journey. In addition, the remote computing resources 103/203/303 may process the predicted body measurement values along with other current body measurements and the personalized 3D body features to generate predicted personalized 3D body features, predicted body dimensions, and the predicted body measurements that may result during the duration of the body change journey.

The remote computing resources 103/203/303 may then send the body change journey, predicted personalized 3D body features, predicted body dimensions, and predicted body measurements to the application 125/225/325 and the application 125/225/325 may render a predicted 3D body model based on the received predicted personalized 3D body features. Similar to the personalized 3D body model, the application 125/225/325 may present the predicted 3D body model, one or more predicted body dimensions, one or more of the predicted body measurements, and/or information regarding the body change journey that the user can follow during the specified duration of the journey.

Figure 4A:
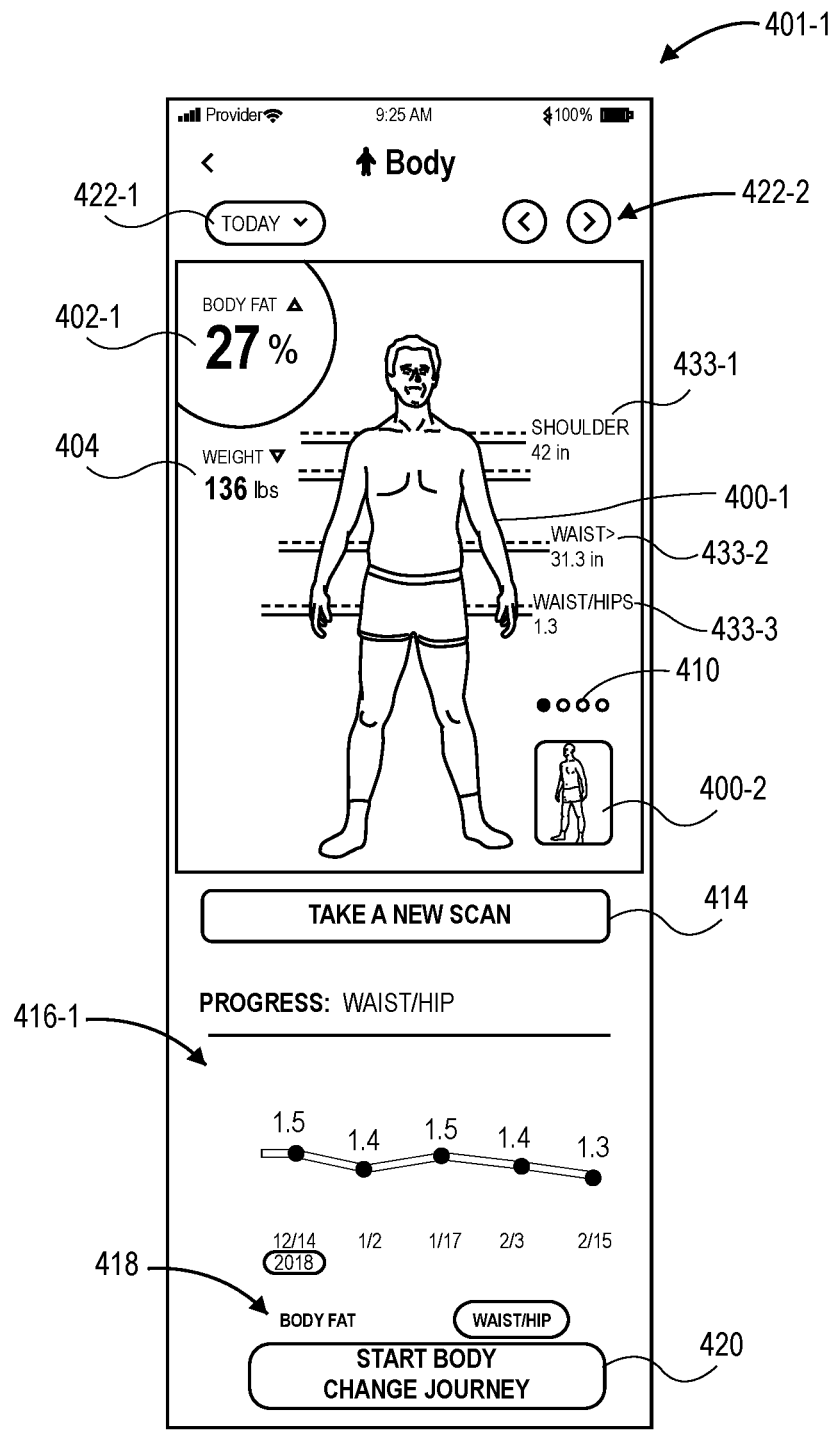
FIG. 4A is a user interface illustrating a captured two-dimensional body image, corresponding body dimensions, and body measurements determined from at least the two-dimensional body image, in accordance with implementations of the present disclosure.

FIG. 4A is a user interface 401-1 presented by an application executing on a portable device, such as the application 125/225/325 executing on the portable device 130/230/330 discussed above with respect to FIGS. 1, 2A, 2B, and 3 in accordance with implementations of the present disclosure.

In this example, the user interface 401-1 illustrates a 2D body direction image 400-1 captured by an imaging element of the portable device 130/230/330 that was used to generate and present a personalized 3D body model, corresponding body dimension information and corresponding body measurement information. In this example, the illustrated user interface 401-1 shows the 2D body direction image, body dimensions, including the shoulder circumference 433-1, waist circumference 433-2, and waist/hip ratio 433-3, and body measurements, including the body fat percentage 402-1 determined for the body, and the weight 404 of the body. As will be appreciated, additional or less body dimensions and/or body measurements may be included on the user interface 401-1. For example, additional body dimensions, such as bicep circumference, waist to height ratio, thigh circumference, etc., may optionally be presented on the user interface. In some examples, a user may select which body dimensions and/or body measurements are presented.

Figure 4B:
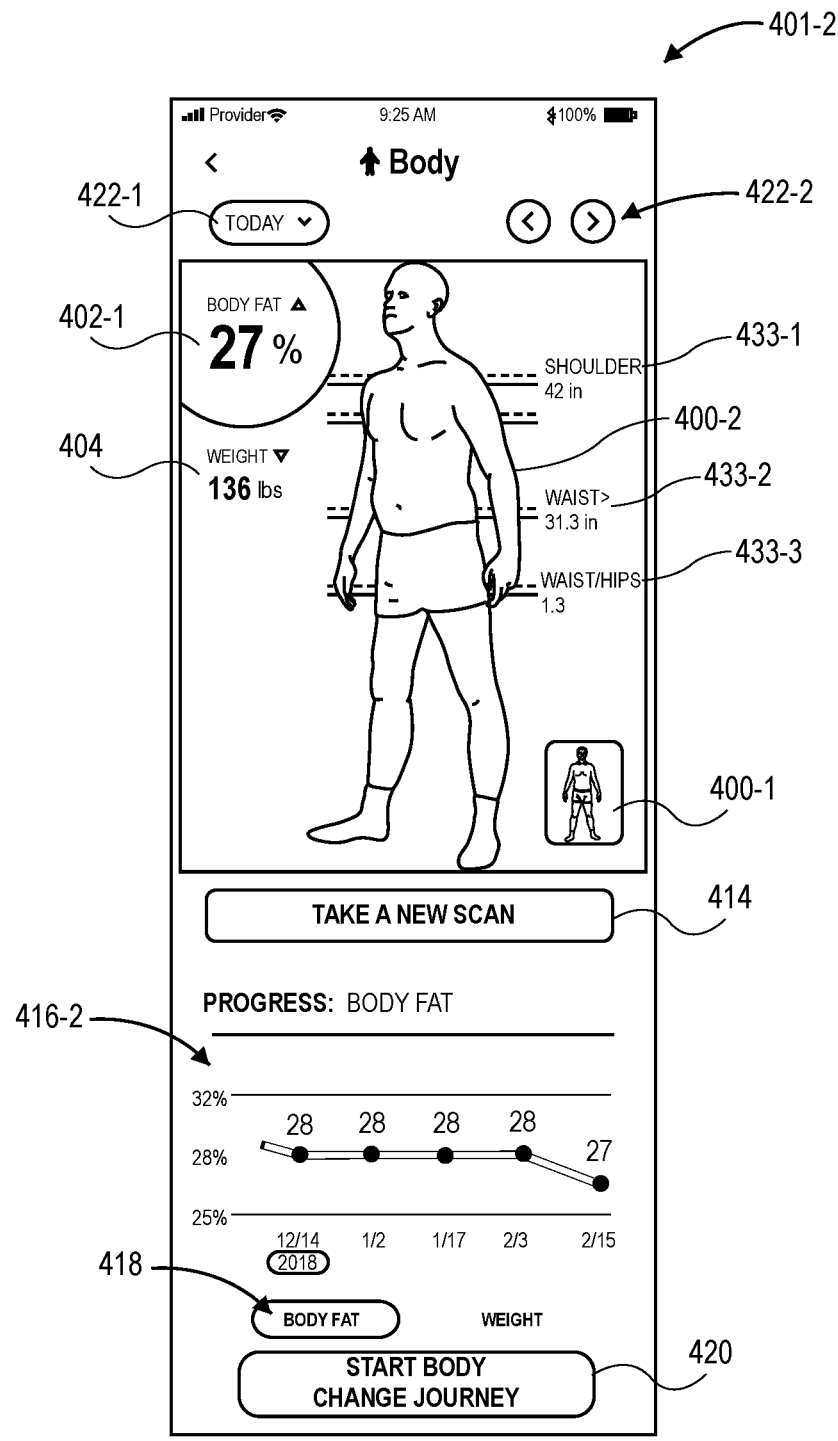
FIG. 4B is a user interface illustrating a personalized three-dimensional body model, body dimensions, and corresponding body measurements generated from a two-dimensional body image, in accordance with implementations of the present disclosure.

As discussed further below, the body dimensions may be determined from the 2D body direction image 400-1. Likewise, the body measurements may be determined from the 2D body direction image 400-1 and/or provided as user information by the user 100/200/300. In other implementations, additional or fewer body dimensions and/or additional or fewer body measurements may be presented on the user interface 401-1 by the application 125/225/325. A user interacting with the user interface 401-1 may also select to view other 2D body direction images that were used to generate a personalized 3D body model, other body dimensions determined for the body, and/or other body measurements determined for the body, by selecting the indicators 410 and/or swiping or otherwise interacting with the user interface 401-1 to alter the currently presented 2D body direction image 400-1. The user 100/200/300 may also alternate between a view of 2D body direction images 400-1, as illustrated in the user interface 401-1 of FIG. 4A and the rendered and presented personalized 3D body model 400-2, as illustrated in the small image presentation of the personalized 3D body model 400-2 in FIG. 4A and as illustrated as the primary image 400-2 in user interface 401-2 of FIG. 4B. Referring briefly to FIG. 4B, the user may rotate and/or change the view of the personalized 3D body model 400-2 by directly interacting with the personalized 3D body model 400-2. For example, the user may rotate the presentation of the personalized 3D body model to view different portions of the personalized 3D body model, zoom out to view more of the personalized 3D body model, or zoom in to view details corresponding to a portion of the personalized 3D body model.

In some implementations, if the user 100/200/300 has utilized the application 125/225/325 over a period of time to generate multiple instances of personalized 3D body models of the user, the user interface may also present historical body measurements and/or body dimensions 416 corresponding to the different dates in which 2D body images of the body of the user were captured and used to generate a personalized 3D body model, body dimensions, and body measurements of the body of the user. In the illustrated example, the user may select between viewing historical waist/hip ratio 416-1 (a body dimension) as illustrated in FIG. 4A and body fat percentage 416-2 (a body measurement), as illustrated in FIG. 4B, through selection of the toggle control 418. In other implementations, different or additional historical body dimensions and/or body measurements may be accessible through the user interface 401.

In addition to viewing historical body dimensions and/or body measurements, the user may also access and view either the 2D body images that were collected at those prior points in time and/or view the personalized 3D body models generated from those prior 2D body images, through selection of the date control 422-1 or the arrow control 422-2.

The user 100/200/300 may also interact with the user interface 401-1 to select to take a new scan of their body by selecting the Take A New Scan control 414. In response to a user selecting the Take A New Scan control 414, the application 125/225/325 executing on the portable device 130/230/330 will provide instructions to the user 100/200/300 to position the user in the defined pose (e.g., "A Pose") and at proper body directions so that 2D body direction images can be generated and used to produce a personalized 3D body model, body dimensions, and body measurements of the body of the user, as discussed herein.

In some implementations, a user 100/200/300 may also interact with the application 125/225/325 to predict an appearance of the body with different body measurements (e.g., changes in body fat percentage and/or changes in muscle mass).

Figure 4C:
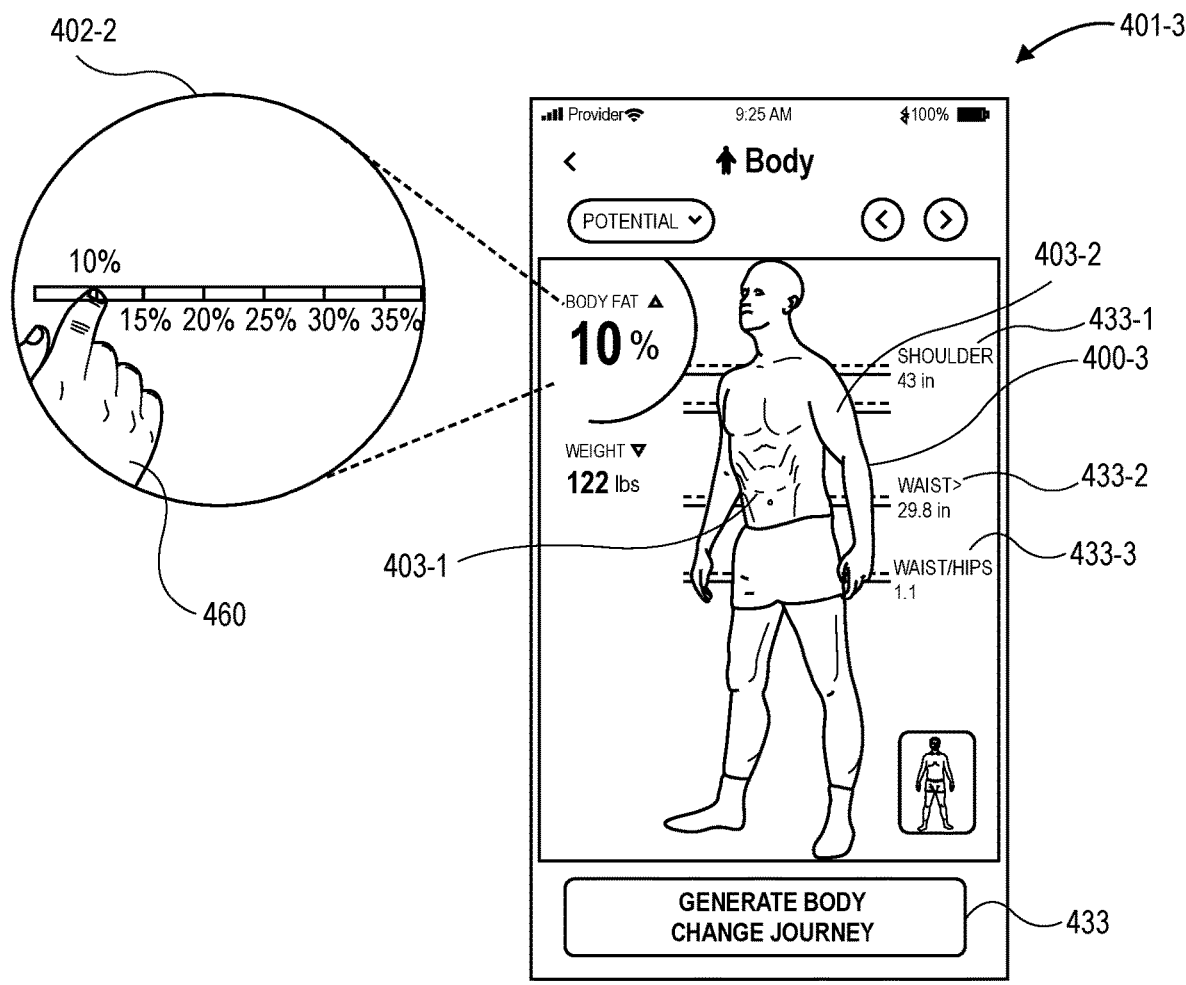
FIG. 4C is a user interface illustrating an example 3D body model adjustor in the form of a slider adjustment and resulting predicted personalized three-dimensional body model, corresponding predicted body dimensions, and corresponding predicted body measurements, in accordance with implementations of the present disclosure.

For example, FIG. 4C is a user interface illustrating an example 3D body model adjustor in the form of a slider adjustment and resulting predicted three-dimensional body model, corresponding body dimensions, and corresponding body measurements, in accordance with implementations of the present disclosure. As illustrated, a user may interact with the user interface 401-3 to alter one or more body measurements and the application executing on the device will generate a predicted personalized 3D body model 400-3, predicted body dimensions, and predicted body measurements in accordance with the altered body measurements, in accordance with implementations of the present disclosure. In the illustrated example, the user is using their hand 460 to interact with a single slider 402-2 presented on the user interface 401-3 to alter the body fat measurement value, in this example from the computed 27% to 10%.

In response to receiving the goal body measurement, in this example the reduced body fat measurement value, the disclosed implementations, as discussed further below, generate and present a predicted personalized 3D body model 400-3, predicted body dimensions, and predicted body measurements representative of a predicted appearance of the body of the user with the goal body measurement. The predicted personalized 3D body model 400-3 may be predicted and rendered based on the personalized 3D body model and corresponding personalized 3D body features determined for the body of the user. Likewise, shading and contours, such as shading to show stomach muscle definition 403-1 or body dimension changes, such as increased bicep circumference 403-2, increased shoulder circumference 433-1, decreased waist circumference 433-2, increased waist/hip ratio 433-3, etc., may be generated and presented with the presentation of the predicted personalized 3D body model.

The predicted body dimensions may be determined from the predicted personalized 3D body model and/or from the trained machine learning model. For example, the predicted personalized 3D body model may be used to generate a predicted personalized silhouette that may be used, as discussed herein, to generate predicted body dimensions. Alternatively, based on the goal body measurement, a synthetic body model may be selected or generated, and a silhouette generated by the synthetic body model that corresponds to the goal body measurements. The silhouette may then be used, as discussed herein, to determine predicted body dimensions corresponding to the goal body measurement.

Like the other rendered and presented personalized 3D body models, the user may interact with the presented predicted personalized 3D body model 400-3 to view different portions or aspects of the predicted personalized 3D body model.

While the example illustrated in FIG. 4C shows alteration of the body fat percentage, in other examples, a user may select to alter other body measurements, such as body weight, muscle mass, etc., and/or alter the current body model of the user to generate a predicted personalized 3D body model of the user. Likewise, in some examples, based on a change to one body measurement, other body measurements and/or body dimensions may be automatically changed to correspond to the changed body measurement. For example, if the user changes the body fat percentage from 27% to 10%, as in the illustrated example, the application executing on the portable device may determine that in most instances a change in that amount of body fat percentage also typically results in a weight change from the determined 136 pounds to 115 pounds. The user may accept this anticipated change to other body measurements and/or body dimensions, provide other inputs for those body measurements and/or body dimensions, or select to leave those body measurements/body dimensions unchanged.

In still other examples, a user may be able to interact with a multi-dimensional slider and specify different changes to body measurements and/or activities. In some implementations, some or all of the sliders of the multi-dimensional slider may be interconnected such that a change to one slider may results in a change or adjustment to another slider. In other implementations, other forms of multi-dimensional 3D body model adjustors may also be presented.

Figure 4D:
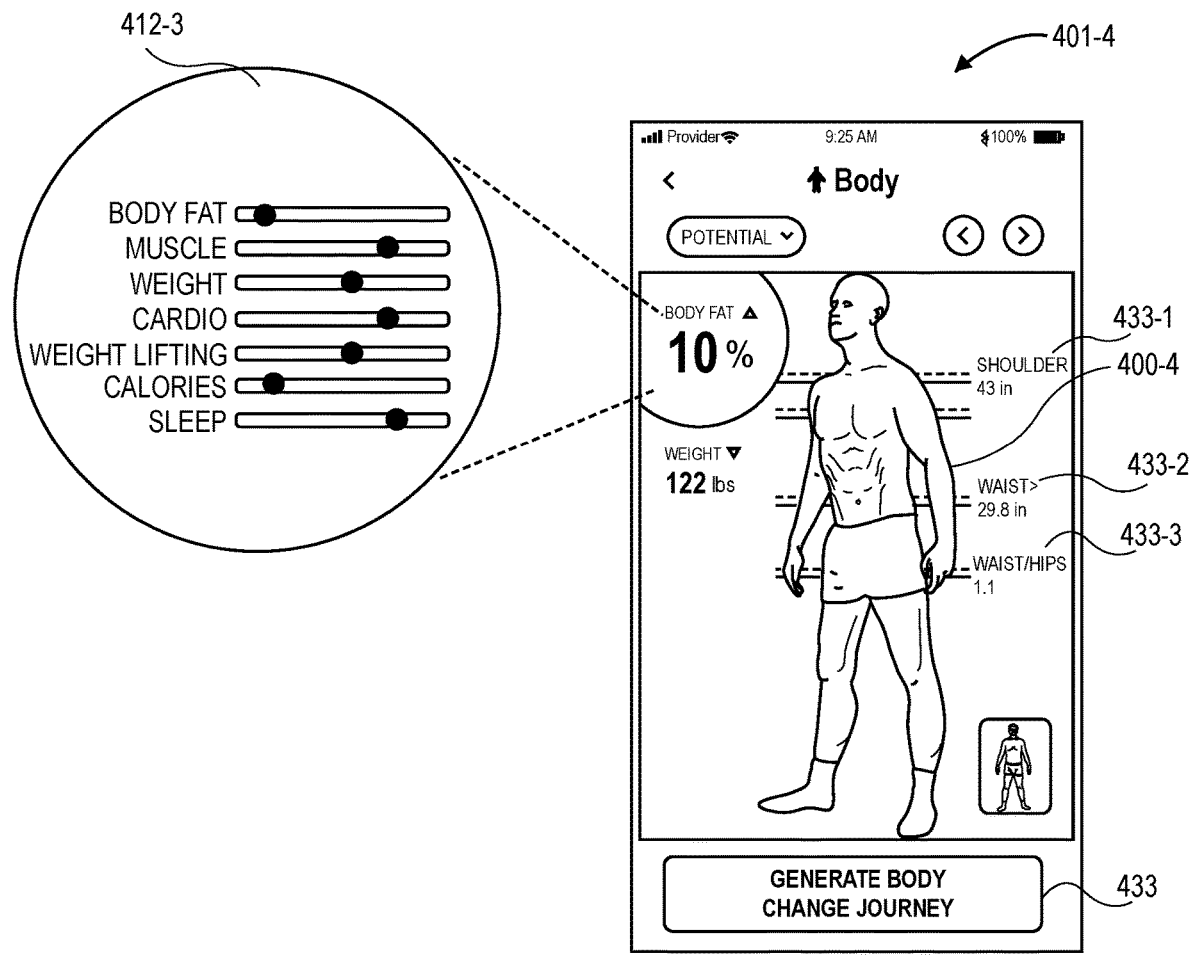
FIG. 4D is a user interface illustrating another example 3D body model adjustor in the form of a multi-dimensional slider adjustment and resulting predicted personalized three-dimensional body model, corresponding predicted body dimensions, and corresponding predicted body measurements, in accordance with implementations of the present disclosure.

FIG. 4D is a user interface 401-4 illustrating another example 3D body model adjustor in the form of a multi-dimensional slider 412-3 adjustment and resulting predicted personalized 3D body model 400-4 and predicted body dimensions 433-1, 433-2, 433-3, in accordance with implementations of the present disclosure. In this example, the user may interact with a multi-dimensional slider 412-3 to adjust one or more body measurements and/or activity levels. In this example, the user may adjust the body fat measurement value, muscle mass measurement of the body, weight of the body, the amount of time they do cardio exercises, lift weights, the number of calories consumed, and/or the number of hours the user sleeps. In other implementations, the sliders may represent other body measurements (e.g., muscle mass, weight, etc.) and/or other activities that may be changed by the user and utilized by the disclosed implementations as goals for use in computing predicted personalized 3D body features and corresponding predicted personalized 3D body models.

Once a predicted personalized 3D body model has been generated that the user desires to progress towards from the current body measurements, the user may select the Generate Body Change Journey control 433 and the application and/or 3D body model system stores the predicted personalized body measurements and predicted personalized body parameters corresponding to the selected predicted personalized 3D body model as goal body measurements and goal body parameters (collectively referred to herein as goal body composition) and generates a body change journey for the user that guides the body of the user through exercise activities, nutrition, sleep, etc., that will aid the body of the user in progression from the current body composition to the goal body composition. As discussed herein, the body change journey may be developed based on historical data from the cohort to which the body of the user is associated. For example, a trend based on cohort data may be determined and used as the mean or median trend line for the user during the body change journey. Likewise, upper ranges and lower ranges above and below the trend line, respectively, may also be determined and presented to the user to illustrate the impact different activities may have on the progress of the body of the user toward a goal. Utilizing cohort data aids in the development of a body change journey that is beneficial to the user and provides a higher likelihood of success for the user. In some implementations, predicted personalized check-in 3D body models may also be generated at check-in points or intervals illustrating the predicted body measurements and predicted body parameters of the body of the user at those points along the body change journey. The user may utilize these check-ins to compare the user's actual progress and body measurements/parameters at those check-ins with the predicted measurements/parameters to determine if the body of the user is ahead of progress, on track with the journey, or behind on the journey. Likewise, the 3D body model system may also use data determined from each check-in to determine if the body change journey for the user needs to be updated, to provide encouragement to the user, and/or to update one or more machine learning models and/or cohorts, as discussed further below.

Figure 4E:
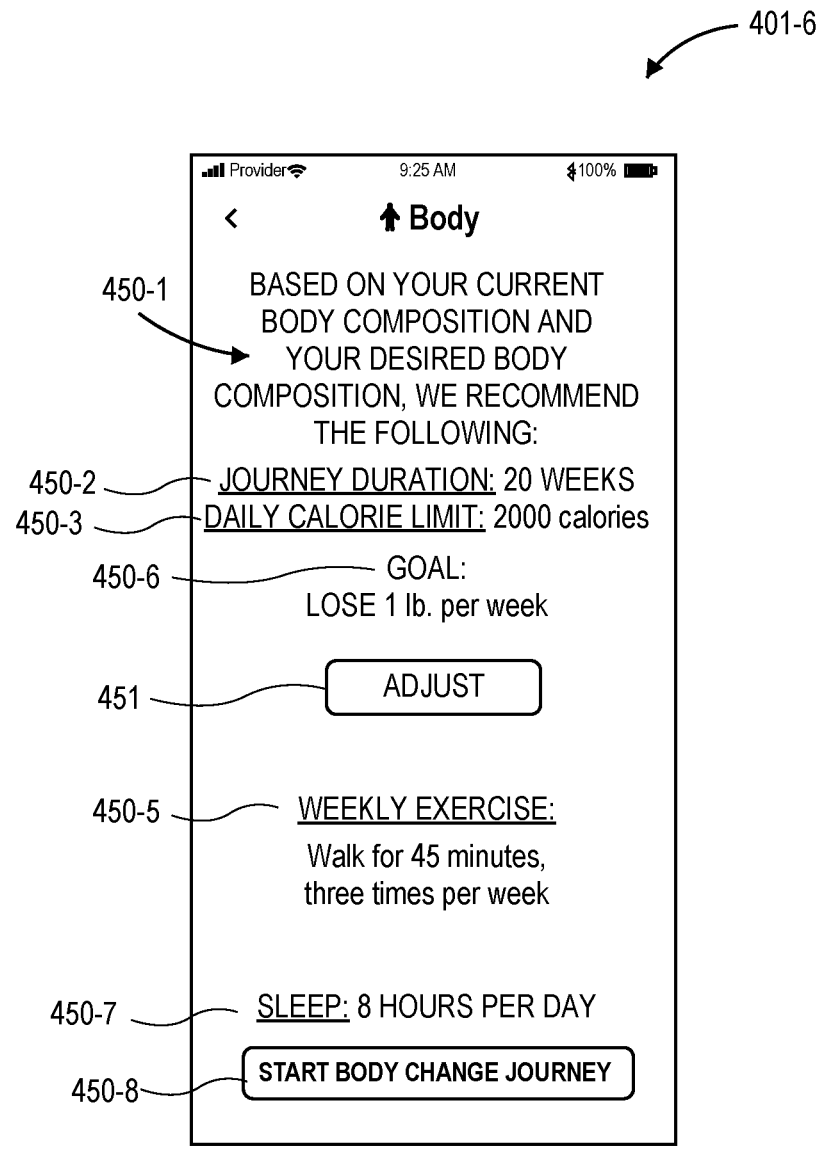
FIG. 4E is a user interface illustrating an overview of a generated body change journey, in accordance with implementations of the present disclosure.

FIG. 4E is a user interface 401-6 illustrating an overview of a generated body change journey 450-1, in accordance with implementations of the present disclosure.

As illustrated in FIG. 4E, upon selection of a goal body model by the user, selected goal body measurement(s), or a selected body change journey duration, the application and/or 3D body model system generates a body change journey 450-1 that illustrates, for example, a journey duration 450-2, daily calorie limit 450-3, weekly personalized exercise plans 450-5, goal 450-6, recommended sleep 450-7, etc. As discussed further below; the journey duration, daily calorie limit, personalized exercise plans, etc., may be determined based on information known about the user utilizing one or more rules engines and/or machine learning algorithms, such as a trained CNN, and the cohort to which the body of the user is associated. For example, the disclosed implementations may associate the user with a particular cohort of users based on age, demographics, exercise level, current body composition, known health issues, current activity level, etc., and determine, from the cohort, a healthy journey that, if followed, will progress the user from the current body composition to the goal body composition. For example, a median trend line from the current body composition to a goal body composition may be determined from a cohort based on the collective of data included in the cohort. Likewise, ranges above and/or below the median trend line from the cohort data may also be determined and presented to the user.

In some implementations, the output may further be personalized based on information known about the user. For example, if the user has provided food preferences, whether the user prefers prepared meals, restaurants, delivery, home cooked meals, etc., a personalized food plan or personalized meals may be developed and recommended to the user as part of the journey. As another example, if the user has specified exercise preferences, for example, whether the user prefers lifting weights in a commercial gym, swimming, running, aerobics, etc., a personalized exercise plan may be developed and recommended to the user as part of the body change journey. For example, a cohort may be defined based on the user provided preferences and user information and a body change journey developed based on information determined from the cohort.

As the user reviews the generated body change journey, the user can select to adjust various aspects of the body change journey. For example, the user may select the adjust control 451 to adjust one or more of the higher level aspects of the body change journey. Higher level aspects of the body change journey may include, for example, the daily calorie limit 450-3, journey duration 450-2, and/or the weekly exercise plan 450-5. In other implementations, the user may select other higher level aspects and/or other aspects of a presented body change journey. If a user adjusts one or more aspects of the journey, the disclosed implementations may re-evaluate the body change journey, and optionally define a new cohort, to consider the requested adjustment. For example, if the user selects to decrease the daily calorie limit, the disclosed implementations may re-evaluate the journey and determine, for example, that the duration may decrease and/or that the weekly exercise plan may change. Based on the re-evaluation, an updated body change journey may be presented to the user for further adjustment or selection. Alternatively, upper and lower ranges around a trend line of the expected body change journey may be highlighted or presented as indicative of the change(s) selected by the user.

Once the user has reviewed, optionally adjusted, and selected aspects of the body change journey, the user may start the body change journey through selection of the Start Body Change Journey control 450-8.

In some implementations, the user interface 401-6 may also present an intensity level or likelihood of success for a presented body change journey. For example, based on the user information and/or cohort, the likelihood that the user will complete the presented body change journey may be determined and presented to the user. In addition, the intensity or difficulty of the journey, as perceived by the user, may be presented to the user to illustrate to the user the difficulty of the body change journey. Presentation of such information may be beneficial to provide motivation to a user that the user is selecting a body change journey that is properly adapted to the user and for which the user has a high likelihood of success and/or to discourage a user from selecting a body change journey that is too difficult for the user or for which the user has a low likelihood of success.

As one example, if a new user that has not exercised for years is considering a body change journey, presentation that the body change journey has an intensity level directed toward beginners and that the user has a high probably of successfully completing the body change journey, as determined by the user's assigned cohort, the user may be more likely to select and participate in the body change journey. In comparison, if the user adjusts the journey and, upon re-evaluation, that the intensity level of the journey is high and that the likelihood of success for the user is low, such information may discourage the user from selecting the adjusted body change journey.

Figure 4F:
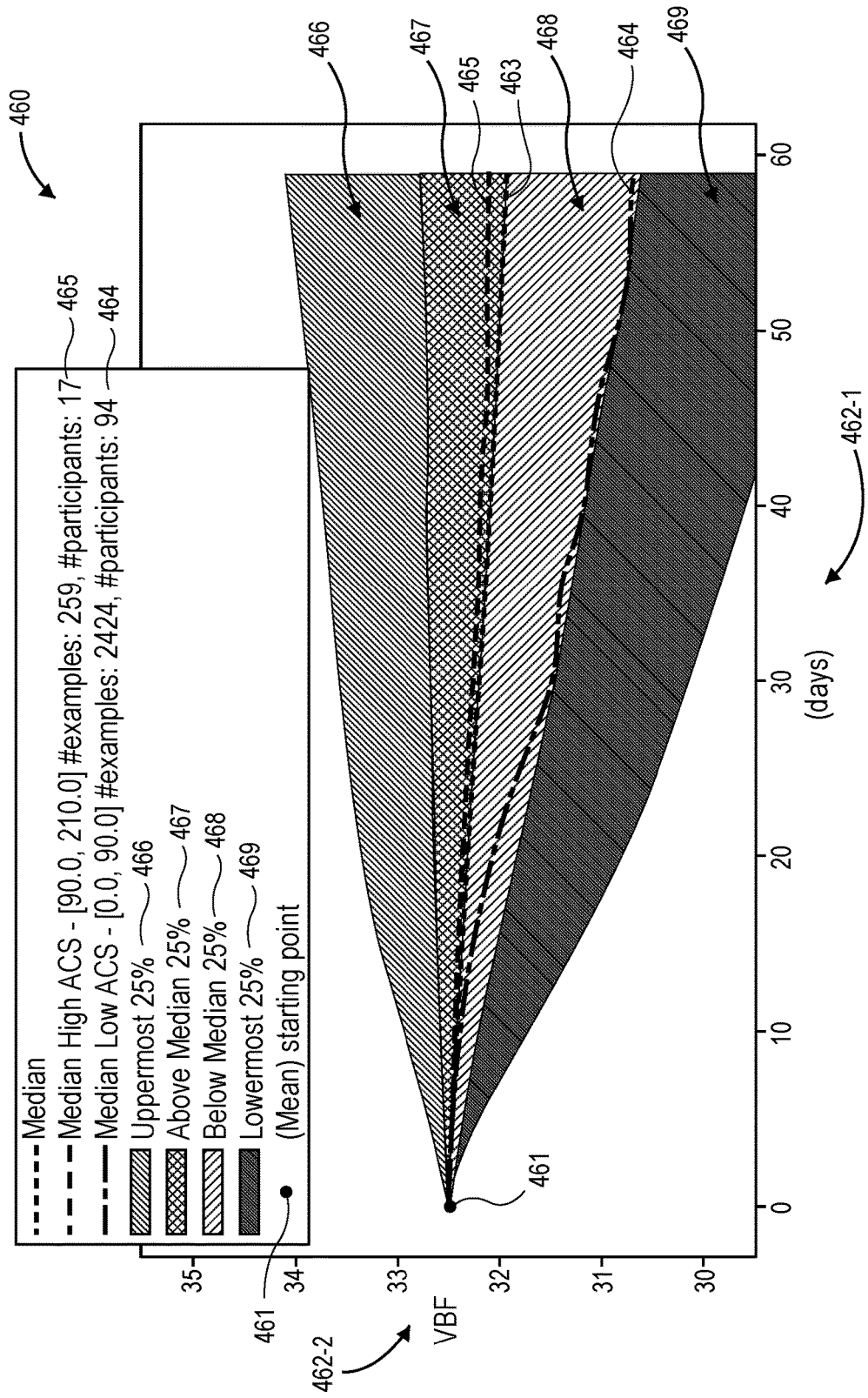
FIG. 4F is a user interface illustrating example trends for a generated body change journey, in accordance with implementations of the present disclosure.

FIG. 4F is a user interface 460 illustrating example trends for generated body change journeys, in accordance with implementations of the present disclosure.

As illustrated, the median trend line 463 for visual body fat 462-2 changes during the duration 462-1 of the body change journey for which the user is most likely to follow as it is a median of the results of the cohort defined for the body of the user over the defined duration of the body change journey. As discussed below, the median trend line 463, the high trend line 465 or median high activity composite score ("ACS"), the low trend line 464 or median low ACS, the uppermost twenty-five percent body fat range 466, the twenty-five percent above median body fat range 467, the twenty-five percent below median body fat range 468, and the lowest twenty-five percent median body fat range 469 may be determined based on the members of the cohort. In some implementations, the illustration 460 may also show the total number of members of the cohort from which the data was generated and optionally the number of cohort members in each range.

The cohort ranges illustrated in FIG. 4F may be generated independent of the body of the user and based on the members of the cohort. For example, the median trend line 463 is determined from the cohort and is representative of the median of cohort member data during a defined duration of time that corresponds to the duration of the body change journey. Likewise, the upper ranges and lower ranges are determined based on member data trends above or below the median trend line.

The cohort data, trend lines, and ranges, when applied to a specific user that is associated with the cohort, may be shifted up or down to correspond to the starting point 461 of the body of the user, thereby providing user specific body change journey guidance and expectations. Likewise, while the example 460 illustrates the body change of visual body fat 462-2 over a period of time 462-1, in other implementations, other body measurement trend lines and ranges may be determined from the cohort data and presented as an example graph over a duration of time.

Figure 4G:
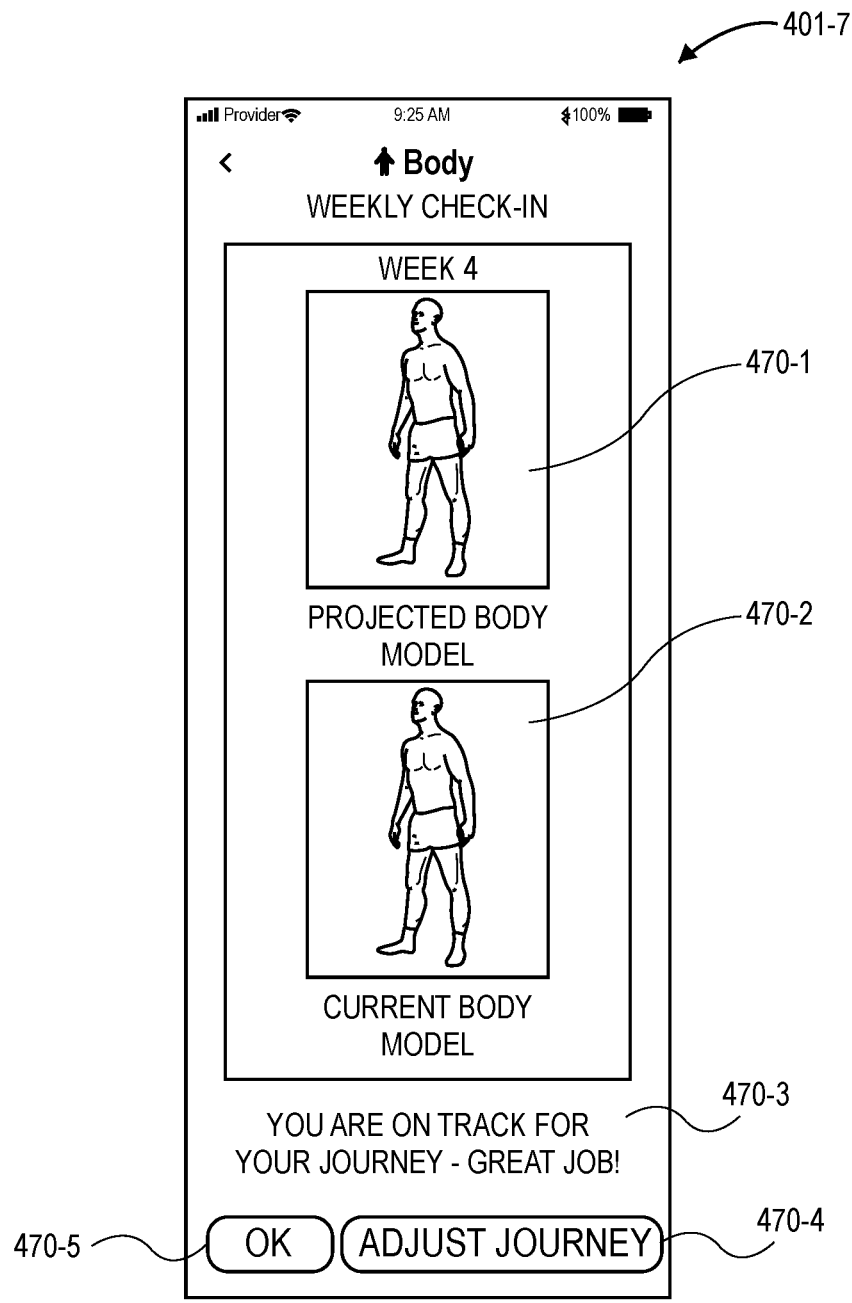
FIG. 4G is a user interface illustrating a weekly check-in as part of a body change journey, in accordance with implementations of the present disclosure.

FIG. 4G is a user interface 401-7 illustrating a weekly check-in as part of a body change journey, in accordance with implementations of the present disclosure.

As discussed, a body change journey may include periodic check-ins so that the user can compare their actual body progress with a projected progress for their body at each check-in, determine if they are ahead, on-track, or falling behind on the progress of the journey, adjust one or more aspects of the body change journey, etc. For example, similar to providing the initial 2D body images, a user, at each periodic check-in, such as a weekly check-in, may provide 2D body images of the body of the user and the 3D body model system may process the images to determine current actual body composition and a current actual 3D body model 470-2 of the user at that point in time. In addition, as discussed further below, a predicted personalized check-in 3D body model 470-1 and predicted personalized body composition at that point in time for the user may also be determined based on the body change journey.

The current actual body composition and the predicted personalized body composition at the check-in may be compared to determine if the user is ahead, on-track, or behind in the body change journey. Likewise, the visual comparison, as illustrated in FIG. 4G, provides a visual illustration to the user to visually verify their progress along the journey. In the illustrated example, the current personalized 3D body model 470-2 is very similar to the predicted personalized check-in 3D body model at the check-in and the comparison of the current actual body composition and the predicted body composition for the check-in also confirm that the user is on track at this point in the body change journey, as confirmed with a statement such as "You Are On Track For Your Journey—Great Job!" 470-3.

In some implementations, the user may also compare the determined current actual body composition values and/or the predicted check-in body composition values, the differences therebetween, etc., as part of a check-in. Likewise, a user may select to adjust one or more aspects of the body change journey through selection of the Adjust Journey control 470-4 or complete the check-in, through selection of the OK control 470-5.

Figure 4H:
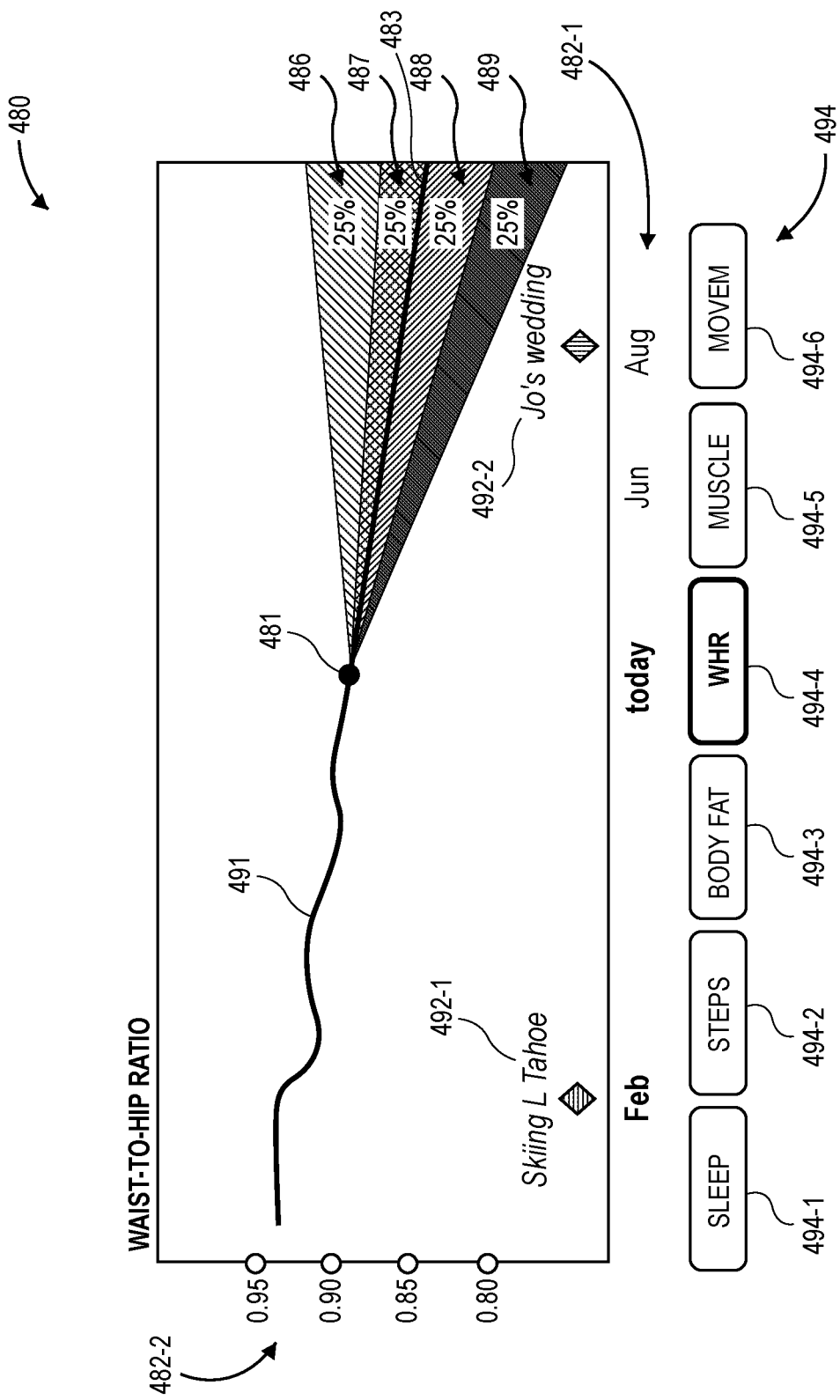
FIG. 4H is a user interface illustrating an example historical path and future trends for a generated body change journey, in accordance with implementations of the present disclosure.

Still further and referring to FIG. 4H, a user may view their actual progress 491 since the beginning of the body change journey up to the current check-in 481, along with the median trend line 483 and corresponding upper and lower ranges 486, 487, 488, 489 generated for the user for that check-in day 481 forward, based at least in part on the cohort associated with the user. In some implementations, at each check-in, the actual body measurements may be utilized along with progress of members of the cohort to generate the median trend line 483 and median ranges 486, 487, 488, 489 going forward so that adjustments to the body change journey are updated at each check-in and the user receives a realistic progression through the body change journey based on actual data and information determined from the cohort with which the body of the user is associated.

In the example illustrated with respect to FIG. 4H, the user is viewing a graph 480 of a waist-to-hip ratio 482-2 over time 482-1 of the body change journey. In some implementations, the user may select to view changes in, for example, sleep 494-1, steps 494-2, body fat 494-3, waist-to-hip ratio 494-4, muscle mass 494-5, movement 494-6, and/or other activities 494, or measurements. Likewise, the user may indicate points in time that are of interest to the user, such as "Skiing L Tahoe" 492-1, which is indicated as a date in the past but during the body change journey, or "Jo's Wedding" 492-2, indicated as a date in the future.

The periodic check-ins as part of a body change journey provide an improvement over existing systems that require daily and manual tracking of food, exercise, sleep, etc., by eliminating the need for the daily inputs. Instead, the periodic check-ins provide a simplified process that visually compares and verifies the user's progress along the body change journey with predicted progress that is specific to that user and/or updates forward expectations as appropriate.

Figure 5:
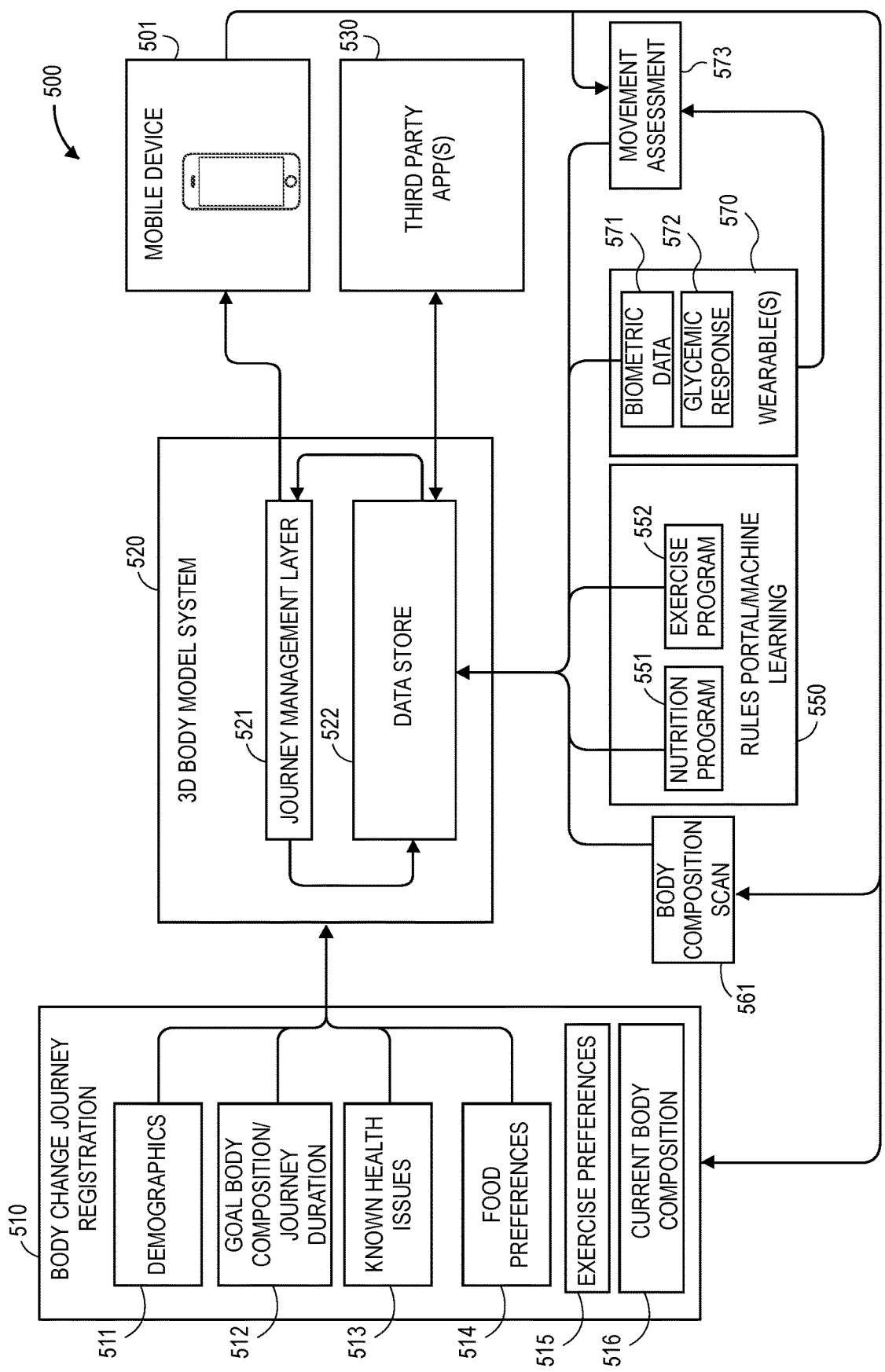
FIG. 5 is a block diagram of a system architecture, in accordance with implementations of the present disclosure.

FIG. 5 is a block diagram of a system architecture 500, in accordance with implementations of the present disclosure.

As illustrated, a user may register with the body journey management layer 521 of the 3D body model system 520 to begin a body change journey through the body change journey registration 510, which may be accessed through an application executing on a mobile device 501 accessible to a user. As part of the registration process, the user may create a user account and provide one or more of demographics 511 information (gender, age, weight, etc.), goal body composition or body change journey duration 512, known health issues 513, food preferences 514, exercise preferences 515, current body composition 516, etc.

As discussed above, current body composition 516 may be determined based on 2D images of the body of the user that are processed by the 3D body model system 520 to determine the current body composition (body measurements, body parameters) of the body of the user. Alternatively, or in addition thereto, the user may provide other body composition data, such as weight, height, blood pressure, heart rate, etc. In still other examples, current body composition values may be obtained from one or more wearables 570, worn by the user that are connected to and exchange data with the body change journey management layer 521 of the 3D body model system 520. For example, wearables 570 may provide biometric data 571 (e.g., heart-rate, blood pressure, temperature, oxygen level, etc.), glycemic response 572, etc. In still other examples, current body composition values may be obtained from one or more third party applications 530 that are connected to and exchange data with the body change journey management layer 521.

As discussed above, the current body composition 516 of the user may be determined from 2D images provided by the user that are processed by the body composition scan 561 of the 3D body model system 520 to determine current body composition and a personalized 3D body model representative of the current body composition of the user. Likewise, the goal body composition may be determined based on adjustments made by the user to the 3D body model or otherwise provided by the user. Alternatively, if the user is specifying a body change journey duration and a body measurement of interest, the user may provide that information through, for example, the mobile device 501. Demographics 511, known health issues 513, food preferences 514, exercise preferences 515, etc., may also be provided directly by the user, from wearables 570, from third party applications 530, or otherwise determined.

In some implementations, movement assessment 573 may also be determined for the body of the user. For example, data from the mobile device 501 and/or data from wearables 570 worn on the body of the user may be processed to determine the movement, referred to herein as movement assessment, of the body of the user. Movement assessment 573 data may also be provided to and stored in the data store 522.

Based on the demographics of the user, current body composition, known health issues, food preferences, movement assessment, and/or exercise preferences (referred to herein collected as body traits), the body change journey management layer 521 may determine and assign the user to a cohort. A cohort may be a group of individuals with similar body traits that are managed by the 3D body model system and for which data is available as to body change journey configurations that work for that cohort. For example, based on check-ins performed by other users in the same cohort, the 3D body model system may determine what activities (e.g., sleep, exercise, etc.), foods, calorie consumption, etc., work and do not work well for users of that cohort to progress along a body change journey. As more users progress through body change journeys with the 3D body model system, as discussed below, the cohort and systems trained to generate body change journeys for the cohort may be refined and improved. Likewise, as discussed below, based on feedback from the user, progress of the user, etc., the user, during a body change journey, may be reassigned to a different cohort and the body change journey updated based on that newly assigned cohort.

The rules portal/machine learning engine 550) may be used by the 3D body model system to generate the body change journey for the user based on the information provided about the user. The body change journey may include one or more of a nutrition program 551, an exercise program 552, a time duration, and expected body changes during the time duration. For example, one or more machine learning algorithms may be trained for a cohort to which the user is assigned and, based on the demographics 511 of the user, the current body composition 516 of the user, goal body composition 512, known health issues 513 of the user, etc., may generate a body change journey for the body of the user that will guide the body of the user along a healthy path from the current body composition to the goal body composition. Likewise, the food preferences 514, exercise preferences 515, activity level of the user, etc., may be utilized to further refine and personalize the body change journey determined by the machine learning algorithm 550. In other implementations, the machine learning algorithm 550 may be trained to further consider one or both of the food preferences 514 and the exercise preferences 515 of the user as part of the generation of the body change journey for the user.

In examples in which the user has specified a time duration for the body change journey, the system, utilizing the cohort data may determine expected body measurements for the body of the user throughout and/or at the end of the duration of the body change journey specified by the user. Similar to the above example, the body measurements determined for the body change journey of a specified duration may be determined based on a body change journey determined for the user, based on the demographics 511 of the user, the current body composition 516 of the user, known health issues 513 of the user, etc., that will guide the user along a healthy path during the duration of the body change journey. Likewise, the food preferences 514, exercise preferences 515, activity level of the user, etc., may be utilized to further refine and personalize the body change journey and the body measurements expected at the end of the specific duration of the body change journey.

In some implementations, different levels of activity and the expected change in the body change journey may be overlaid or presented with the body change journey to indicate to the user how changes by the user, such as a change in activity level, change in food/alcohol consumption, etc., may impact the trajectory of the body change journey.

The information provided by the user during registration, received from wearables 570, received from third party applications 530, determined from the body composition scans 561, and/or the body change journey generated by the rules portal/machine learning algorithms 550 for a user may be stored in a data store 522, associated with the user, used to define a cohort for the user, and be accessible to the 3D body model system.

Additionally, in some implementations, the data maintained in the data store may be anonymized to remove any user identifying information and that anonymized data may be used to continue to refine the 3D body model system, continue to train the one or more machine learning algorithms, etc.

As discussed above, the user may participate in periodic check-ins with the 3D body model system and provide updated 2D images of the body of the user that are used to determine the user's progress along the body change journey and to provide feedback to the user. Likewise, data from one or more of the wearables 570 and/or third party applications 530 may be collected as the user participates in the body change journey and that data may be used during the check-ins, to determine or update the cohort for the user, etc. For example, glycemic response 572 data received from a wearable 570 may be used to detect the response of the body of the user after eating in terms of a glycemic index, which may be used to provide information as to how the food the user is eating is affecting the body of the user. Such information may also be used at a check-in to determine if the user is following the determined nutrition program 551 and/or if the body of the user is associated with the appropriate cohort.

Figure 6A:
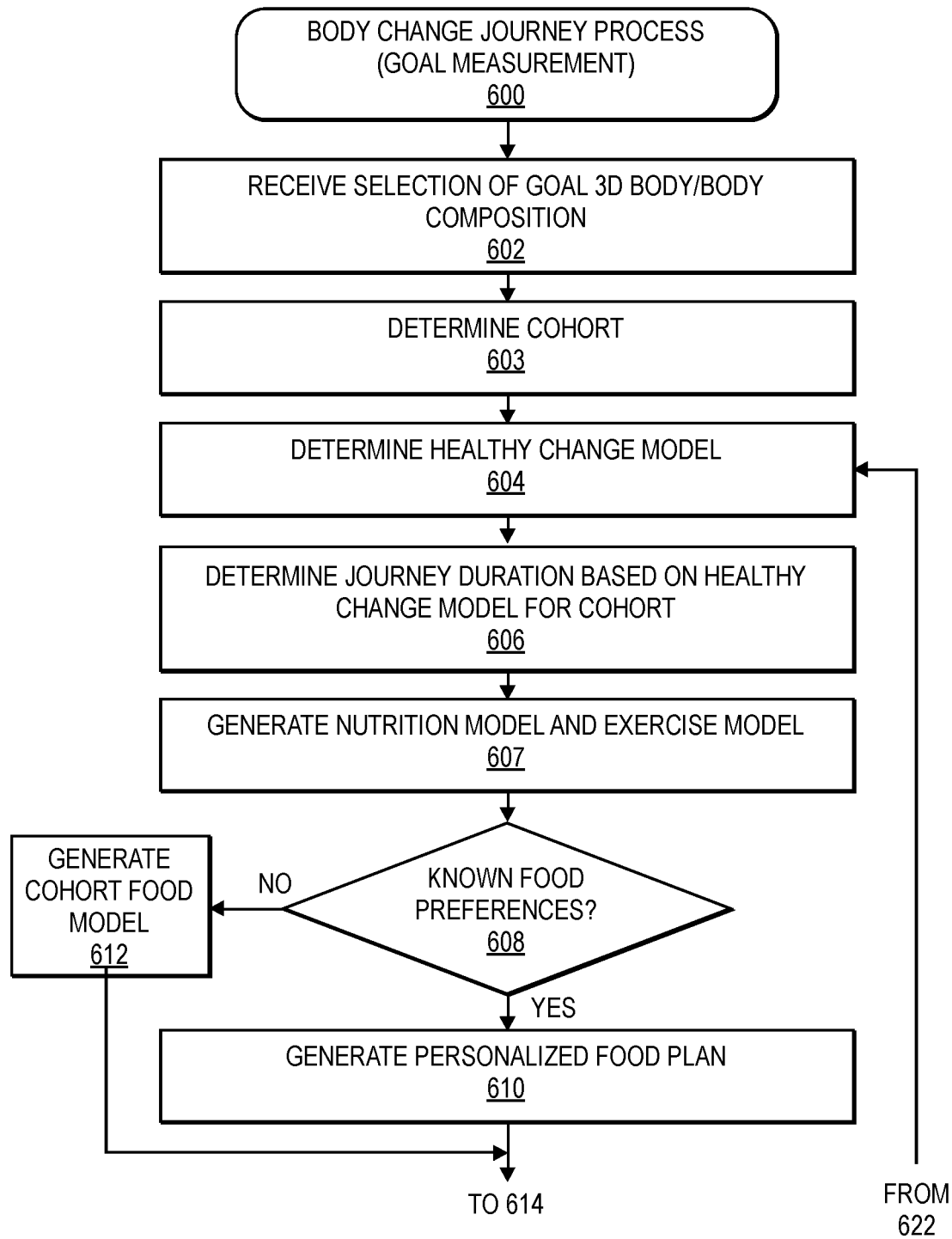
FIGS. 6A-6B is an example body change journey process based on a provided goal body measurement, in accordance with implementations of the present disclosure.
Figure 6B:
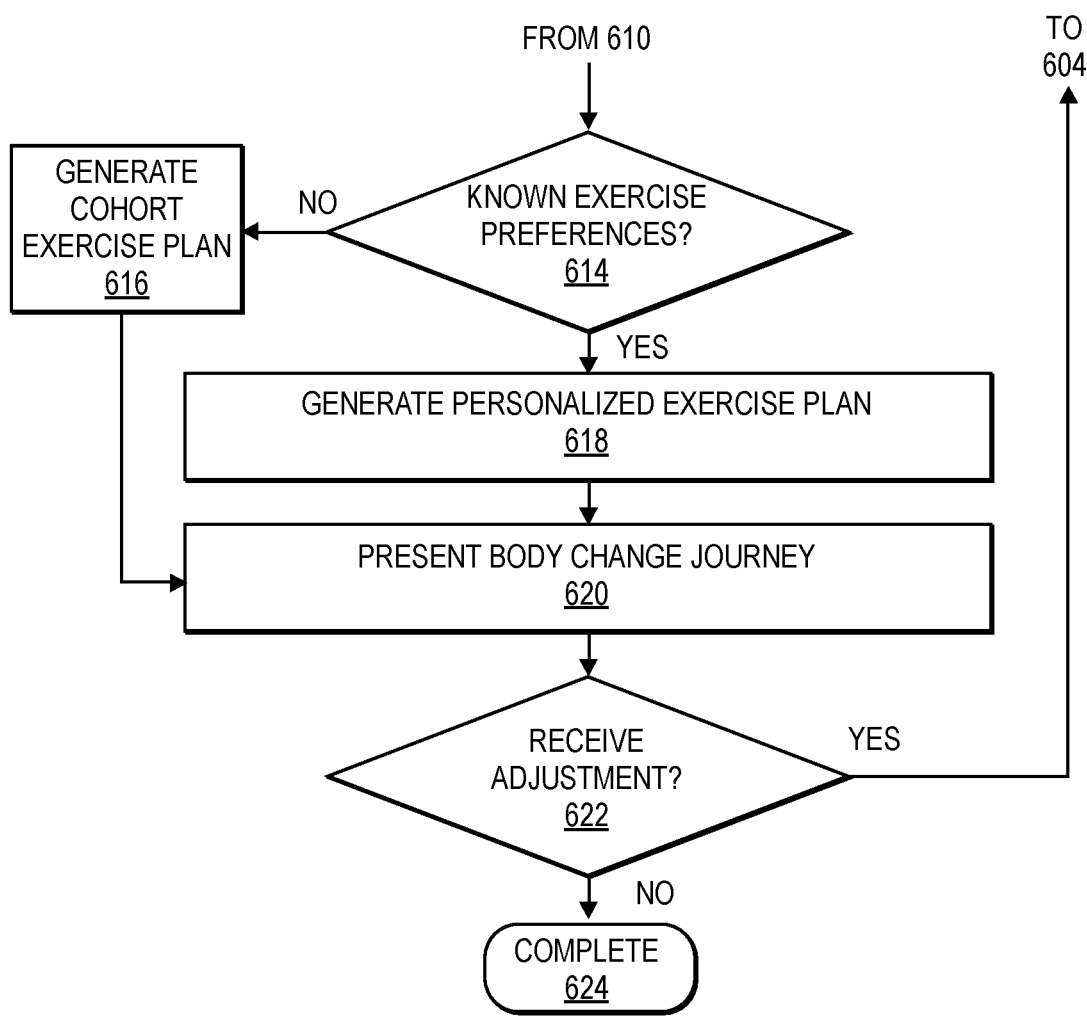

FIGS. 6A-6B is an example body change journey process 600, in accordance with implementations of the present disclosure.

Turning first to FIG. 6A, the example process 600 begins upon receipt of a selection of predicted personalized 3D body models or predicted personalized body compositions presented to a user as a goal 3D body model and goal body composition, as in 602. Alternatively, the user may specify a desired body change or goal body measurement value independent of the predicted personalized 3D body models.

To generate the body change journey from the current body composition of the user to the goal body composition, the example process 600 determines a cohort for the user, as in 603. Cohort determination is discussed below with respect to FIG. 8. In addition, a healthy change model may likewise be determined, as in 604. For example, if the user is trying to lose body fat and gain muscle, it may be determined that the body change journey should target for no more than one pound of body fat loss per week as lower calorie consumption may be unhealthy for the user and/or may hinder muscle growth. In some implementations, the healthy change model may be selected based on the cohort to which the user is associated and/or based on preferences specified by the user.

Based on the difference between the current body measurements, the goal body measurements, and the healthy change model, a time duration for the body change journey may be determined, as in 606. For example and continuing with the above, if the user currently weighs 206 pounds with 23% body fat (i.e., 158.62 pounds of lean mass/bone and 47.38 pounds of body fat), has a goal body composition of 195 pounds and 10% body fat (i.e., 175.5 pounds of lean mass/bone and 19.5 pounds of body fat), and the healthy change model determined from the cohort specifies that no more than one pound of body fat be lost per week and no more than one pound of lean mass added per week, the body change journey time duration will be 28 weeks because the user needs to lose a total of 27.88 pounds of body fat and add 16.88 pounds of lean mass/bone.

In addition to determining the body change journey time duration, the example process may also generate a nutrition model and an exercise model that are to be followed to change the body of the user from the current body composition to the goal body composition, as in 607. The nutrition model and exercise model, which are interrelated, may be determined based on the cohort to which the user is assigned to increase the likelihood of compliance and success by the user. For example, if the user has a current activity level of sedentary, the exercise program should reflect that current activity level and start with a low impact or low difficulty exercise program that can actually be accomplished by the user. Likewise, the nutrition plan will be tailored more toward balanced macronutrients and fat loss, rather than muscle growth, at least initially. As the user progresses along the body change journey and changes cohorts as a result of the increased activity level, better eating habits, body fat loss, etc., the 3D body model system will reassign the user to a different cohort and the exercise and nutrition models will change correspondingly so that the user continues to progress.

A determination may also be made as to whether user food preferences are known, as in 608. As discussed above, food preferences may be specified by the user and/or determined based on foods consumed by the user, information received from food logging activities of the user, information received from third party applications, etc.

If there are known food preferences, a personalized food plan is generated for the user that may include food or meal recommendations that satisfy the nutrition model and that are based on food preferences of the user, as in 610. However, if food preferences of the user are not known, a cohort food plan may be generated that satisfies the nutrition model and is based on foods often consumed by other members of the cohort to which the user is currently assigned, as in 612. As the user progresses through the body change journey, the user may select to change a food or a meal and the 3D body model system may recommend alternative foods/meals that maintain compliance with the determined nutrition model. In addition, the system may maintain information indicating foods selected by the user and foods changed by the user to develop or update a food preferences list of the user.

Referring now to FIG. 6B, a determination may also be made as to whether the user exercise preferences are known, as in 614. Similar to food preferences, a user may specify exercise preferences, exercise preferences may be determined from wearables or third party apps associated with the user, and/or exercise preferences may be determined from exercises logged by the user.

If it is determined that exercise preferences of the user are known, a personalized exercise plan is developed for the user that complies with the exercise model and is based on the exercise preferences of the user, as in 618. If exercise preferences of the user are not known, a cohort exercise plan is developed that corresponds with the exercise model and is based on exercises most often performed by other members of the cohort to which the user is currently assigned, as in 616. As the user progresses through the body change journey, the user may select to change an exercise and the 3D body model system may recommend alternative exercises that maintain compliance with the determined exercise model. In addition, the system may maintain information indicating exercises selected by the user and exercises changed by the user to develop or update an exercise preferences list of the user.

Based on the cohort determined body change journey duration, determined nutrition plan (cohort or personalized) and determined exercise plan (cohort or personalized), the body change journey is generated and presented to the user, as in 620.

After presentation of the body change journey, it may be determined whether an adjustment to the body change journey has been received from the user, as in 622. As discussed above, a user may select to change one or more high level aspects (e.g., daily calorie limit, weekly exercise plan, journey duration, etc.) of the body change journey. If it is determined that an adjustment to one or more aspects of the body change journey have been received, the example process 600 returns to block 604 and continues by re-evaluating the body change journey considering the received adjustment. For example, if the received adjustment is an increase in the weekly exercise plan, re-evaluation of the body change journey may determine that the duration of the body change journey may decrease and/or that the daily calorie limit may increase for the user to reach the goal 3D body model/body composition.

If it is determined that an adjustment has not been received, the example process 600 completes, as in 624.

Figure 7A:
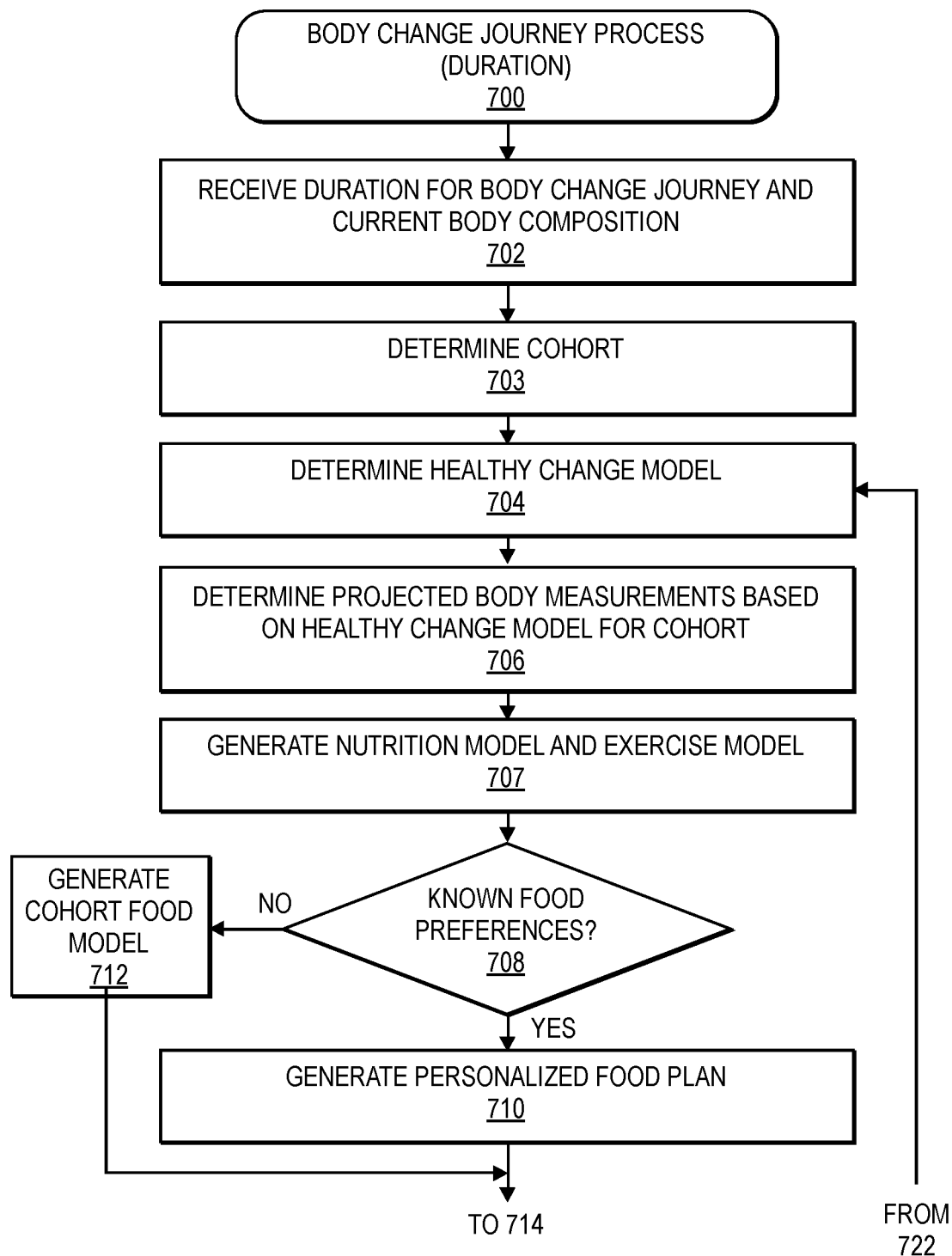
FIGS. 7A-7B is an example body change journey process based on a provided goal body measurement, in accordance with implementations of the present disclosure.
Figure 7B:
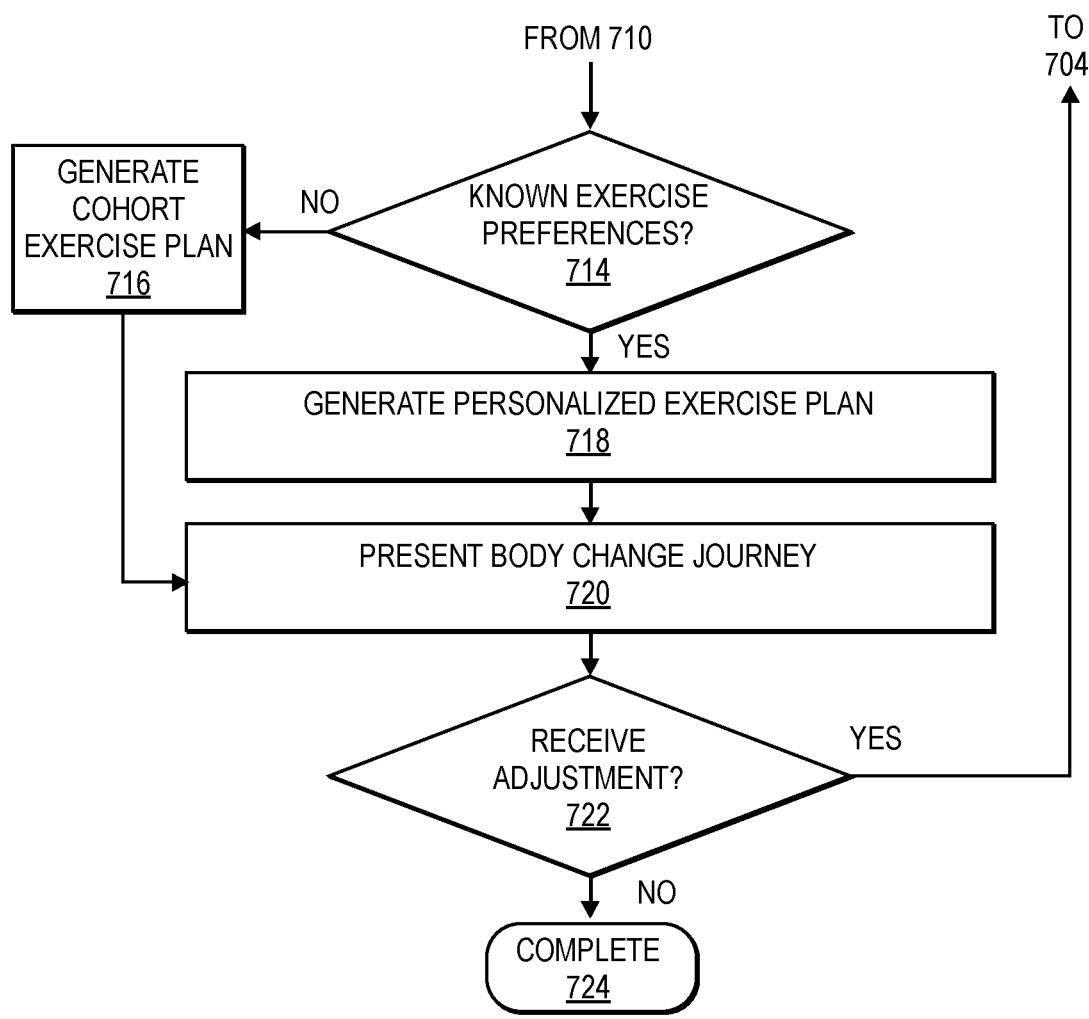

FIGS. 7A-7B is another example body change journey process 700, in accordance with implementations of the present disclosure. The example 700 discusses generation of a body change journey when the user provides a duration for the body change journey.

Turning first to FIG. 7A, the example process 700 begins upon receipt of a duration, such as ninety days, for a body change journey that is to be created for the user and a current body composition, as discussed, for the body of the user, as in 702.

To generate the body change journey from the current body composition of the user for the user specified duration, the example process 700 determines a cohort for the user, as in 703. Cohort determination is discussed below with respect to FIG. 8. In addition, a healthy change model may likewise be determined, as in 704. For example, if the user is trying to lose body fat and gain muscle during the duration of the body change journey, it may be determined that the body change journey should specify no more than one pound of body fat loss per week as lower calorie consumption may be unhealthy for the user and/or may hinder muscle growth. In some implementations, the healthy change model may be selected based on the cohort to which the user is associated and/or based on preferences specified by the user.

Based on the user specified duration of the body change journey and the associated cohort, a predicted body composition may be determined for the body of the user at the end of the duration, as in 706. For example, based on the determined body change model, the cohort, and the current body composition of the body of the user, predicted body measurement values at the end of the body change journey duration can be predicted. For example, if the user currently weighs 206 pounds with 23% body fat (i.e., 158.62 pounds of lean mass/bone and 47.38 pounds of body fat), the body change journey specifies that the user should attempt to lose no more than one pound per-week, and the user has specified ninety days as the duration of the body change journey, it may be determined that the body of the user, if the user follows the body change journey should lose approximately 12.9 pounds during the duration of the body change journey, which results in a goal body weight of 193.1 pounds.

In addition to determining the body change journey and the goal body measurement based on the user specified duration, the example process may also generate a nutrition model and an exercise model that are to be followed to change the body of the user from the current body composition to the goal body composition during the duration of the body change journey, as in 707. The nutrition model and exercise model, which are interrelated, may be determined based on the cohort to which the user is assigned to increase the likelihood of compliance and success by the user. For example, if the user has a current activity level of sedentary, the exercise program should reflect that current activity level and start with a low impact or low difficulty exercise program that can actually be accomplished by the user. Likewise, the nutrition plan will be tailored more toward balanced macronutrients and fat loss, rather than muscle growth, at least initially. As the user progresses along the body change journey and changes cohorts as a result of the increased activity level, better eating habits, body fat loss, etc., the 3D body model system will reassign the user to a different cohort and the exercise and nutrition models will change correspondingly so that the user continues to progress.

A determination may also be made as to whether user food preferences are known, as in 708. As discussed above, food preferences may be specified by the user and/or determined based on foods consumed by the user, information received from food logging activities of the user, information received from third party applications, etc.

If there are known food preferences, a personalized food plan is generated for the user that may include food or meal recommendations that satisfy the nutrition model and that are based on food preferences of the user, as in 710. However, if food preferences of the user are not known, a cohort food plan may be generated that satisfies the nutrition model and is based on foods often consumed by other members of the cohort to which the user is currently assigned, as in 712. As the user progress through the body change journey, the user may select to change a food or a meal and the 3D body model system may recommend alternative foods/meals that maintain compliance with the determined nutrition model. In addition, the system may maintain information indicating foods selected by the user and foods changed by the user to develop or update a food preferences list of the user.

Referring now to FIG. 7B, a determination may also be made as to whether the user exercise preferences are known, as in 714. Similar to food preferences, a user may specify exercise preferences, exercise preferences may be determined from wearables or third party apps associated with the user, and/or exercise preferences may be determined from exercises logged by the user.

If it is determined that exercise preferences of the user are known, a personalized exercise plan is developed for the user that complies with the exercise model and is based on the exercise preferences of the user, as in 718. If exercise preferences of the user are not known, a cohort exercise plan is developed that corresponds with the exercise model and is based on exercises most often performed by other members of the cohort to which the user is currently assigned, as in 716. As the user progresses through the body change journey, the user may select to change an exercise and the 3D body model system may recommend alternative exercises that maintain compliance with the determined exercise model. In addition, the system may maintain information indicating exercises selected by the user and exercises changed by the user to develop or update an exercise preferences list of the user.

Based on the cohort determined body change journey duration, determined nutrition plan (cohort or personalized) and determined exercise plan (cohort or personalized), the body change journey is generated and presented to the user, as in 720.

After presentation of the body change journey, it may be determined whether an adjustment to the body change journey has been received from the user, as in 722. As discussed above, a user may select to change one or more high level aspects (e.g., daily calorie limit, weekly exercise plan, journey duration, etc.) of the body change journey. If it is determined that an adjustment to one or more aspects of the body change journey have been received, the example process 700 returns to block 704 and continues by re-evaluating the body change journey considering the received adjustment. For example, if the received adjustment is an increase in the weekly exercise plan, re-evaluation of the body change journey may determine that the duration of the body change journey may decrease and/or that the daily calorie limit may increase for the user to reach the goal 3D body model/body composition.

If it is determined that an adjustment has not been received, the example process 700 completes, as in 724.

Figure 8:
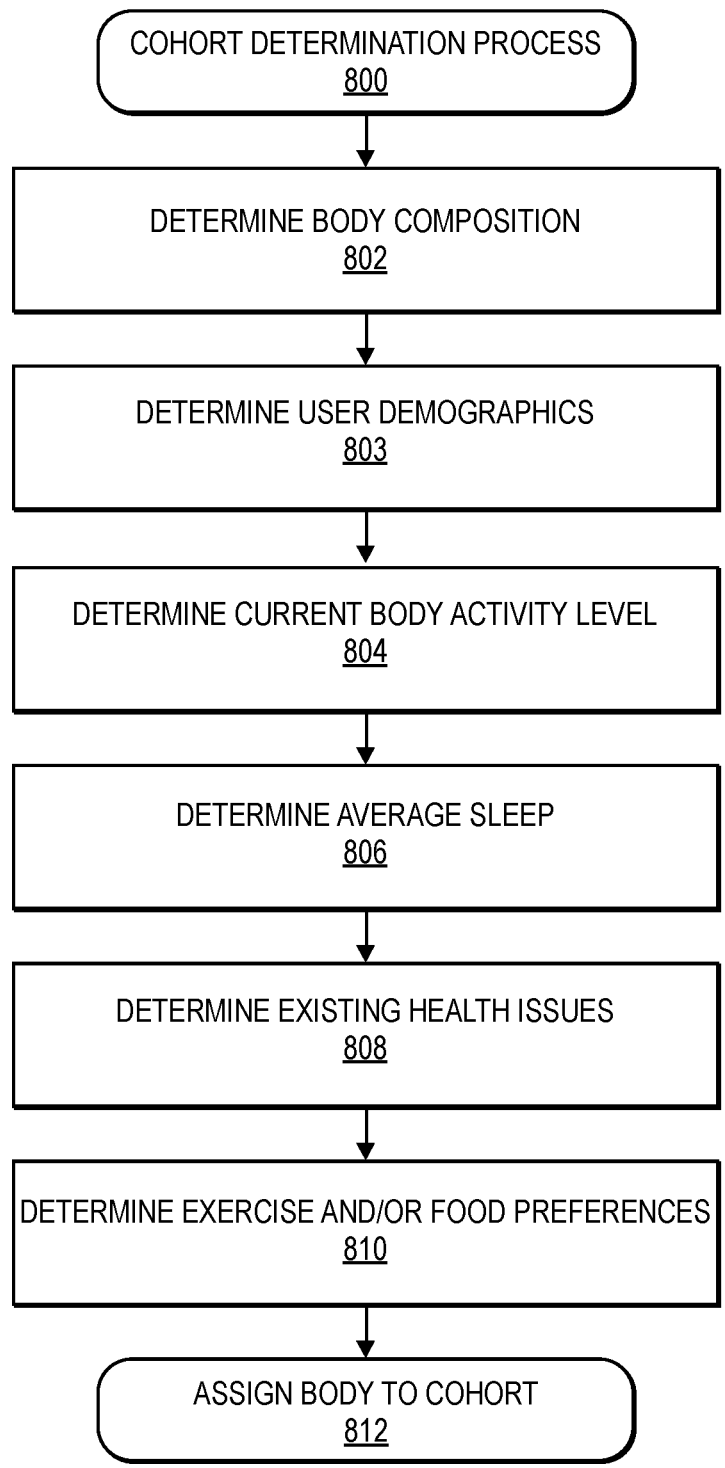
FIG. 8 is an example cohort determination process, in accordance with implementations of the present disclosure.

FIG. 8 is an example cohort determination process 800, in accordance with implementations of the present disclosure.

The example process 800 begins by determining the body composition of the user, as in 802. As discussed above, the body composition of the user may be determined from 2D body images provided by the user, based on inputs from the user, and/or based on data obtained from wearables or third party applications associated with the user. The example process 800 may also determine the user demographics of the user, which may be provided by the user or otherwise determined, as in 803.

In addition, a current activity level of the user may optionally be determined, as in 804. The current activity level may be determined based on input provided by the user as part of registration with the 3D body model system, based on information obtained from a wearable or mobile device associated with the user, based on data obtained from one or more third party applications, etc. In some implementations, the user activity level may be categorized into one of several categories (e.g., sedentary, lightly active, active, highly active). Still further, in some examples, the average sleep of the user over a period of time may be determined, as in 806.

The example process 800 may also optionally determine any existing health issues, as in 808. Health issues could be any health issues provided by the user as part of registration or subsequent to registration. In some implementations, the user may provide access to health data from third party sources that may be obtained to determine any current health issues. In still other examples, the example process 800 may determine exercise and/or food preferences, as in 810. As discussed above, a user may provide exercise and/or food preferences directly to the example process. In other implementations, the example process may determine or infer food preferences based on food consumed by the user and/or food logging information provided by the user and/or from third party applications associated with the user.

Finally, the determined body composition, user demographics and optionally one or more of the user activity level, average sleep, existing health issues, exercise and/or food preferences, and/or other information determined about a user (collectively body traits), may be compared to one or more cohorts of other users managed by the disclosed implementations to determine a cohort that is most similar to the user. Any of a variety of techniques may be used to determine similarity between a body trait and traits of a cohort. For example, each body trait of the user may be compared with traits of existing cohorts. In other examples, each body trait may be utilized to generate a user embedding vector representative of the user. Likewise, cohort embedding vectors for each cohort may be generated based on traits of the cohort and the user embedding vector compared with cohort embedding vectors to determine which cohort embedding vector is closest to the user embedding vector in an embedding vector space. In still other examples, the body traits of the user may be utilized to dynamically generate a cohort that includes body data similar to the body traits of the user. Finally, based on the similarity determination, the user may be assigned to a particular cohort, as in 812.

The example cohort determination process 800 may be periodically performed and the user may be reassigned to a different cohort as the body traits of the user change. For example, as the user activity level changes, body fat percentage changes, weight changes, etc., the user may become more similar to a different cohort and reassigned to that cohort. As discussed, in response to a cohort reassignment, the body change journey may be updated to reflect information known about that cohort so that the journey continues to progress in a predictable manner.

Figure 9:
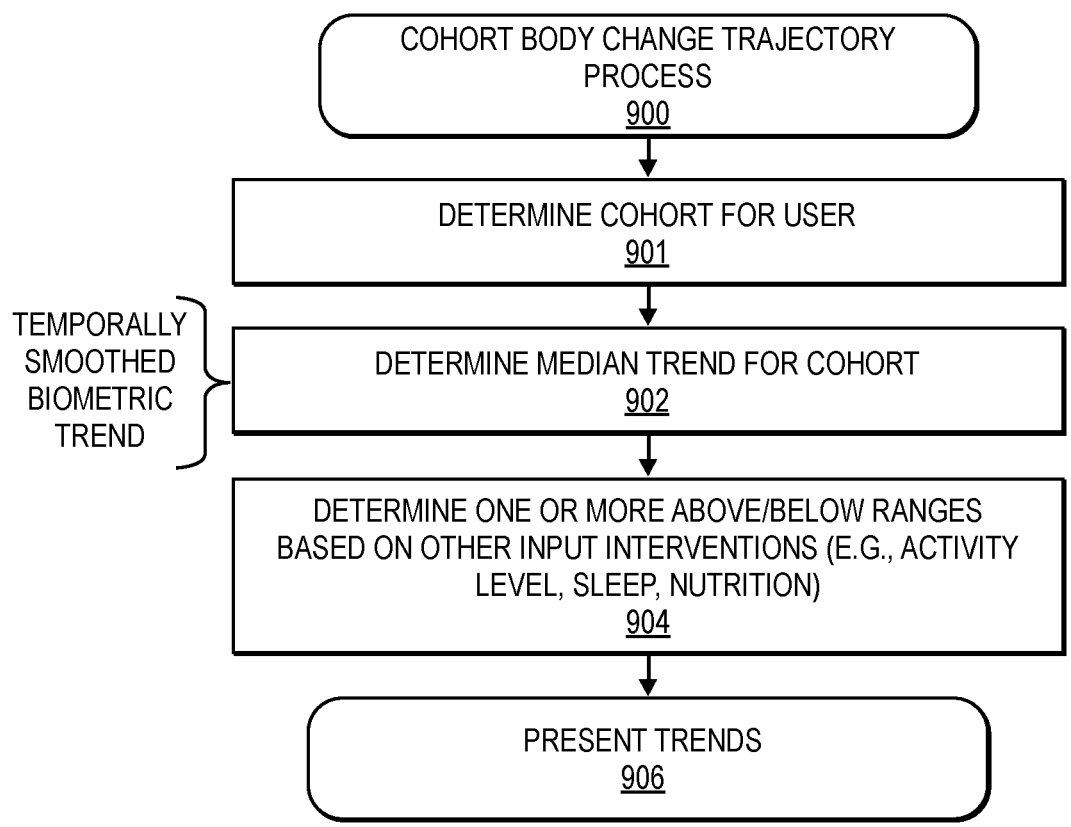
FIG. 9 is an example cohort body change trajectory process, in accordance with implementations of the present disclosure.

FIG. 9 is an example cohort body change trajectory process 900, in accordance with implementations of the present disclosure.

The example process 900 begins by defining a cohort for a body of a user, as in 901. As discussed above with respect to FIG. 8, a cohort may be defined based on any of a variety of factors, such as age, demographic, gender, activity level, body mass, height, weight, food preferences, exercise/activity level, a muscle mass of the body, a fat free mass of the body, a waist-to-hip ratio of the body, etc. In some implementations, a user may specify the number of factors to be considered in defining a cohort for the user, with the more factors/inputs provided by the user the more specific the cohort may be to the user. However, in some instances, too many inputs may unnecessarily restrict the number of members included in the cohort. As such, in some implementations the number of types of inputs may be limited to ensure a cohort of a defined minimum size, thereby increasing accuracy in the body change journey predictions. As discussed, the cohort may include anonymized data from any of a number of users, collected over a period of time, that may be utilized to predict a body change journey and corresponding body measurement values for the body of the user.

Based on the cohort defined or selected for the user, a median trend line may be defined for the selected body measurement value(s) (goal) or the specified duration of the body change journey, as in 902. For example, biometric data over a duration of time for members of the cohort having body measurement values similar to the current body measurement values of the body of the user and the goal body measurement values may be determined and smoothed to generate a median trend line. Likewise, one or more upper or lower ranges above or below the trend line may also be determined from the member data of the cohort, as in 904. For example, the results and number of cohort members in the twenty five percent range below the median trend line may be determined from the member data of the cohort and utilized as additional information for the user. Likewise, in some implementations, the interventions or other inputs from members in the different ranges above/below the median trend line may also be determined and suggested to the user as additional motivation. For example, it may be determined that members of the cohort in the lower twenty-five percent trend line measuring body fat over time (i.e., those that lost more than the median) all added the activity of sit-ups (an intervention) five days per week. Such information may be presented to the user as additional motivation as the user progresses along their body change journey.

Finally, the median trend line, ranges above/below the median trend line, and optionally interventions related to the ranges may be presented to the user as information relevant to the body change journey, as in 906.

Figure 10:
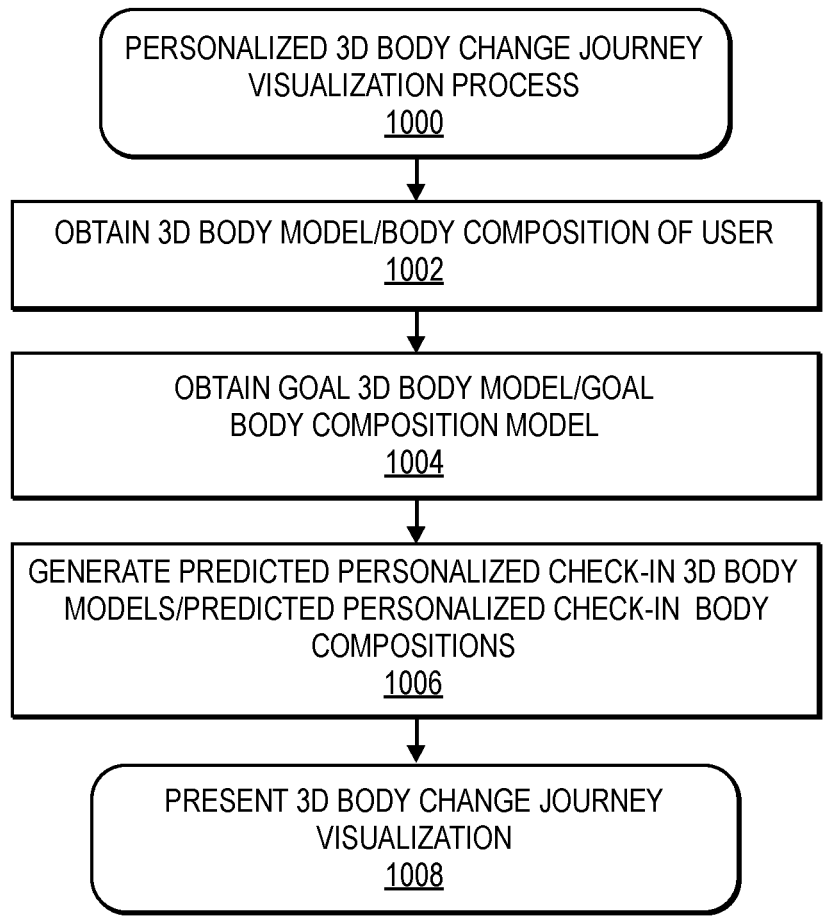
FIG. 10 is an example personalized 3D body change journey visualization process, in accordance with implementations of the present disclosure.

FIG. 10 is an example personalized 3D body model journey process 1000, in accordance with implementations of the present disclosure. The example process 1000 may be performed upon generation of a body change journey and/or when a user is considering a suggested body change journey between a current body composition of the user and a goal body composition.

The example process 1000 begins by obtaining a current 3D body model and current body composition values of a user, as in 1002. Likewise, the selected goal 3D body model and goal body model composition are obtained, as in 1004. As discussed above, the current 3D body model and current body composition of a user can be determined based on 2D images provided by the user. A goal 3D body model and goal body model composition may be determined based on a user's adjustments to a current 3D body model, based on body measurement values provided by the user, and/or based on a goal body image, such as a body image of a celebrity selected or provided by the user.

Based on the current 3D body model, current body composition, goal 3D body model, and goal body composition, predicted personalized 3D body models and corresponding predicted personalized body composition values are determined for check-ins that may be performed during a body change journey. For example, check-ins may be performed once per week as part of a body change journey. In such an example, predicted personalized 3D body models and corresponding predicted personalized body composition values may be generated for each of the weekly check-ins that correspond with a predicted progress of the user as the user follows the body change journey. Generation of predicted personalized 3D body models and corresponding body composition values are discussed below with respect to FIGS. 17 through 19. Finally, the current 3D body model, goal 3D body model, and the generated predicted personalized 3D body models generated between the current 3D body model and the goal 3D body model may be presented to the user to visualize the progress and change of the body of the user if the user follows the body change journey, as in 1008, and as illustrated in FIG. 11.

FIG. 11 is a block diagram illustrating predicted personalized 3D body models 1100 for a determined body change journey, in accordance with implementations of the present disclosure.

As illustrated, the current 3D body model 1100 is representative of the current body of the user and may be determined from 2D images of the user. The goal 3D body model 1104 may be determined based on a user's adjustments to the current 3D body model or based on alternations to one or more body measurements specified by the user, all as discussed above. To further visualize the change to the body of the user as the user progresses through the body change journey, the predicted personalized 3D body models 1102, 1103, etc., generated for each check-in as the user progresses through the body change journey may also be visualized to provide a visual indication of the changes to the body of the user that are predicted if the user follows the body change journey. While the example 1100 illustrates two predicted personalized 3D body models, any number of predicted personalized 3D body models may be generated and presented between the current 3D body model of the user and the goal 3D body model of the user.

Figure 12A:
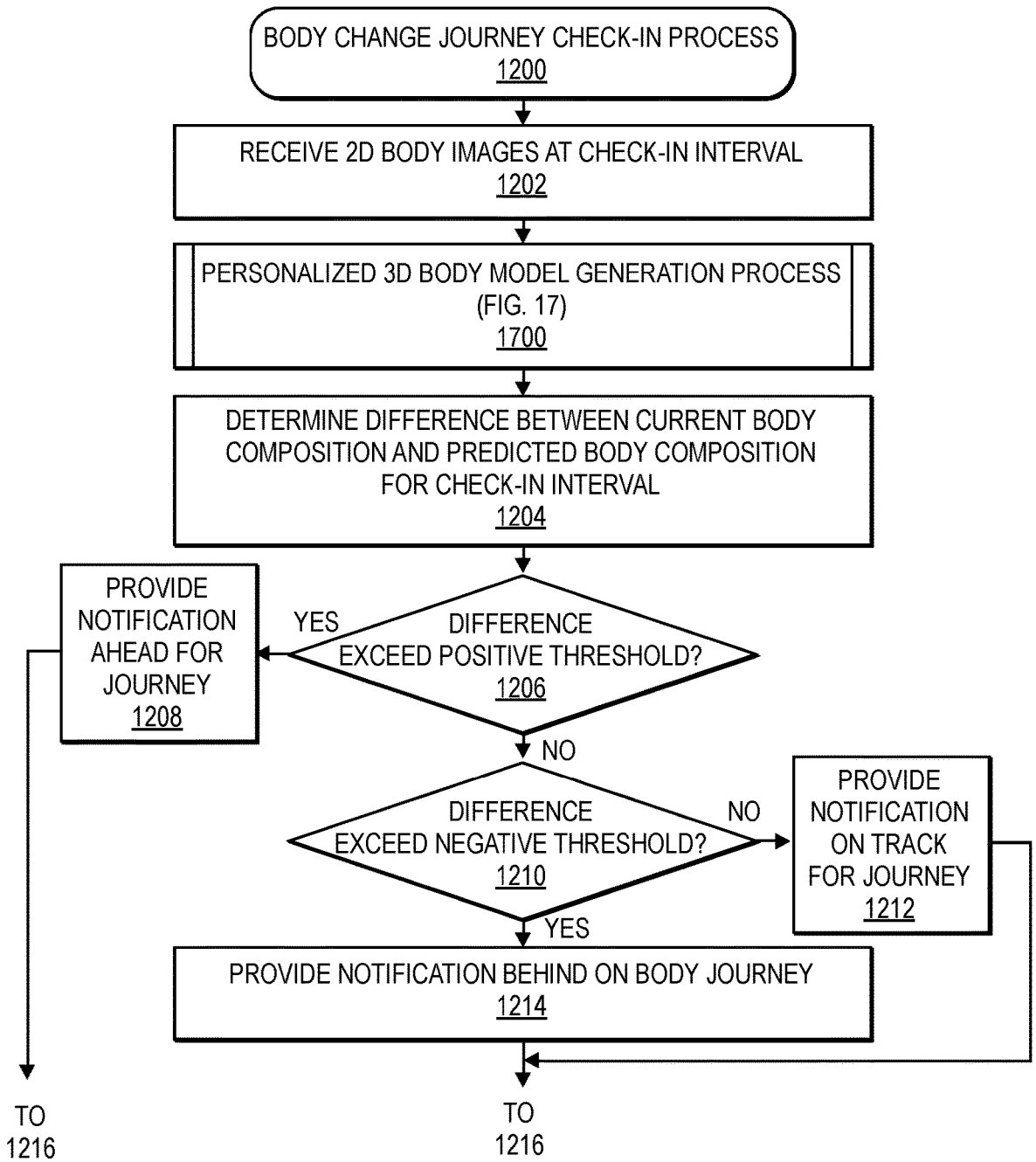
FIGS. 12A-12B is an example body change journey check-in process, in accordance with implementations of the present disclosure.
Figure 12B:
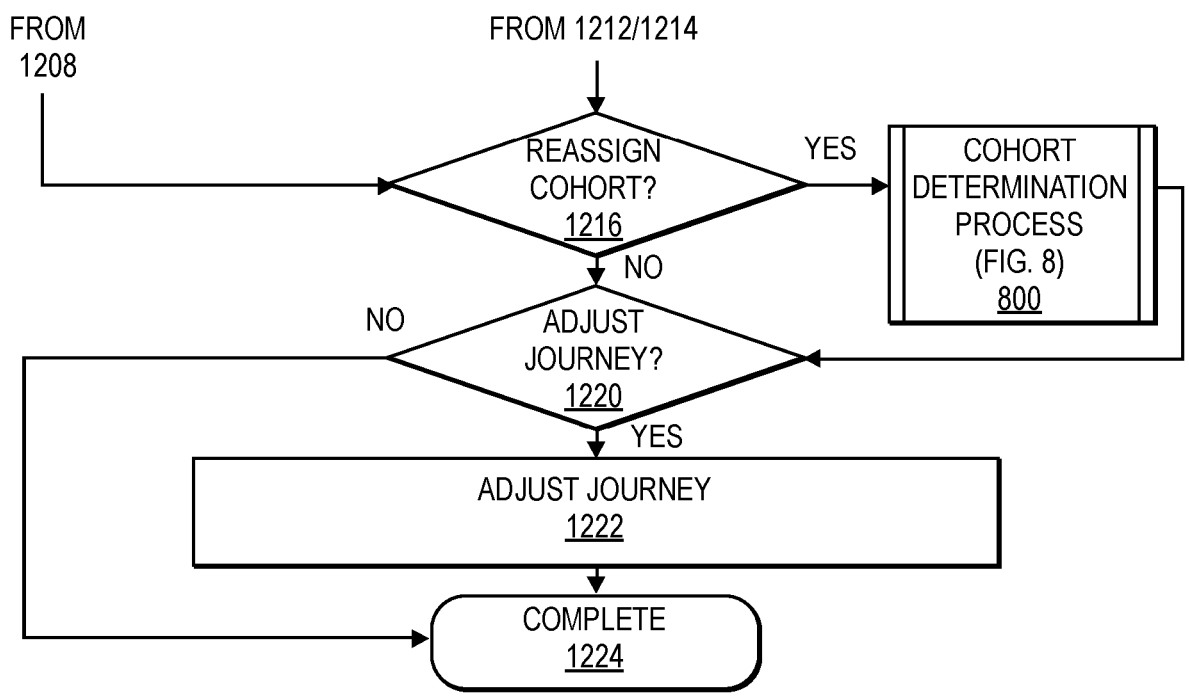

FIGS. 12A-12B is an example body change journey check-in process 1200, in accordance with implementations of the present disclosure.

Turning first to FIG. 12A, the example process 1200 begins upon receipt of 2D body images of a user at a check-in interval of a body change journey, as in 1202. As discussed above, period check-ins, such as weekly, may be established as part of a body change journey to assess the user's progress along the body change journey, determine if changes need to be made to the body change journey, change cohorts with which the user is associated, etc.

Utilizing the 2D body images, a personalized 3D body model of the user is generated in accordance with the personalized 3D body model generation process 1700 discussed below with respect to FIG. 17.

A difference may then be determined between the current body composition determined for the current personalized 3D body model and the predicted body composition determined for the check-in, as in 1204. For example, a difference between current body measurements (e.g., weight, body fat, arm circumference, waist circumference, etc.) between the current body measurements determined from the 2D images and the predicted body measurements determined for the check-in may be determined. In some implementations, an overall difference or average difference between the current body composition and the predicted body composition may be determined.

A determination may then be made as to whether the difference exceeds a positive difference threshold, as in 1206. A positive difference threshold may provide an indication that the user is progressing toward the goal body model at a faster pace than was predicted for the body change journey. Likewise, the positive difference threshold may be any value or indicator and may vary for different users, different cohorts, etc. A positive difference that exceeds the positive difference threshold may occur for a variety of reasons. For example, the user may be exercising more than specified in the body change journey, the user may be eating less or healthier than is specified in the body change journey, the user may not align well with the assigned cohort and the body of the user is responding differently than predicted, etc.

If it is determined that the difference exceeds the positive difference threshold, a notification may be provided to the user that they are ahead for the body change journey, as in 1208. If it is determined that the difference does not exceed the positive difference threshold, a determination is made as to whether the difference exceeds a negative difference threshold, as in 1210. A negative difference threshold may provide an indication that the user is not progressing toward the goal body model as predicted for the body change journey. Similar to the positive difference threshold, the negative difference threshold may be any value or indicator and may vary for different users, different cohorts, etc. A negative difference that exceeds the negative difference threshold may occur for a variety of reasons. For example, the user may be exercising less than specified in the body change journey, the user may not be complying with the food plan, the user may not align well with the assigned cohort and the body of the user is responding differently than predicted, etc.

If it is determined that the difference exceeds the negative difference threshold, a notification is provided to the user indicating that the user is not progressing as expected or behind in the body change journey, as in 1214. In comparison, if it is determined that the difference does not exceed either of the positive difference threshold or the negative difference threshold, a notification may be provided to the user indicating that the user is on-track for the body change journey, as in 1212.

After providing a notification in block 1208, 1212, or 1214, a determination may also be made as to whether the user should be reassigned to a different cohort, as in 1216 (FIG. 12B). For example, if the body composition of the body of the user has changed such that it now is more similar to body compositions for another cohort, it may be determined that the user should be reassigned to a different cohort. Such reassignment may be performed regardless of whether the user is on-track, behind, or ahead with respect to the predicted progress of the body change journey. As another example, if the user is behind in the body change journey and it is determined from data received from a wearable, such as a glycemic response, that the body of the user is not responding to recommended foods as predicted, it may be determined that the user should be reassigned to a different cohort that responds to foods in a manner similar to that of the user.

If it is determined that the user should be reassigned to a different cohort, the cohort determination process 800 discussed above with respect to FIG. 8 may be performed again based on the new data. If it is determined that the user is not to be reassigned to a different cohort, or after reassigning the user to a different cohort, a determination is made as to whether the body change journey is to be adjusted, as in 1220. If it is determined that the body change journey is to be adjusted, the body change journey is adjusted based on the progress of the user as determined at the check-in, as in 1222. As discussed above, if the user is assigned to a different cohort, the body change journey may be adjusted based on the newly assigned cohort. As another example, if the user is not reassigned to a different cohort but is ahead in the body change journey, the duration of the body change journey may be shortened. In comparison, if the user is behind in the body change journey, the body change journey may be extended, the exercise may change, and/or the food plan may change.

Finally, after changing the body change journey or if it is determined that the body change journey is not to change, the example process completes, as in 1224.

Figure 13:
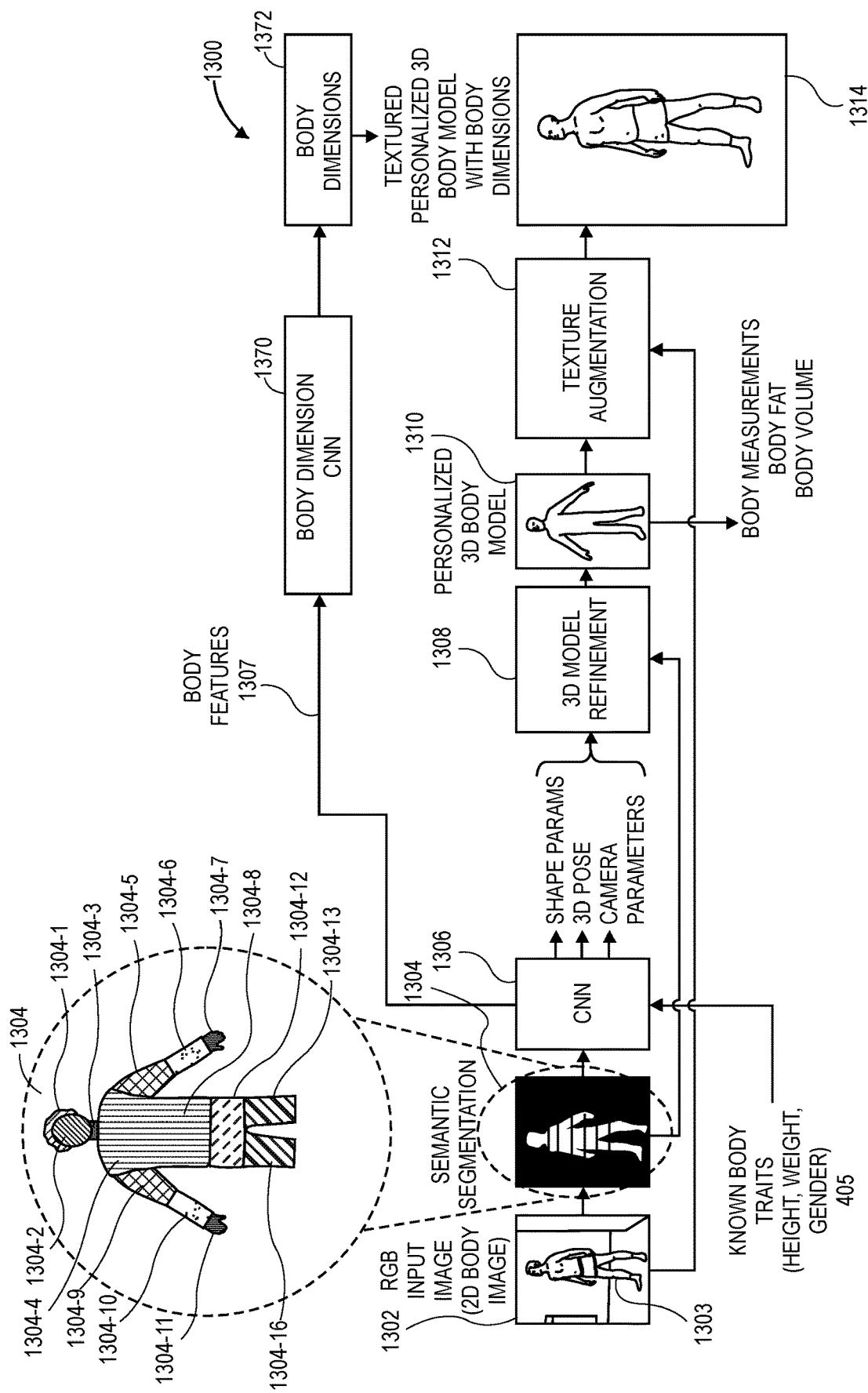
FIG. 13 is a transition diagram of processing two-dimensional body images to produce a personalized three-dimensional model of that body and corresponding body dimensions, in accordance with implementations of the present disclosure.

FIG. 13 is a transition diagram 1300 of processing 2D body images of a body to produce a personalized 3D body model and body dimensions of that body, in accordance with implementations of the present disclosure.

3D modeling and body dimension determination of a body from 2D body images begins with the receipt or creation of a 2D body image 1302 that includes a representation of the body 1303 of the user to be modeled. As discussed above, 2D body images 1302 for use with the disclosed implementations may be generated using any conventional imaging element, such as a standard 2D Red, Green, Blue ("RGB") digital camera that is included on many current portable devices (e.g., tablets, cellular phones, laptops, etc.). The 2D body image may be a still image generated by the imaging element or an image extracted from video generated by the imaging element. Likewise, any number of images may be used with the disclosed implementations.

As discussed, the user may be instructed to stand in a particular orientation (e.g., front facing toward the imaging element, side facing toward the imaging element, back facing toward the imaging element, etc.) and/or to stand in a particular pose, such as an "A pose". Likewise, the user may be instructed to stand a distance from the camera such that the body of the user is completely or partially included in a field of view of the imaging element and represented in the generated image 1302. Still further, in some implementations, the imaging element may be aligned or positioned at a fixed or stationary point and at a fixed or stationary angle so that images generated by the imaging element are each from the same perspective and encompass the same field of view.

As will be appreciated, a user may elect or opt-in to having a personalized 3D body model of the body of the user generated and may also select whether the generated personalized 3D body model and/or other information, such as determined body dimensions, may be used for further training of the disclosed implementations and/or for other purposes.

The 2D body image 1302 that includes a representation of the body 1303 of the user may then be processed to produce a segmented silhouette 1304 of the body 1303 of the user represented in the image 1302. A variety of techniques may be used to generate the silhouette 1304. For example, background subtraction may be used to subtract or black out pixels of the image that correspond to a background of the image while pixels corresponding to the body 1303 of user (i.e., foreground) may be assigned a white or other color values. In another example, a semantic segmentation algorithm may be utilized to label background and body (foreground) pixels and/or to identify different segments of the body. For example, a convolutional neural network ("CNN") may be trained with a semantic segmentation algorithm to determine bodies, such as human bodies, in images and/or to determine body segments (e.g., head segment, neck segment, torso segment, left arm segment, etc.).

In addition, or as an alternative thereto, the segmented silhouette may be segmented into one or more body segments, such as hair segment 1304-1, head segment 1304-2, neck segment 1304-3, upper clothing segment 1304-4, upper left arm 1304-5, lower left arm 1304-6, left hand 1304-7, torso 1304-8, upper right arm 1304-9, lower right arm 1304-10, right hand 1304-11, lower clothing 1304-12, upper left leg 1304-13, upper right leg 1304-16, etc. For example, the CNN may be trained with a semantic segmentation algorithm to predict for each pixel of an image the likelihood that the pixel corresponds to a segment label (e.g., hair, upper clothing, lower clothing, head, upper right arm, etc.). For example, the CNN may be trained to process each 2D body image and output, for each pixel of each image, a vector that indicates a probability for each label that the pixel corresponds to that label. For example, if there are twenty-three labels (e.g., body segments) for which the CNN is trained, the CNN may generate, for each pixel of a 2D image, a vector that includes a probability score for each of the twenty-three labels indicating the likelihood that the pixel corresponds to the respective label. As a result, each pixel of an image may be associated with a segment based on the probability scores indicated in the vector. For segments for which the CNN is trained but are not represented in the 2D image, the CNN will provide low or zero probability scores for each label indicated in the vector, thereby indicating that the segment is not visible in the 2D body image.

In some implementations, the silhouette of the body of the user may be normalized in height and centered in the image. This may be done to further simplify and standardize inputs to a CNN to those on which the CNN was trained. Likewise, a silhouette of the body of the user may be preferred over the representation of the body of the user so that the CNN can focus only on body shape and not skin tone, texture, clothing, etc.

The silhouette 1304 of the body may then be processed by one or more other CNNs 1306 that are trained to determine body traits, also referred to herein as body features, representative of the body and to produce personalized 3D body features that are used to determine body dimensions of the body and a personalized 3D body model of the body. The body features may be represented as a set of neural network weights representative of different aspects of the body. In some implementations, the CNN 1306 may be trained for multi-mode input to receive as inputs to the CNN the silhouette 1304, and one or more known body attributes 1305 of the body of the user. For example, a user may provide a height of the body of the user, a weight of the body of the user, a gender of the body of the user, etc., and the CNN may receive one or more of those provided attributes as an input.

Based on the received inputs, the CNN 1306 generates body features 1307 corresponding to the body and personalized 3D body features, such as 3D joint locations, body volume, shape of the body, pose angles, etc. In some implementations, the CNN 1306 may be trained to predict hundreds of body features of the body represented in the image 1302.

The body dimensions CNN 1370 processes the body features 1307 and determines body dimensions 1372 for the body, as discussed further below. Likewise, a personalized 3D body model of the body is generated based on the personalized 3D body features. For example, to generate the personalized 3D body model, the personalized 3D body features may be provided to a body model, such as the Shape Completion and Animation of People ("SCAPE") body model, a Skinned Multi-Person Linear ("SMPL") body model, etc., and the body model may generate the personalized 3D body model of the body of the user based on those predicted body features.

In some implementations, as discussed further below, personalized 3D model refinement 1308 may be performed to refine or revise the generated personalized 3D body model to better represent the body of the user. For example, the personalized 3D body model may be compared to the representation of the body 1303 of the user in the image 1302 to determine differences between the shape of the body 1303 of the user represented in the image 1302 and the shape of the personalized 3D body model. Based on the determined differences, the silhouette 1304 may be refined and the refined silhouette processed by the CNN 1306 to produce a refined personalized 3D body model of the body of the user. This refinement may continue until there is no or little difference between the shape of the body 1303 of the user represented in the image 1302 and the shape of the personalized 3D body model 1310. In other implementations, a 2D model image may be generated from the personalized 3D body model and that 2D model image may be compared to the silhouette and/or the 2D body image to determine differences between the 2D model image and the 2D body image or silhouette. Based on the determined differences, the personalized 3D body features and/or the personalized 3D body model may be refined until the personalized 3D body model corresponds to the body of the user represented in the 2D body image and/or the silhouette.

Still further, in some implementations, the personalized 3D body model 1310 of the body of the user may be augmented with one or more textures, texture augmentation 1312, determined from the image 1302 of the body of the user. For example, the personalized 3D body model may be augmented to have a same or similar color to a skin color of the body 1303 represented in the image 1302, clothing or clothing colors represented in the image 1302 may be used to augment the personalized 3D body model, facial features, hair, hair color, etc., of the body of the user represented in the image 1302 may be determined and used to augment the personalized 3D body model, etc.

The result of the processing illustrated in the transition 1300 is a personalized 3D body model 1314 or avatar representative of the body of the user, that has been generated from 2D body images of the body of the user. In addition, determined body dimensions may be presented with the personalized 3D body model 1314, as illustrated above.

Figure 14A:
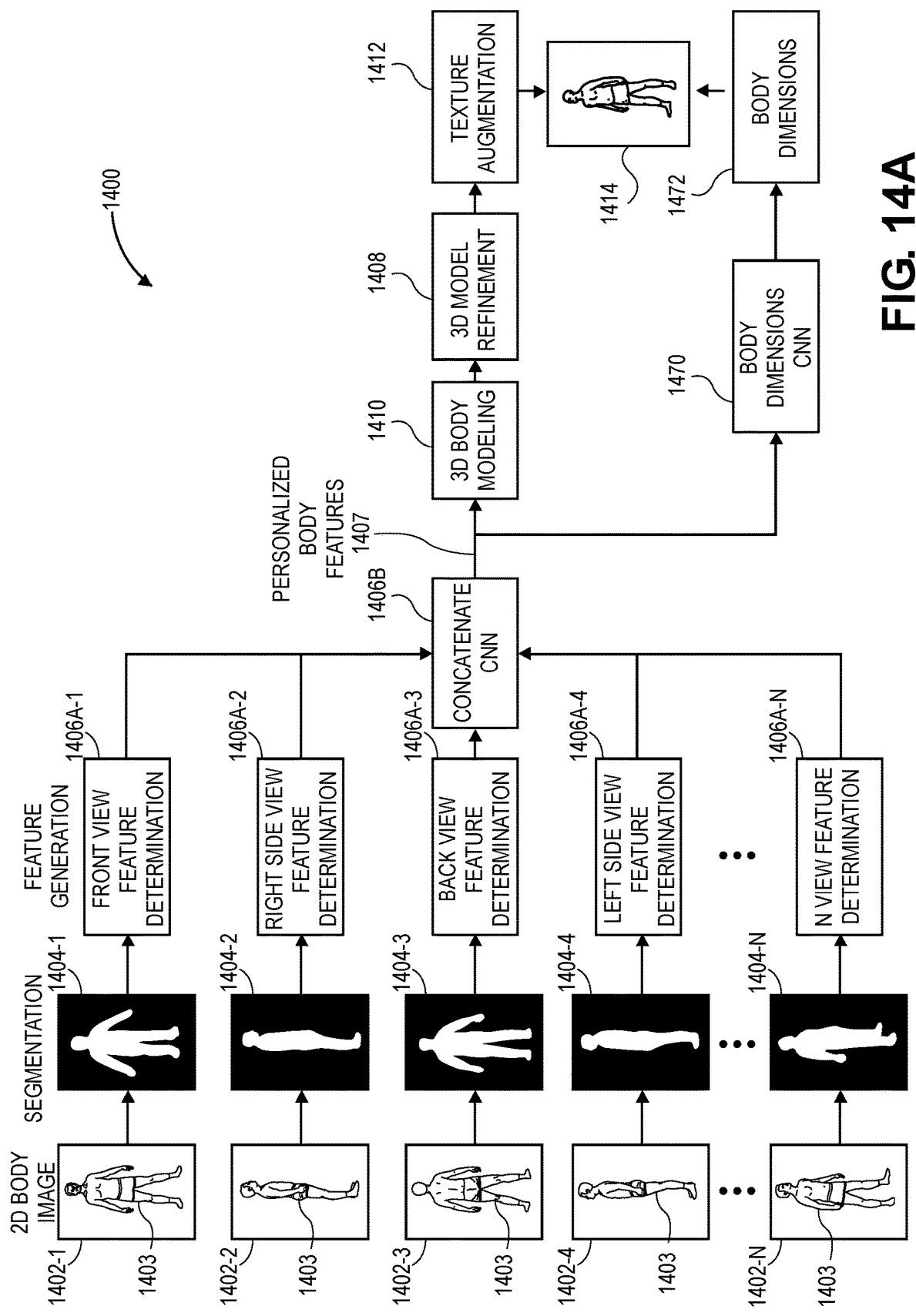
FIG. 14A is another transition diagram of processing two-dimensional body images to produce a personalized three-dimensional model of that body and corresponding body dimensions, in accordance with implementations of the present disclosure.

FIG. 14A is another transition diagram 1400 of processing 2D body images 1402 of a body to produce a personalized 3D body model and body dimensions of that body, in accordance with implementations of the present disclosure.

In some implementations, multiple 2D body images of a body from different views (e.g., front view, side view; back view, three-quarter view, etc.), such as 2D body images 1402-1, 1402-2, 1402-3, 1402-4 through 1402-N may be utilized with the disclosed implementations to generate a personalized 3D body model of the body. In the illustrated example, the first 2D body image 1402-1 is an image of a human body 1403 oriented in a front view facing a 2D imaging element. The second 2D body image 1402-2 is an image of the human body 1403 oriented in a first side view facing the 2D imaging element. The third 2D body image 1402-3 is an image of the human body 1403 oriented in a back view facing the 2D imaging element. The fourth 2D body image 1402-4 is an image of the human body 1403 oriented in a second side view facing the 2D imaging element. As will be appreciated, any number of 2D body images 1402-1 through 1402-N may be generated with the view of the human body 1403 in any number or orientations with respect to the 2D imaging element.

Each of the 2D body images 1402-1 through 1402-N are processed to segment pixels of the image that represent the human body from pixels of the image that do not represent the human body to produce a silhouette 1404 of the human body as represented in that image. Segmentation may be done through, for example, background subtraction, semantic segmentation, etc. In one example, a baseline image of the background may be known and used to subtract out pixels of the image that correspond to pixels of the baseline image, thereby leaving only foreground pixels that represent the human body. The background pixels may be assigned RGB color values for black (i.e., 0,0,0). The remaining pixels may be assigned RGB values for white (i.e., 255, 255, 255) to produce the silhouette 1404 or binary segmentation of the human body.

In another example, a CNN utilizing a semantic segmentation algorithm may be trained using images of human bodies, or simulated human bodies to train the CNN to distinguish between pixels that represent human bodies and pixels that do not represent human bodies and optionally to identify pixels of different segments of the human body. In such an example, the CNN may process the image 1402 and indicate or label pixels that represent the body (foreground) and pixels that do not represent the body (background). The background pixels may be assigned RGB color values for black (i.e., 0,0,0). The remaining pixels may be assigned RGB values for white (i.e., 255, 255, 255) to produce the silhouette or binary segmentation of the human body. For segmentation, pixels may be further processed to determine body segments of the body to which the pixels correspond.

In other implementations, other forms or algorithms, such as edge detection, shape detection, etc., may be used to determine pixels of the image 1402 that represent the body 1403 and pixels of the image 1402 that do not represent the body 1403 and a silhouette 1404 of the body produced therefrom.

Returning to FIG. 14A, the first 2D body image 1402-1 is processed to segment a plurality of pixels of the first 2D body image 1402-1 that represent the human body from a plurality of pixels of the first 2D body image 1402-1 that do not represent the human body, to produce a front silhouette 1404-1 of the human body. The second 2D body image 1402-2 is processed to segment a plurality of pixels of the second 2D body image 1402-2 that represent the human body from a plurality of pixels of the second 2D body image 1402-2 that do not represent the human body, to produce a first side silhouette 1404-2 of the human body. The third 2D body image 1402-3 is processed to segment a plurality of pixels of the third 2D body image 1402-3 that represent the human body from a plurality of pixels of the third 2D body image 1402-3 that do not represent the human body, to produce a back silhouette 1404-3 of the human body. The fourth 2D body image 1402-4 is processed to segment a plurality of pixels of the fourth 2D body image 1402-4 that represent the human body from a plurality of pixels of the fourth 2D body image 1402-4 that do not represent the human body, to produce a second side silhouette 1404-4 of the human body. Processing of the 2D body images 1402-1 through 1402-N to produce silhouettes 1404-1 through 1404-N from different orientations of the human body 1403 may be performed for any number of images 1402.

As discussed above with respect to FIG. 13, in some implementations, the silhouette may be segmented into different body segments by processing the pixels of the 2D image to determine a likelihood that the pixel corresponds to a segment label (e.g., hair, upper clothing, lower clothing, head, upper right arm, upper left leg, etc.).

In some implementations, in addition to generating a silhouette 1404 from the 2D body image 1402, the silhouette may be normalized in size and centered in the image. For example, the silhouette may be cropped by computing a bounding rectangle around the silhouette 1404. The silhouette 1404 may then be resized according to s, which is a function of a known height h of the user represented in the 2D body image 1402 (e.g., the height may be provided by the user):

$$s = h * \frac{0.8 * \text{image}_h}{\mu_h} \quad (1)$$

Where $\text{image}_h$ is the input image height, which may be based on the pixels of the image, and $\mu_h$ is the average height of a person (e.g., ~160 centimeters for females: ~176 centimeters for males).

Each silhouette 1404 representative of the body 1403 may then be processed to determine body traits or features of the human body. For example, different CNNs may be trained using silhouettes of bodies, such as human bodies, from different orientations with known features. In some implementations, different CNNs may be trained for different orientations. For example, a first CNN 1406A-1 may be trained to determine front view features from front view silhouettes 1404-1. A second CNN 1406A-2 may be trained to determine right side features from right side silhouettes. A third CNN 1406A-3 may be trained to determine back view features from back view silhouettes. A fourth CNN 1406A-4 may be trained to determine left side features from left side silhouettes. Different CNNs 1406A-1 through 1406A-N may be trained for each of the different orientations of silhouettes 1404-1 through 1404-N. Alternatively, one CNN may be trained to determine features from any orientation silhouette.

In implementations that utilize multiple images of the body 1403 to produce multiple sets of features, such as the example illustrated in FIG. 14A, those features may be concatenated, and the concatenated features processed together with a CNN to generate a set of personalized body features 1407. For example, a CNN may be trained to receive features generated from different silhouettes 1404 to produce personalized body features 1407. The personalized body features 1407 may indicate any aspect or information related to the body 1403 represented in the images 1402. For example, the personalized body features 1407 may indicate 3D joint locations, body volume, shape of the body, pose angles, neural network weights corresponding to the body, etc. In some implementations, the concatenated CNN 1406B may be trained to predict hundreds of personalized body features 1407 corresponding to the body 1403 represented in the images 1402.

Utilizing the personalized body features 1407, a body dimensions CNN 1470) processes the features and determines body dimensions 1472 for the body, as discussed further below. Likewise, a personalized 3D body model of the body is generated based on the personalized body features 1407. For example, the personalized body features 1407 may be provided to a body model, such as the SCAPE body model, the SMPL body model, etc., and the body model may generate the personalized 3D body model of the body 1403 represented in the images 1402 based on those personalized body features 1407.

In the illustrated example, personalized 3D model refinement 1408 may be performed to refine or revise the generated personalized 3D body model to better represent the body 1403 represented in the 2D body images 1402. For example, the personalized 3D body model may be compared to the body 1403 represented in one or more of the 2D body images 1402 to determine differences between the shape of the body 1403 represented in the 2D body image 1402 and the shape of the personalized 3D body model generated from the body features. In some implementations, the personalized 3D body model may be compared to a single image, such as image 1402-1. In other implementations, the personalized 3D body model may be compared to each of the 2D body images 1402-1 through 1402-N in parallel or sequentially. In still other implementations, one or more 2D model images may be generated from the personalized 3D body model and those 2D model images may be compared to the silhouettes and/or the 2D body images to determine differences between the 2D model images and the silhouette/2D body images.

Comparing the personalized 3D body model and/or a 2D model image with a 2D body image 1402 or silhouette 1404 may include determining an approximate pose of the body 1403 represented in the 2D body image and adjusting the personalized 3D body model to the approximate pose. The personalized 3D body model or rendered 2D model image may then be overlaid or otherwise compared to the body 1403 represented in the 2D body image 1402 and/or represented in the silhouette 1404 to determine a difference between the personalized 3D body model and the 2D body image.

Based on the determined differences between the personalized 3D body model and the body 1403 represented in the 2D body image 1402, the silhouette 1404 generated from that image may be refined to account for those differences. For example, if the personalized 3D body model is compared with the body 1403 represented in the first image 1402-1 and differences are determined, the silhouette 1404-1 may be refined based on those differences. Alternatively, the body features and/or the personalized 3D body model may be refined to account for those differences.

If a silhouette is refined as part of the personalized 3D model refinement 1408, the refined silhouette may be processed to determine refined features for the body 1403 represented in the 2D body image 1402 based on the refined silhouette. The refined features may then be concatenated with the features generated from the other silhouettes or with refined features generated from other refined silhouettes that were produced by the personalized 3D model refinement 1408. For example, the personalized 3D model refinement 1408 may compare the generated personalized 3D body model with the body 1403 as represented in two or more 2D body images 1402, such as a front image 1402-1 and a back image 1402-3, differences determined for each of those images, refined silhouettes generated from those differences and refined front view features and refined back view features generated. Those refined features may then be concatenated with the two side view features to produce refined body model features. In other implementations, personalized 3D model refinement 1408 may compare the personalized 3D body model with all views of the body 1403 represented in the 2D body images 1402 to determine differences and generate refined silhouettes for each of those 2D body images 1402-1 through 1402-N. Those refined silhouettes may then be processed by the CNNs 1406A-1 through 1406A-N to produce refined features and those refined features concatenated to produce refined body features 1407. Finally, the refined body features 1407 may be processed by personalized 3D modeling 1410 to generate a refined personalized 3D body model. This process of personalized 3D refinement may continue until there is no or limited difference (e.g., below a threshold difference) between the generated personalized 3D body model and the body 1403 represented in the 2D body images 1402.

In another implementation, personalized 3D model refinement 1408 may sequentially compare the personalized 3D body model with representations of the body 1403 in the different 2D body images 1402. For example, personalized 3D model refinement 1408 may compare the personalized 3D body model with a first representation of the body 1403 in a first 2D body image 1402-1 to determine differences that are then used to generate a refined silhouette 1404-1 corresponding to that first 2D body image 1402-1. The refined silhouette may then be processed to produce refined features and those refined features may be concatenated 1406B with the features generated from the other silhouettes 1404-2 through 1404-N to generate refined body features, which may be used to generate a refined personalized 3D body model. The refined personalized 3D body model may then be compared with a next image of the plurality of 2D body images 1402 to determine any differences and the process repeated. This process of personalized 3D refinement may continue until there is no or limited difference (e.g., below a threshold difference) between the generated personalized 3D body model and the body 1403 represented in the 2D body images 1402.

In some implementations, upon completion of personalized 3D model refinement 1408, the personalized 3D body model of the body represented in the 2D body images 1402 may be augmented with one or more textures, texture augmentation 1412, determined from one or more of the 2D body images 1402-1 through 1402-N. For example, the personalized 3D body model may be augmented to have a same or similar color to a skin color of the body 1403 represented the 2D body images 1402, clothing or clothing colors represented in the 2D body images 1402 may be used to augment the personalized 3D body model, facial features, hair, hair color, etc., of the body 1403 represented in the 2D body image 1402 may be determined and used to augment the personalized 3D body model.

Similar to personalized 3D model refinement, the approximate pose of the body in one of the 2D body images 1402 may be determined and the personalized 3D body model adjusted accordingly so that the texture obtained from that 2D body image 1402 may be aligned and used to augment that portion of the personalized 3D body model. In some implementations, alignment of the personalized 3D body model with the approximate pose of the body 1403 may be performed for each 2D body image 1402-1 through 1402-N so that texture information or data from the different views of the body 1403 represented in the different 2D body images 1402 may be used to augment the different poses of the resulting personalized 3D body model.

The result of the processing illustrated in the transition 1400 is a personalized 3D body model 1414 or avatar representative of the body of the user, that has been generated from 2D body images 1402 of the body 1403 of the user. In addition, determined body dimensions 1472 may be presented with the personalized 3D body model, as illustrated above.

Figure 14B:
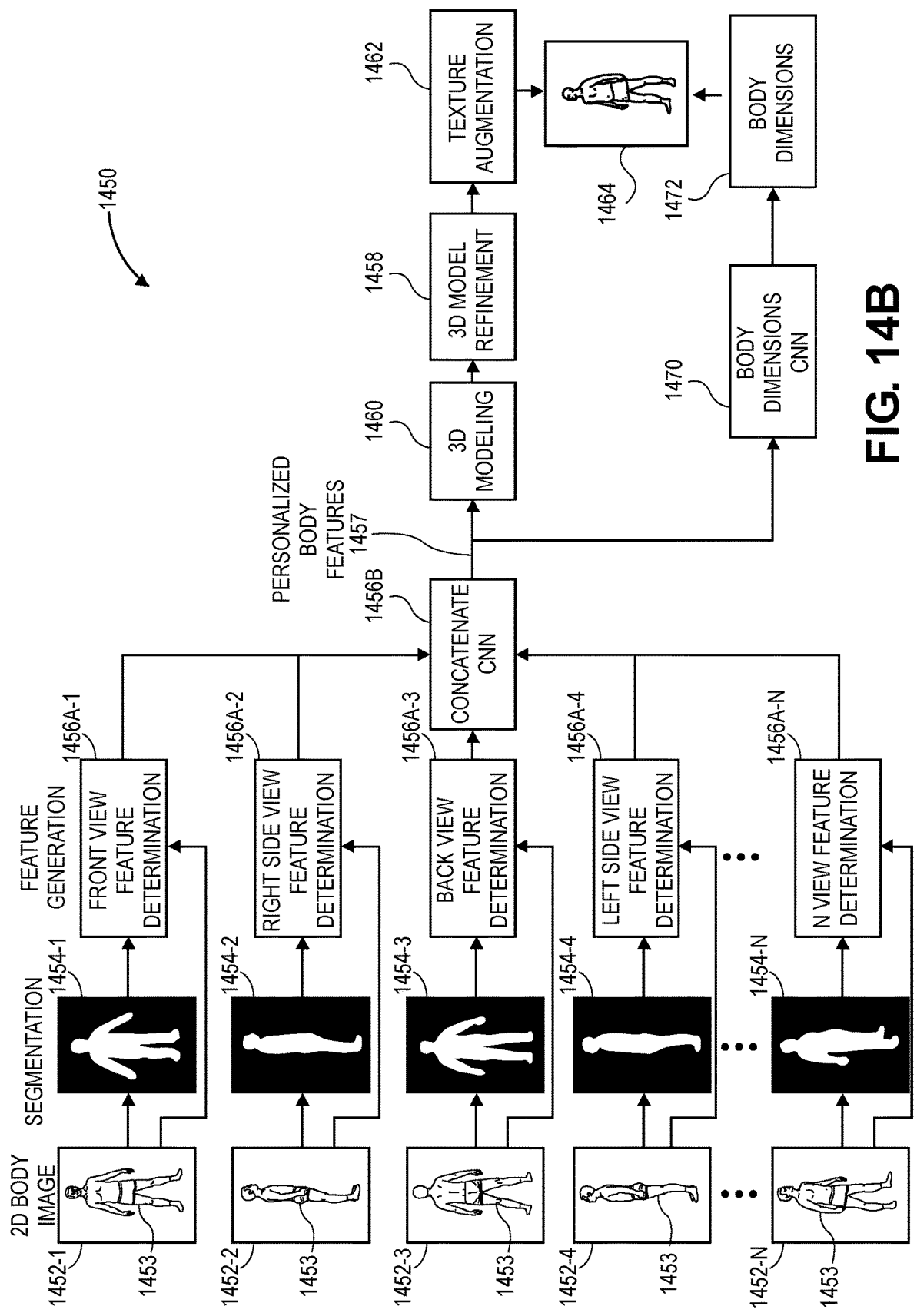
FIG. 14B is another transition diagram of processing two-dimensional body images to produce a personalized three-dimensional model of that body and corresponding body dimensions, in accordance with implementations of the present disclosure.

FIG. 14B is another transition diagram 1450 of processing 2D body images 1452 of a body to produce a personalized three-dimensional model of that body, in accordance with implementations of the present disclosure.

In some implementations, multiple 2D body images of a body from different views (e.g., front view, side view; back view; three-quarter view, etc.), such as 2D body images 1452-1, 1452-2, 1452-3, 1452-4 through 1452-N may be utilized with the disclosed implementations to generate a personalized 3D body model of the body. In the illustrated example, the first 2D body image 1452-1 is an image of a human body 1453 oriented in a front view facing a 2D imaging element. The second 2D body image 1452-2 is an image of the human body 1453 oriented in a first side view facing the 2D imaging element. The third 2D body image 1452-3 is an image of the human body 1453 oriented in a back view facing the 2D imaging element. The fourth 2D body image 1452-4 is an image of the human body 1453 oriented in a second side view facing the 2D imaging element. As will be appreciated, any number of 2D body images 1452-1 through 1452-N may be generated with the view of the human body 1453 in any number or orientations with respect to the 2D imaging element.

Each of the 2D body images 1452-1 through 1452-N are processed to segment pixels of the image that represent the human body 1453 from pixels of the image that do not represent the human body to produce a silhouette 1454 of the human body as represented in that image. Segmentation may be done through, for example, background subtraction, semantic segmentation, etc. In one example, a baseline image of the background may be known and used to subtract out pixels of the image that correspond to pixels of the baseline image, thereby leaving only foreground pixels that represent the human body. The background pixels may be assigned RGB color values for black (i.e., 0,0,0). The remaining pixels may be assigned RGB values for white (i.e., 255, 255, 255) to produce the silhouette 1454 or binary segmentation of the human body.

In another example, a CNN utilizing a semantic segmentation algorithm may be trained using images of human bodies, or simulated human bodies to train the CNN to distinguish between pixels that represent human bodies and pixels that do not represent human bodies. In such an example, the CNN may process the image 1452 and indicate or label pixels that represent the body (foreground) and pixels that do not represent the body (background). The background pixels may be assigned RGB color values for black (i.e., 0,0,0). The remaining pixels may be assigned RGB values for white (i.e., 255, 255, 255) to produce the silhouette or binary segmentation of the human body.

In other implementations, other forms or algorithms, such as edge detection, shape detection, etc., may be used to determine pixels of the image 1452 that represent the body 1453 and pixels of the image 1452 that do not represent the body 1453 and a silhouette 1454 of the body produced therefrom.

Returning to FIG. 14B, the first 2D body image 1452-1 is processed to segment a plurality of pixels of the first 2D body image 1452-1 that represent the human body from a plurality of pixels of the first 2D body image 1452-1 that do not represent the human body, to produce a front silhouette 1454-1 of the human body. The second 2D body image 1452-2 is processed to segment a plurality of pixels of the second 2D body image 1452-2 that represent the human body from a plurality of pixels of the second 2D body image 1452-2 that do not represent the human body, to produce a first side silhouette 1454-2 of the human body. The third 2D body image 1452-3 is processed to segment a plurality of pixels of the third 2D body image 1452-3 that represent the human body from a plurality of pixels of the third 2D body image 1452-3 that do not represent the human body, to produce a back silhouette 1454-3 of the human body. The fourth 2D body image 1452-4 is processed to segment a plurality of pixels of the fourth 2D body image 1452-4 that represent the human body from a plurality of pixels of the fourth 2D body image 1452-4 that do not represent the human body, to produce a second side silhouette 1454-4 of the human body. Processing of the 2D body images 1452-1 through 1452-N to produce silhouettes 1454-1 through 1454-N from different orientations of the human body 1453 may be performed for any number of images 1452.

As discussed above with respect to FIG. 13, in some implementations, the silhouette may be segmented into different body segments by processing the pixels of the 2D image to determine a likelihood that the pixel corresponds to a segment label (e.g., hair, upper clothing, lower clothing, head, upper right arm, upper left leg, etc.).

Similar to FIG. 14A, in some implementations, in addition to generating a silhouette 1454 from the 2D body image 1452, the silhouette may be normalized in size and centered in the image.

Each silhouette 1454 representative of the body 1453 may then be processed to determine body traits or features of the human body. For example, different CNNs may be trained using silhouettes of bodies, such as human bodies, from different orientations with known features. In some implementations, different CNNs may be trained for different orientations. For example, a first CNN 1456A-1 may be trained to determine front view features from front view silhouettes 1454-1. A second CNN 1456A-2 may be trained to determine right side features from right side silhouettes 1454-2. A third CNN 1456A-3 may be trained to determine back view features from back view silhouettes 1454-3. A fourth CNN 1456A-4 may be trained to determine left side features from left side silhouettes 1454-4. Different CNNs 1456A-1 through 1456A-N may be trained for each of the different orientations of silhouettes 1454-1 through 1454-N. Alternatively, one CNN may be trained to determine features from any orientation silhouette.

In some implementations, the same or different CNNs may also utilize the 2D body image 1452 as an input to the CNN that is used to generate and determine the body features. For example, the first CNN 1456A-1 may be trained to determine front view features based on inputs of the front view silhouettes 1454-1 and/or the 2D body image 1452-1. The second CNN 1456A-2 may be trained to determine right side features from right side silhouettes 1454-2 and/or the right side 2D body image 1452-2. The third CNN 1456A-3 may be trained to determine back view features from back view silhouettes 1454-3 and/or the back view 2D body image 1452-3. The fourth CNN 1456A-4 may be trained to determine left side features from left side silhouettes 1454-4 and/or the left side 2D body image 1452-4. Different CNNs 1456A-1 through 1456A-N may be trained for each of the different orientations of silhouettes 1454-1 through 1454-N and/or 2D body images 1452-1 through 1452-N.

In still other implementations, different CNNs may be trained for each of the silhouettes 1454 and the 2D body images 1452. For example, the first CNN 1456A-1 may be trained to determine front view features from the silhouette 1454-1 and another front view CNN may be trained to determine front view features from the 2D body image 1452-1. The second CNN 1456A-2 may be trained to determine right side view features from the silhouette 1454-2 and another right side view CNN may be trained to determine right side view features from the 2D body image 1452-2. The third CNN 1456A-3 may be trained to determine back view features from the silhouette 1454-3 and another back view CNN may be trained to determine back view features from the 2D body image 1452-3. The fourth CNN 1456A-4 may be trained to determine left side view features from the silhouette 1454-4 and another left side view CNN may be trained to determine left side view features from the 2D body image 1452-4.

In implementations that utilize multiple images of the body 1453 and/or multiple silhouettes to produce multiple sets of features, such as the example illustrated in FIG. 14B, those features may be concatenated CNN 1456B and the concatenated features processed together with a CNN to generate a set of personalized body features 1457. For example, a CNN may be trained to receive features generated from different silhouettes 1454, features generated from different 2D body images 1452, and/or features generated by a CNN that processes both silhouettes 1454 and the 2D body images 1452 to produce personalized body features 1457. The personalized body features 1457 may indicate any aspect or information related to the body 1453 represented in the images 1452. For example, the personalized body features 1457 may indicate 3D joint locations, body volume, shape of the body, pose angles, neural network weights corresponding to the body, etc. In some implementations, the concatenated CNN 1456B may be trained to predict hundreds of personalized body features 1457 corresponding to the body 1453 represented in the images 1452.

Utilizing the personalized body features 1457, a body dimensions CNN 1470) processes the features and determines body dimensions 1472 for the body, as discussed further below. Likewise, a personalized 3D body model of the body is generated based on the personalized body features 1457. For example, the personalized body features 1457 may be provided to a body model, such as the SCAPE body model, the SMPL body model, etc., and the body model may generate the personalized 3D body model of the body 1453 represented in the images 1452 based on those personalized body features 1457.

In the illustrated example, personalized 3D model refinement 1458 may be performed to refine or revise the generated personalized 3D body model to better represent the body 1453 represented in the 2D body images 1452. For example, as discussed above, the personalized 3D body model may be compared to the body 1453 represented in one or more of the 2D body images 1452 to determine differences between the shape of the body 1453 represented in the 2D body image 1452 and the shape of the personalized 3D body model generated from the body features. In some implementations, the personalized 3D body model may be compared to a single image, such as image 1452-1. In other implementations, the personalized 3D body model may be compared to each of the 2D body images 1452-1 through 1452-N in parallel or sequentially. In still other implementations, one or more 2D model images may be generated from the personalized 3D body model and those 2D model images may be compared to the silhouettes 1454 and/or the 2D body images 1452 to determine differences between the 2D model images and the silhouette/2D body images.

Comparing the personalized 3D body model and/or a 2D model image with a 2D body image 1452 or silhouette 1454 may include determining an approximate pose of the body 1453 represented in the 2D body image and adjusting the personalized 3D body model to the approximate pose. The personalized 3D body model or rendered 2D model image may then be overlaid or otherwise compared to the body 1453 represented in the 2D body image 1452 and/or represented in the silhouette 1454 to determine a difference between the personalized 3D body model image and the 2D body image/silhouette.

Based on the determined differences between the personalized 3D body model and the body 1453 represented in the 2D body image 1452, the silhouette 1454 generated from that image may be refined to account for those differences. Alternatively, the body features and/or the personalized 3D body model may be refined to account for those differences.

In some implementations, upon completion of personalized 3D model refinement 1458, the personalized 3D body model of the body represented in the 2D body images 1452 may be augmented with one or more textures, texture augmentation 1462, determined from one or more of the 2D body images 1452-1 through 1452-N. For example, the personalized 3D body model may be augmented to have a same or similar color to a skin color of the body 1453 represented the 2D body images 1452, clothing or clothing colors represented in the 2D body images 1452 may be used to augment the personalized 3D body model, facial features, hair, hair color, etc., of the body 1453 represented in the 2D body image 1452 may be determined and used to augment the personalized 3D body model.

Similar to personalized 3D model refinement, the approximate pose of the body in one of the 2D body images 1452 may be determined and the personalized 3D body model adjusted accordingly so that the texture obtained from that 2D body image 1452 may be aligned and used to augment that portion of the personalized 3D body model. In some implementations, alignment of the personalized 3D body model with the approximate pose of the body 1453 may be performed for each 2D body image 1452-1 through 1452-N so that texture information or data from the different views of the body 1453 represented in the different 2D body images 1452 may be used to augment the different poses of the resulting personalized 3D body model.

The result of the processing illustrated in the transition 1450 is a personalized 3D body model 1464 or avatar representative of the body of the user, that has been generated from 2D body images 1452 of the body 1453 of the user. In addition, determined body dimensions 1472 may be presented with the personalized 3D body model, as illustrated above.

As discussed above, features or objects expressed in imaging data, such as human bodies, colors, textures or outlines of the features or objects, may be extracted from the data in any number of ways. For example, colors of pixels, or of groups of pixels, in a digital image may be determined and quantified according to one or more standards, e.g., the RGB color model, in which the portions of red, green or blue in a pixel are expressed in three corresponding numbers ranging from 0 to 255 in value, or a hexadecimal model, in which a color of a pixel is expressed in a six-character code, wherein each of the characters may have a range of sixteen. Moreover, textures or features of objects expressed in a digital image may be identified using one or more computer-based methods, such as by identifying changes in intensities within regions or sectors of the image, or by defining areas of an image corresponding to specific surfaces.

Furthermore, edges, contours, outlines, colors, textures, silhouettes, shapes or other characteristics of objects, or portions of objects, expressed in images may be identified using one or more algorithms or machine-learning tools. The objects or portions of objects may be identified at single, finite periods of time, or over one or more periods or durations. Such algorithms or tools may be directed to recognizing and marking transitions (e.g., the edges, contours, outlines, colors, textures, silhouettes, shapes or other characteristics of objects or portions thereof) within the digital images as closely as possible, and in a manner that minimizes noise and disruptions, and does not create false transitions. Some detection algorithms or techniques that may be utilized in order to recognize characteristics of objects or portions thereof in digital images in accordance with the present disclosure include, but are not limited to, Canny edge detectors or algorithms; Sobel operators, algorithms or filters; Kayyali operators; Roberts edge detection algorithms; Prewitt operators; Frei-Chen methods; semantic segmentation algorithms; background subtraction; or any other algorithms or techniques that may be known to those of ordinary skill in the pertinent arts.

Image processing algorithms, other machine learning algorithms or CNNs may be operated on computer devices of various sizes or types, including but not limited to smartphones or other cell phones, tablets, video cameras or other computer-based machines. Such mobile devices may have limited available computer resources, e.g., network bandwidth, storage capacity or processing power, as compared to larger or more complex computer devices. Therefore, executing computer vision algorithms, other machine learning algorithms, or CNNs on such devices may occupy all or much of the available resources, without any guarantee, or even a reasonable assurance, that the execution of such algorithms will be successful. For example, processing digital 2D body images captured by a user of a portable device (e.g., smartphone, tablet, laptop, webcam) according to one or more algorithms in order to produce a personalized 3D body model from the digital images may be an ineffective use of the limited resources that are available on the smartphone or tablet. Accordingly, in some implementations, as discussed herein, some or all of the processing may be performed by one or more computing resources that are remote from the portable device. In some implementations, initial processing of the images to generate binary segmented silhouettes may be performed on the device. Subsequent processing to generate and refine the personalized 3D body model may be performed on one or more remote computing resources. For example, the silhouettes may be sent from the portable device to the remote computing resources for further processing. Still further, in some implementations, texture augmentation of the personalized 3D body model of the body may be performed on the portable device or remotely.

In some implementations, to increase privacy of the user, only the binary segmented silhouette may be sent from the device for processing on the remote computing resources and the original 2D images that include the representation of the user may be maintained locally on the portable device. In such an example, the rendered personalized 3D body model and body dimensions may be sent back to the device and the device may perform texture augmentation of the received personalized 3D body model based on those images. Utilizing such a distributed computing arrangement retains user identifiable information on the portable device of the user while at the same time leveraging the increased computing capacity available at remote computing resources.

Machine learning tools, such as artificial neural networks, have been utilized to identify relations between respective elements of apparently unrelated sets of data. An artificial neural network, such as CNN, is a parallel distributed computing processor comprised of individual units that may collectively learn and store experimental knowledge and make such knowledge available for use in one or more applications. Such a network may simulate the non-linear mental performance of the many neurons of the human brain in multiple layers by acquiring knowledge from an environment through one or more flexible learning processes, determining the strengths of the respective connections between such neurons, and utilizing such strengths when storing acquired knowledge. Like the human brain, an artificial neural network may use any number of neurons in any number of layers, including an input layer, an output layer, and one or more intervening hidden layers. In view of their versatility, and their inherent mimicking of the human brain, machine learning tools including not only artificial neural networks but also nearest neighbor methods or analyses, factorization methods or techniques, K-means clustering analyses or techniques, similarity measures such as log likelihood similarities or cosine similarities, latent Dirichlet allocations or other topic models, or latent semantic analyses have been utilized in image processing applications.

Artificial neural networks may be trained to map inputted data to desired outputs by adjusting the strengths of the connections between one or more neurons, which are sometimes called synaptic weights. An artificial neural network may have any number of layers, including an input layer, an output layer, and any number of intervening hidden layers. Each of the neurons in a layer within a neural network may receive one or more inputs and generate one or more outputs in accordance with an activation or energy function, with features corresponding to the various strengths or synaptic weights. Likewise, each of the neurons within a network may be understood to have different activation or energy functions; in this regard, such a network may be dubbed a heterogeneous neural network. In some neural networks, at least one of the activation or energy functions may take the form of a sigmoid function, wherein an output thereof may have a range of zero to one or 0 to 1. In other neural networks, at least one of the activation or energy functions may take the form of a hyperbolic tangent function, wherein an output thereof may have a range of negative one to positive one, or −1 to +1. Thus, the training of a neural network according to an identity function results in the redefinition or adjustment of the strengths or weights of such connections between neurons in the various layers of the neural network, in order to provide an output that most closely approximates or associates with the input to the maximum practicable extent.

Artificial neural networks may typically be characterized as either feedforward neural networks or recurrent neural networks and may be fully or partially connected. In a feedforward neural network, e.g., a convolutional neural network, information specifically flows in one direction from an input layer to an output layer, while in a recurrent neural network, at least one feedback loop returns information regarding the difference between the actual output and the targeted output for training purposes. Additionally, in a fully connected neural network architecture, each of the neurons in one of the layers is connected to all of the neurons in a subsequent layer. By contrast, in a sparsely connected neural network architecture, the number of activations of each of the neurons is limited, such as by a sparsity parameter.

Moreover, the training of a neural network is typically characterized as supervised or unsupervised. In supervised learning, a training set comprises at least one input and at least one target output for the input. Thus, the neural network is trained to identify the target output, to within an acceptable level of error. In unsupervised learning of an identity function, such as that which is typically performed by a sparse autoencoder, target output of the training set is the input, and the neural network is trained to recognize the input as such. Sparse autoencoders employ backpropagation in order to train the autoencoders to recognize an approximation of an identity function for an input, or to otherwise approximate the input. Such backpropagation algorithms may operate according to methods of steepest descent, conjugate gradient methods, or other like methods or techniques, in accordance with the systems and methods of the present disclosure. Those of ordinary skill in the pertinent art would recognize that any algorithm or method may be used to train one or more layers of a neural network. Likewise, any algorithm or method may be used to determine and minimize the error in an output of such a network. Additionally, those of ordinary skill in the pertinent art would further recognize that the various layers of a neural network may be trained collectively, such as in a sparse autoencoder, or individually, such that each output from one hidden layer of the neural network acts as an input to a subsequent hidden layer.

Once a neural network has been trained to recognize dominant characteristics of an input of a training set, e.g., to associate an image with a label, a category, a cluster or a pseudolabel thereof, to within an acceptable tolerance, an input and/or multiple inputs, in the form of an image, silhouette, features, known traits corresponding to the image, etc., may be provided to the trained network, and an output generated therefrom. For example, the CNN discussed above may receive as inputs a generated silhouette and one or more body attributes (e.g., height, weight, gender) corresponding to the body represented by the silhouette. The trained CNN may then produce as outputs the predicted features corresponding to those inputs.

Figure 15:
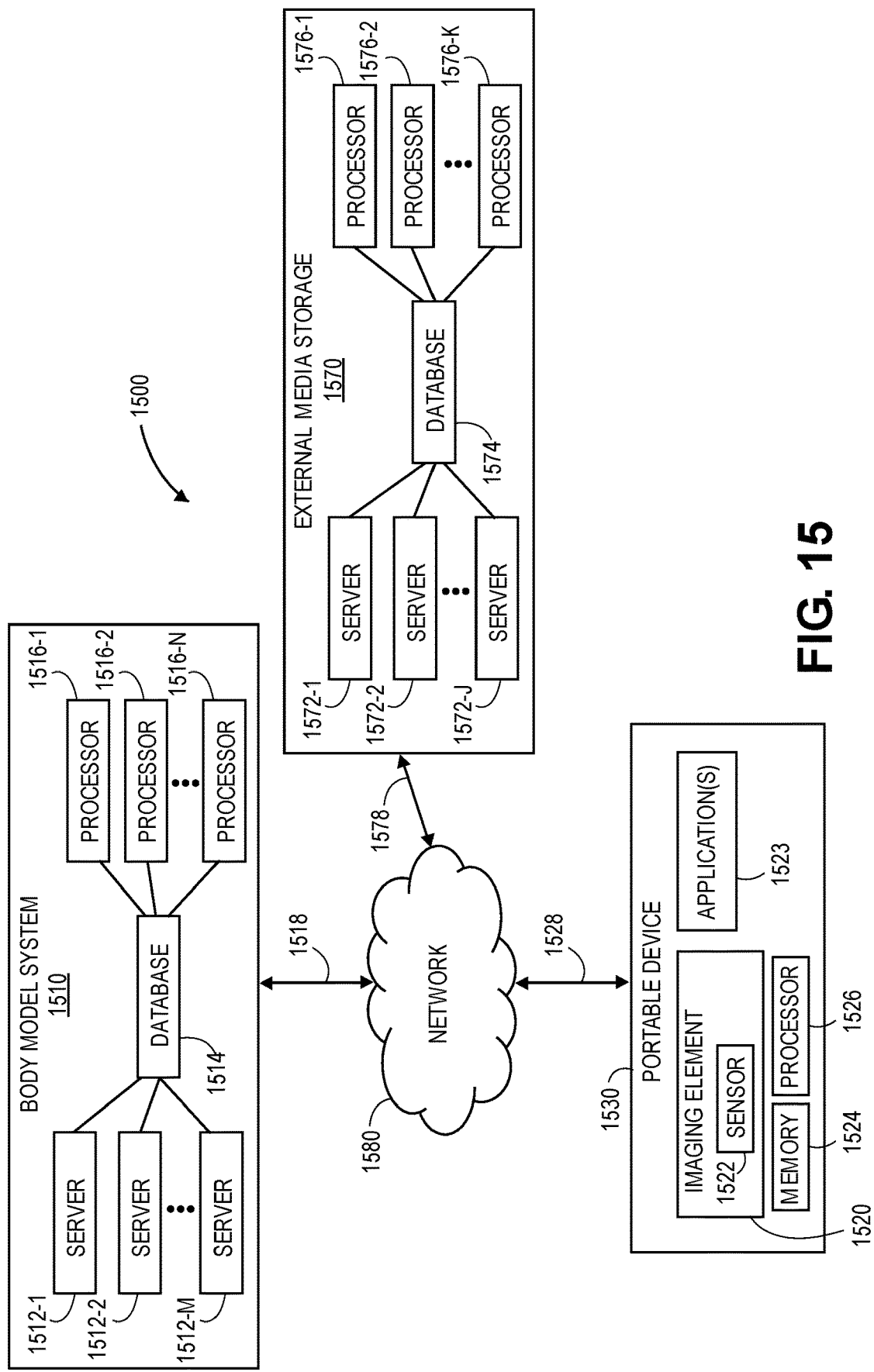
FIG. 15 is a block diagram of components of an image processing system, in accordance with implementations of the present disclosure.

Referring to FIG. 15, a block diagram of components of one image processing system 1500 in accordance with implementations of the present disclosure is shown.

The system 1500 of FIG. 15 includes a body model system 1510, an imaging element 1520 that is part of a portable device 1530 of a user, such as a tablet, a laptop, a cellular phone, a webcam, etc., and an external media storage facility 1570 connected to one another across a network 1580, such as the Internet.

The body model system 1510 of FIG. 15 includes M physical computer servers 1512-1, 1512-2 . . . 1512-M having one or more databases (or data stores) 1514 associated therewith, as well as N computer processors 1516-1, 1516-2 . . . 1516-N provided for any specific or general purpose. For example, the body model system 1510 of FIG. 15 may be independently provided for the exclusive purpose of generating personalized 3D body models, body dimensions, and/or body measurements from 2D body images captured by imaging elements, such as imaging element 1520, or silhouettes produced therefrom, or alternatively, provided in connection with one or more physical or virtual services configured to manage or monitor such information, as well as one or more other functions. The servers 1512-1, 1512-2 . . . 1512-M may be connected to or otherwise communicate with the databases 1514 and the processors 1516-1, 1516-2 . . . 1516-N. The databases 1514 may store any type of information or data, including simulated silhouettes, body features, simulated 3D body models, etc. The servers 1512-1, 1512-2 . . . 1512-M and/or the computer processors 1516-1, 1516-2 . . . 1516-N may also connect to or otherwise communicate with the network 1580, as indicated by line 1518, through the sending and receiving of digital data.

The imaging element 1520 may comprise any form of optical recording sensor or device that may be used to photograph or otherwise record information or data regarding a body of the user, or for any other purpose. As is shown in FIG. 15, the portable device 1530 that includes the imaging element 1520 is connected to the network 1580 and includes one or more sensors 1522, one or more memory or storage components 1524 (e.g., a database or another data store), one or more processors 1526, and any other components that may be required in order to capture, analyze and/or store imaging data, such as the 2D body images discussed herein. For example, the imaging element 1520 may capture one or more still or moving images and may also connect to or otherwise communicate with the network 1580, as indicated by the line 1528, through the sending and receiving of digital data. Although the system 1500 shown in FIG. 15 includes just one imaging element 1520 therein, any number or type of imaging elements, portable devices, or sensors may be provided within any number of environments in accordance with the present disclosure.

The portable device 1530 may be used in any location and any environment to generate 2D body images that represent a body of the user. In some implementations, the portable device may be positioned such that it is stationary and approximately vertical (within approximately ten-degrees of vertical) and the user may position their body within a field of view of the imaging element 1520 of the portable device 1530 at different orientations so that the imaging element 1520 of the portable device may generate 2D body images that include a representation of the body of the user from different orientations.

The portable device 1530 may also include one or more applications 1523 stored in memory 1524 that may be executed by the processor 1526 of the portable device to cause the processor of the portable device to perform various functions or actions. For example, when executed, the application 1523 may provide instructions to a user regarding placement of the portable device 1530, positioning of the body of the user within the field of view of the imaging element 1520 of the portable device, orientation of the body of the user, etc. Likewise, in some implementations, the application 1523 may present a personalized 3D body model, body dimensions, and/or body measurements determined and generated from the 2D body images in accordance with the described implementations, to the user and allow the user to interact with the personalized 3D body model. For example, a user may rotate the personalized 3D body model to view different angles of the personalized 3D body model, view accurate body dimensions determined from the 2D images, view body measurements, such as body fat, body mass, body volume, etc. Likewise, in some implementations, the personalized 3D body model may be modified by request of the user to simulate what the body of the user may look like under certain conditions, such as loss of weight, gain of muscle, etc.

The external media storage facility 1570 may be any facility, station or location having the ability or capacity to receive and store information or data, such as silhouettes, simulated or rendered personalized 3D body models of bodies, textures, body dimensions, etc., received from the body model system 1510, and/or from the portable device 1530. As is shown in FIG. 15, the external media storage facility 1570 includes J physical computer servers 1572-1, 1572-2 . . . 1572-J having one or more databases 1574 associated therewith, as well as K computer processors 1576-1, 1576-2 . . . 1576-K. The servers 1572-1, 1572-2 . . . 1572-J may be connected to or otherwise communicate with the databases 1574 and the processors 1576-1, 1576-2 . . . 1576-K. The databases 1574 may store any type of information or data, including digital images, silhouettes, personalized 3D body models, etc. The servers 1572-1, 1572-2 . . . 1572-J and/or the computer processors 1576-1, 1576-2 . . . 1576-K may also connect to or otherwise communicate with the network 1580, as indicated by line 1578, through the sending and receiving of digital data.

The network 1580 may be any wired network, wireless network, or combination thereof, and may comprise the Internet in whole or in part. In addition, the network 1580 may be a personal area network, local area network, wide area network, cable network, satellite network, cellular telephone network, or combination thereof. The network 1580 may also be a publicly accessible network of linked networks, possibly operated by various distinct parties, such as the Internet. In some implementations, the network 1580 may be a private or semi-private network, such as a corporate or university intranet. The network 1580 may include one or more wireless networks, such as a Global System for Mobile Communications (GSM) network, a Code Division Multiple Access (CDMA) network, a Long Term Evolution (LTE) network, or some other type of wireless network. Protocols and components for communicating via the Internet or any of the other aforementioned types of communication networks are well known to those skilled in the art of computer communications and thus, need not be described in more detail herein.

The computers, servers, devices and the like described herein have the necessary electronics, software, memory, storage, databases, firmware, logic/state machines, microprocessors, communication links, displays or other visual or audio user interfaces, printing devices, and any other input/output interfaces to provide any of the functions or services described herein and/or achieve the results described herein. Also, those of ordinary skill in the pertinent art will recognize that users of such computers, servers, devices and the like may operate a keyboard, keypad, mouse, stylus, touch screen, or other device (not shown) or method to interact with the computers, servers, devices and the like, or to "select" an item, link, node, hub or any other aspect of the present disclosure.

The body model system 1510, the portable device 1530 or the external media storage facility 1570 may use any web-enabled or Internet applications or features, or any other client-server applications or features including E-mail or other messaging techniques, to connect to the network 1580, or to communicate with one another, such as through short or multimedia messaging service (SMS or MMS) text messages. For example, the servers 1512-1, 1512-2 . . . 1512-M may be adapted to transmit information or data in the form of synchronous or asynchronous messages from the body model system 1510 to the processor 1526 or other components of the portable device 1530, or any other computer device in real time or in near-real time, or in one or more offline processes, via the network 1580. Those of ordinary skill in the pertinent art would recognize that the body model system 1510, the portable device 1530 or the external media storage facility 1570 may operate any of a number of computing devices that are capable of communicating over the network, including but not limited to set-top boxes, personal digital assistants, digital media players, web pads, laptop computers, desktop computers, electronic book readers, cellular phones, and the like. The protocols and components for providing communication between such devices are well known to those skilled in the art of computer communications and need not be described in more detail herein.

The data and/or computer executable instructions, programs, firmware, software and the like (also referred to herein as "computer executable" components) described herein may be stored on a computer-readable medium that is within or accessible by computers or computer components such as the servers 1512-1, 1512-2 . . . 1512-M, the processor 1526, the servers 1572-1, 1572-2 . . . 1572-J, or any other computers or control systems utilized by the body model system 1510, the portable device 1530, applications 1523, or the external media storage facility 1570, and having sequences of instructions which, when executed by a processor (e.g., a central processing unit, or "CPU"), cause the processor to perform all or a portion of the functions, services and/or methods described herein. Such computer executable instructions, programs, software and the like may be loaded into the memory of one or more computers using a drive mechanism associated with the computer-readable medium, such as a floppy drive, CD-ROM drive, DVD-ROM drive, network interface, or the like, or via external connections.

Some implementations of the systems and methods of the present disclosure may also be provided as a computer-executable program product including a non-transitory machine-readable storage medium having stored thereon instructions (in compressed or uncompressed form) that may be used to program a computer (or other electronic device) to perform processes or methods described herein. The machine-readable storage media of the present disclosure may include, but is not limited to, hard drives, floppy diskettes, optical disks, CD-ROMs, DVDs, ROMs, RAMs, erasable programmable ROMs ("EPROM"), electrically erasable programmable ROMs ("EEPROM"), flash memory, magnetic or optical cards, solid-state memory devices, or other types of media/machine-readable medium that may be suitable for storing electronic instructions. Further, implementations may also be provided as a computer executable program product that includes a transitory machine-readable signal (in compressed or uncompressed form). Examples of machine-readable signals, whether modulated using a carrier or not, may include, but are not limited to, signals that a computer system or machine hosting or running a computer program can be configured to access, or including signals that may be downloaded through the Internet or other networks.

Figure 16:
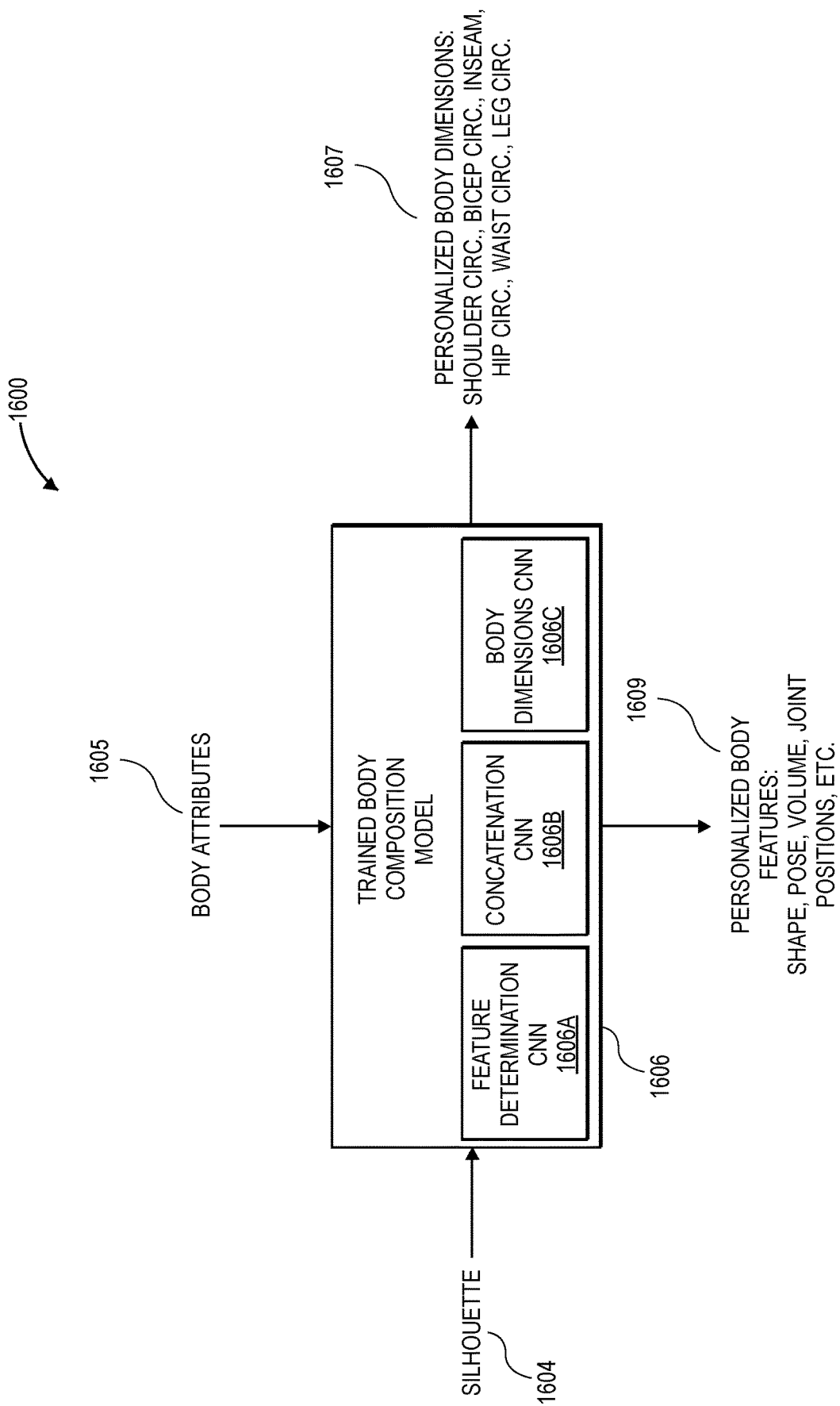
FIG. 16 is a block diagram of a trained body composition model that determines body dimensions of a body represented in two-dimensional body images, in accordance with implementations of the present disclosure.

FIG. 16 is a block diagram of a trained body composition model 1600 that determines body features 1609 and body dimensions 1607 of a body represented in two-dimensional images, in accordance with implementations of the present disclosure. As discussed above, the model 1600 may be a neural network, such as a CNN that is trained to receive one or more inputs that are processed to generate one or more outputs, such as the body features 1609 and body dimensions 1607. In the illustrated example, the trained body composition model 1606 may include several component CNNs that receive different inputs and provide different outputs. Likewise, outputs from one of the component CNNs may be provided as an input to one or more other component CNNs of the trained body composition model. For example, the trained body composition model may include three parts of component CNNs. In one implementation, a first component part may include one or more feature determination CNNs 1606A and a second component part may include a concatenation CNN 1606B. The third part may be a body dimensions CNN 1606C. In the illustrated example, there may be different feature determination CNNs 1606A for each of the different body orientations (e.g., front view, right side view, back view, left side view, three-quarter view), different silhouettes 1604 corresponding to those different body orientations, and/or different 2D body images corresponding to those different body orientations, each CNN trained for inputs having the particular orientation. Likewise, in some implementations, the feature determination CNNs 1606A may receive multiple different types of inputs. For example, in addition to receiving a silhouette 1604 and/or 2D body image, each feature determination CNN 1606A may receive one or more body attributes 1605 corresponding to the body represented by the silhouettes 1604 and/or 2D body images. The body attributes 1605 may include, but are not limited to, height, weight, gender, etc. As discussed, the trained feature determination CNNs 1606A may process the inputs and generate features representative of the bodies represented in the 2D body images that were used to produce the silhouettes 1604. For example, if there are four silhouettes, one for a front view; one for a right side view, one for a back view, and one for a left side view, the four feature determination CNNs 1606A trained for those views each produce a set of features representative of the body represented in the 2D body image used to generate the silhouette.

Utilizing binary silhouettes 1604 of bodies improves the accuracy of the feature determination CNN 1606A as it can focus purely on size, shape, etc. of the body, devoid of any other aspects (e.g., color, clothing, hair, etc.). In other implementations, the use of the 2D body images in conjunction with or independent of the silhouettes provides additional data, such as shadows, skin tone, etc., that the feature determination CNN 1606A may utilize in determining and producing a set of features representative of the body represented in the 2D body image.

The features output from the feature determination CNNs 1606A, in the disclosed implementation, are received as inputs to the concatenation CNN 1606B. Likewise, in some implementations, the concatenation CNN 1606B may be trained to receive other inputs, such as body attributes 1605.

As discussed, the concatenation CNN 1606B may be trained to receive the inputs of features, and optionally other inputs, produce concatenated features, and produce as outputs a set of body features 1609 corresponding to the body represented in the 2D body images. In some implementations, the body features may include hundreds of features, including, but not limited to, shape, pose, volume, joint position, etc., of the represented body.

The body dimensions CNN 1606C, which may be trained using real and/or synthetic data, as discussed further below, may receive as inputs the outputs from the concatenation CNN 1606B, and optionally other inputs, and process those inputs to determine one or more body dimensions 1607 for the body represented in the input silhouette 1604.

Figure 17:
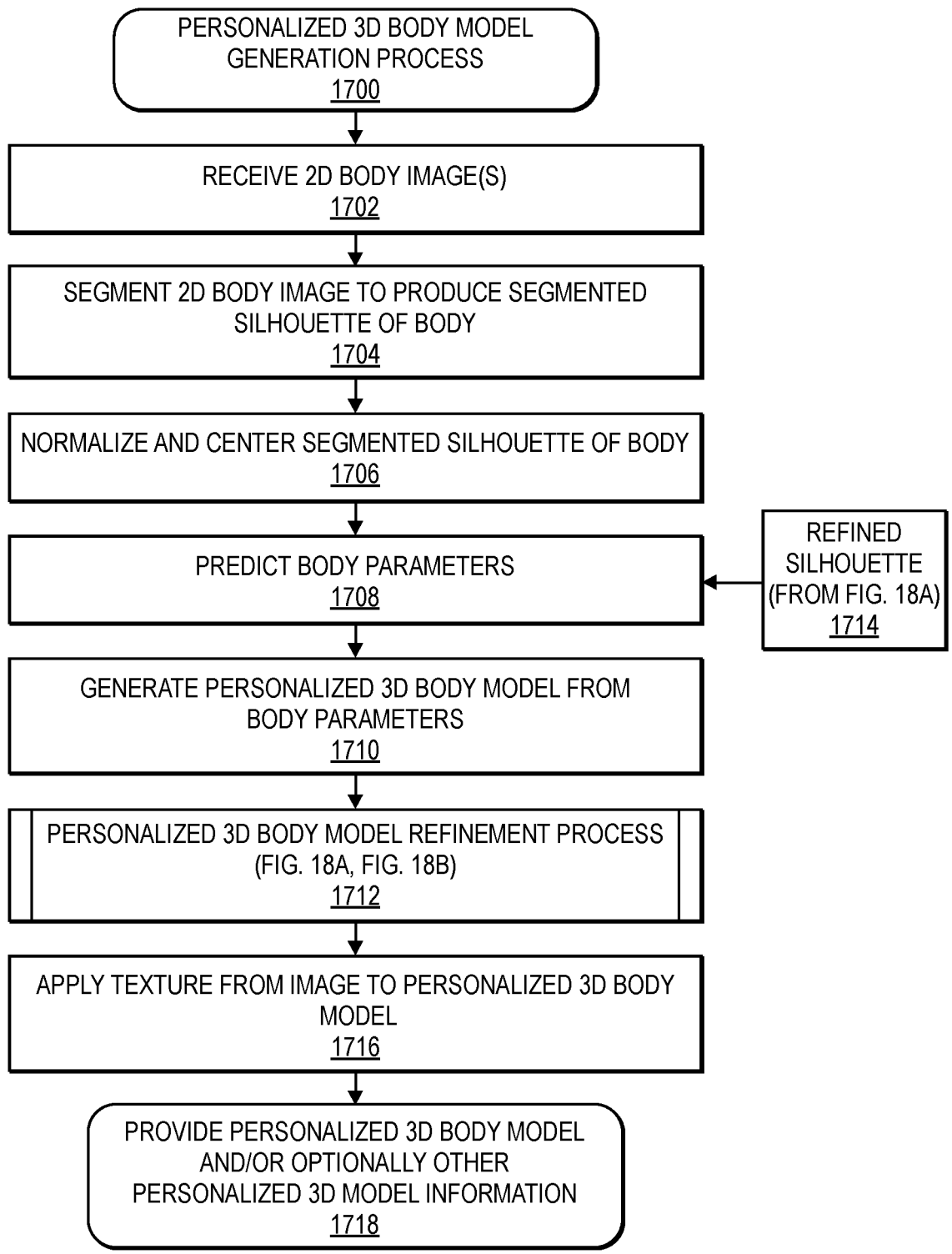
FIG. 17 is an example flow diagram of a three-dimensional body model generation process, in accordance with implementations of the present disclosure.

FIG. 17 is an example flow diagram of a personalized 3D body model generation process 1700, in accordance with implementations of the present disclosure.

The example process 1700 begins upon receipt of one or more 2D body images of a body, as in 1702. As noted above, the disclosed implementations are operable with any number of 2D body images for use in generating a personalized 3D body model of that body. For example, in some implementations, a single 2D body image may be used. In other implementations, two, three, four, or more 2D body images may be used.

As discussed above, the 2D body images may be generated using any 2D imaging element, such as a camera on a portable device, a webcam, etc. The received 2D body images are then segmented to produce a binary silhouette of the body represented in the one or more 2D body images, as in 1704. As discussed above, one or more segmentation techniques, such as background subtraction, semantic segmentation, Canny edge detectors or algorithms, Sobel operators, algorithms or filters, Kayyali operators, Roberts edge detection algorithms, Prewitt operators, Frei-Chen methods, or any other algorithms or techniques that may be known to those of ordinary skill in the pertinent arts. In some implementations, the silhouette may be further segmented into body segments.

In addition, in some implementations, the silhouettes may be normalized in height and centered in the image before further processing, as in 1706. For example, the silhouettes may be normalized to a standard height based on a function of a known or provided height of the body of the user represented in the image and an average height (e.g., average height of female body, average height of male body). In some implementations, the average height may be more specific than just gender. For example, the average height may be the average height of a gender and a race corresponding to the body, or a gender and a location (e.g., United States) of the user, etc.

The normalized and centered silhouette may then be processed by one or more neural networks, such as one or more CNNs as discussed above, to generate body parameters representative of the body represented in the 2D body images, as in 1708. As discussed above, there may be multiple steps involved in body parameter prediction. For example, each silhouette may be processed using CNNs trained for the respective orientation of the silhouette to generate sets of features of the body as determined from the silhouette. The sets of features generated from the different silhouette may then be processed using a neural network, such as a CNN, to concatenate the features and generate the body parameters representative of the body represented in the 2D body images.

The body parameters may then be provided to one or more body models, such as an SMPL body model or a SCAPE body model and the body model may generate a personalized 3D body model for the body represented in the 2D body images, as in 1710. In addition, in some implementations, the personalized 3D body model may be refined, if necessary, to more closely correspond to the actual image of the body of the user, as in 1800. Personalized 3D body model refinement is discussed above and discussed further below with respect FIGS. 18A and 18B.

As discussed below, the personalized 3D body model refinement process 1800 (FIG. 18A) returns a refined silhouette, as in 1714. Upon receipt of the refined silhouette, the example process 1700 again generates body parameters, as in 1708, and continues. This may be done until no further refinements are to be made to the silhouette. In comparison, the personalized 3D body model refinement process 1850 (FIG. 18B) generates and returns a refined personalized 3D body model and the example process 1700 continues at block 1716.

Figure 18A:
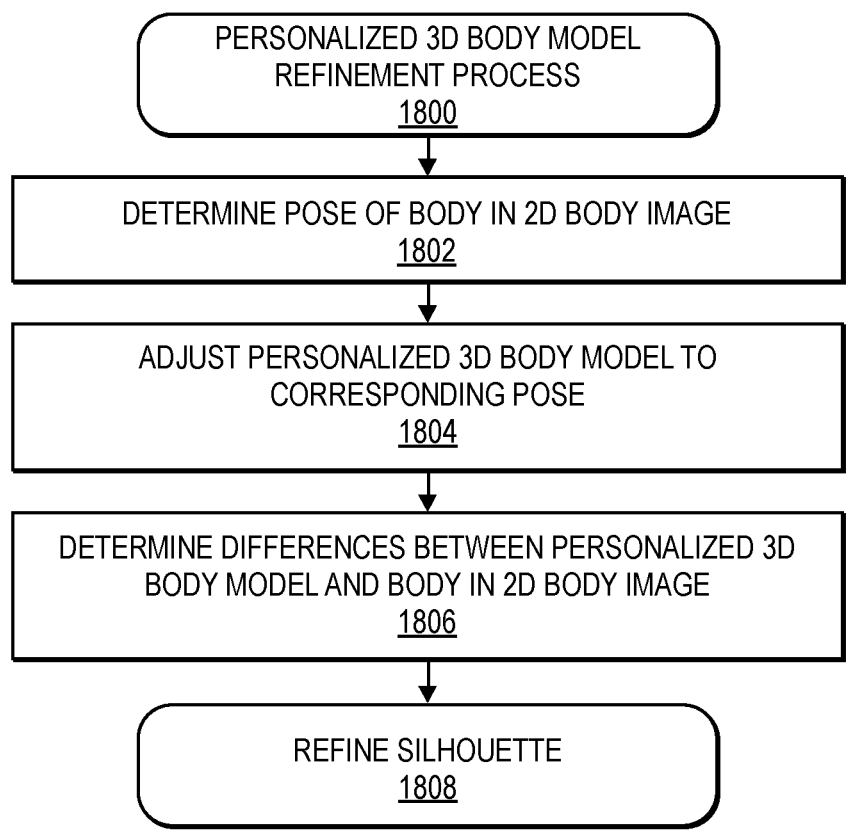
FIG. 18A is an example flow diagram of a three-dimensional body model refinement process, in accordance with implementations of the present disclosure.
Figure 18B:
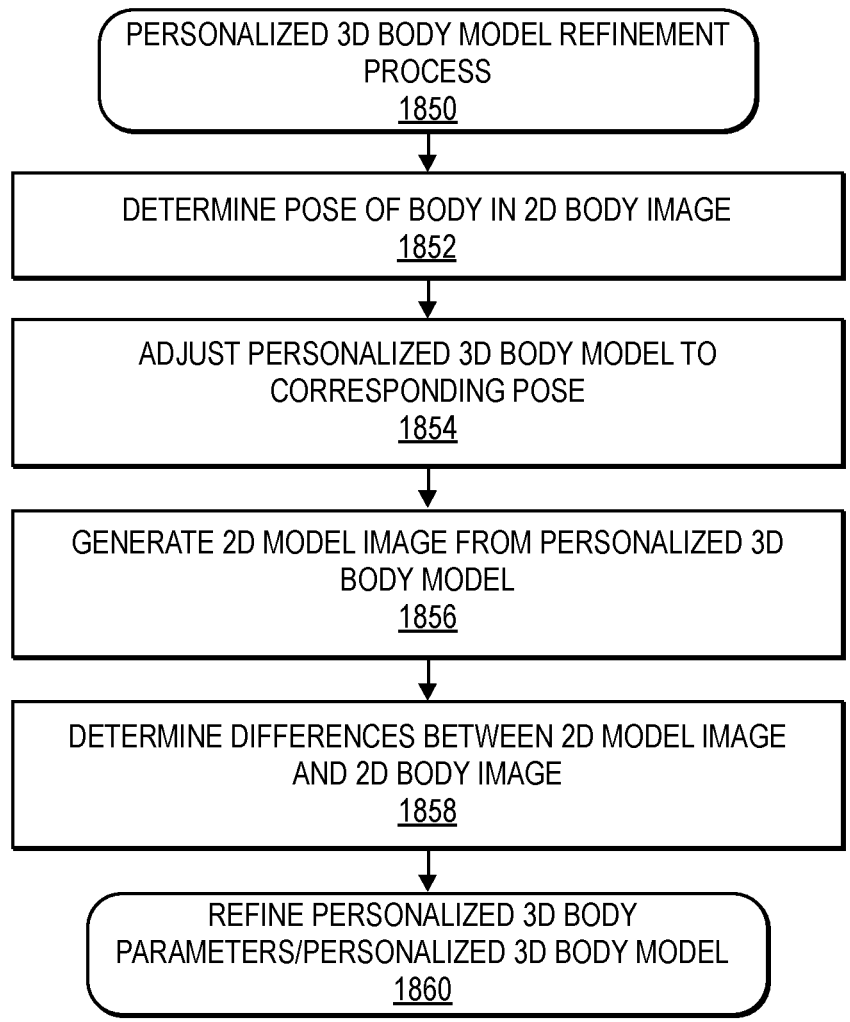
FIG. 18B is another example flow diagram of a three-dimensional body model refinement process, in accordance with implementations of the present disclosure.

After refinement of the silhouette and generation of a personalized 3D body model from refined body parameters, or after receipt of the refined personalized 3D body model from FIG. 18B, one or more textures (e.g., skin tone, hair, clothing, etc.) from the 2D body images may be applied to the personalized 3D body model, as in 1716. Finally, the personalized 3D body model may be provided to the user as representative of the body of the user and/or other personalized 3D body model information (e.g., body mass, joint locations, arm length, body fat percentage, etc.) may be determined from the model, as in 1718.

FIG. 18A is an example flow diagram of a personalized 3D body model refinement process 1800, in accordance with implementations of the present disclosure. The example process 1800 begins by determining a pose of a body represented in one of the 2D body images, as in 1802. A variety of techniques may be used to determine the approximate pose of the body represented in a 2D body image. For example, camera parameters (e.g., camera type, focal length, shutter speed, aperture, etc.) included in the metadata of the 2D body image may be obtained and/or additional camera parameters may be determined and used to estimate the approximate pose of the body represented in the 2D body image. For example, a personalized 3D body model may be used to approximate the pose of the body in the 2D body image and then a position of a virtual camera with respect to that model that would produce the 2D body image of the body may be determined. Based on the determined position of the virtual camera, the height and angle of the camera used to generate the 2D body image may be inferred. In some implementations, the camera tilt may be included in the metadata and/or provided by a portable device that includes the camera. For example, many portable devices include an accelerometer and information from the accelerometer at the time the 2D body image was generated may be provided as the tilt of the camera. Based on the received and/or determined camera parameters, the pose of the body represented in the 2D body image with respect to the camera may be determined, as in 1802.

The personalized 3D body model of the body of the user may then be adjusted to correspond to the determined pose of the body in the 2D body image, as in 1804. With the personalized 3D body model adjusted to approximately the same pose as the user represented in the image, the shape of the personalized 3D body model may be compared to the shape of the body in the 2D body image and/or the silhouette to determine any differences between the personalized 3D body model and the representation of the body in the 2D body image and/or silhouette, as in 1806.

In some implementations, it may be determined whether any determined difference is above a minimum threshold (e.g., 2%). If it is determined that there is a difference between the personalized 3D body model and the body represented in one or more of the 2D body images, the silhouette may be refined. The silhouette may then be used to generate refined body parameters for the body represented in the 2D body images, as discussed above with respect to FIG. 17. If the silhouette is refined, the refined silhouette is returned to the example process 1700, as discussed above and as illustrated in block 1714 (FIG. 17). If no difference is determined or if it is determined that the difference does not exceed a minimum threshold, an indication may be returned to the example process 1700 that there are no differences between the personalized 3D body model and the 2D body image/silhouette.

FIG. 18B is an example flow diagram of another personalized 3D body model refinement process 1850, in accordance with implementations of the present disclosure. The example process 1850 begins by determining a pose of a body represented in one of the 2D body images, as in 1852. A variety of techniques may be used to determine the approximate pose of the body represented in a 2D body image. For example, camera parameters (e.g., camera type, focal length, shutter speed, aperture, etc.) included in the metadata of the 2D body image may be obtained and/or additional camera parameters may be determined and used to estimate the approximate pose of the body represented in the 2D body image. For example, a personalized 3D body model may be used to approximate the pose of the body in the 2D body image and then a position of a virtual camera with respect to that model that would produce the 2D body image of the body may be determined. Based on the determined position of the virtual camera, the height and angle of the camera used to generate the 2D body image may be inferred. In some implementations, the camera tilt may be included in the metadata and/or provided by a portable device that includes the camera. For example, many portable devices include an accelerometer and information from the accelerometer at the time the 2D body image was generated may be provided as the tilt of the camera. Based on the received and/or determined camera parameters, the pose of the body represented in the 2D body image with respect to the camera may be determined, as in 1852.

The personalized 3D body model of the body of the user may then be adjusted to correspond to the determined pose of the body in the 2D body image, as in 1854. With the personalized 3D body model adjusted to approximately the same pose as the user represented in the image, a 2D model image from the personalized 3D body model is generated, as in 1856. The 2D model image may be generated, for example, by converting or imaging the personalized 3D body model into a 2D image with the determined pose, as if a digital 2D image of the personalized 3D body model had been generated. Likewise, the 2D model image may be a binary image with pixels corresponding to the model having a first set of values (e.g., white-RGB values of 255, 255, 255) and pixels that do not represent the model having a second set of values (e.g., black-RGB values of 0, 0, 0)).

The 2D model image is then compared with the 2D body image and/or the silhouette to determine any differences between the 2D model image and the representation of the body in the 2D body image and/or silhouette, as in 1858. For example, the 2D model image may be aligned with the 2D body image and/or the silhouette and pixels between the images compared to determine differences between the pixel values. In implementations in which the pixels are binary (e.g., white or black) an error (e.g., % difference) may be determined as a difference in pixel values between the 2D model image and the 2D body image. That error is differentiable and may be utilized to adjust the body parameters and, as a result, the shape of the personalized 3D body model.

In some implementations, it may be determined whether any determined difference is above a minimum threshold (e.g., 2%). If it is determined that there is a difference between the 2D model image and the body represented in one or more of the 2D body images/silhouette, the personalized 3D body model and/or the body parameters may be refined to correspond to the shape and/or size of body represented in the 2D body image and/or the silhouette, as in 1860. This example process 1850 may continue until there is no difference between the 2D model image and the 2D body image/silhouette, or the difference is below a minimum threshold. As discussed above, the refined personalized 3D body model produced from the example process 1850, or if no refinements are necessary, the personalized 3D body model is returned to example process 1700 at block 1712 and the process 1700 continues.

Figure 19:
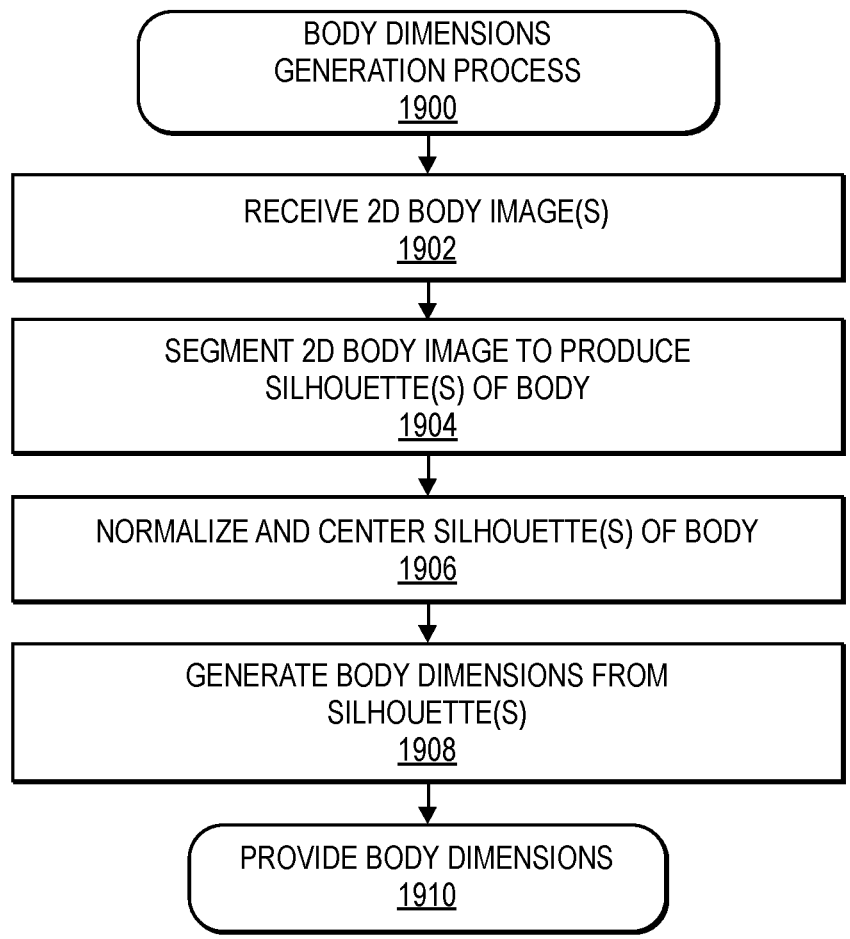
FIG. 19 is an example body dimensions generation process, in accordance with implementations of the present disclosure.

FIG. 19 is an example body dimensions generation processes 1900, in accordance with disclosed implementations.

The example process 1900 begins upon receipt of one or more 2D body images of a body, as in 1902. As noted above, the disclosed implementations are operable with any number of 2D body images for use in generating body dimensions of the body represented in the image. For example, in some implementations, a single 2D body image may be used. In other implementations, two, three, four, or more 2D body images may be used.

As discussed above, the 2D body images may be generated using any 2D imaging element, such as a camera on a portable device, a webcam, etc. The received 2D body images are then segmented to produce a binary silhouette of the body represented in the one or more 2D body images, as in 1904. As discussed above, one or more segmentation techniques, such as background subtraction, semantic segmentation, Canny edge detectors or algorithms, Sobel operators, algorithms or filters, Kayyali operators, Roberts edge detection algorithms, Prewitt operators, Frei-Chen methods, or any other algorithms or techniques that may be known to those of ordinary skill in the pertinent arts. In some implementations, the silhouette may be further segmented into body segments.

In addition, in some implementations, the silhouette(s) may be normalized in height and centered in the image before further processing, as in 1906. For example, the silhouettes may be normalized to a standard height based on a function of a known or provided height of the body of the user represented in the image and an average height (e.g., average height of female body, average height of male body). In some implementations, the average height may be more specific than just gender. For example, the average height may be the average height of a gender and a race corresponding to the body, or a gender and a location (e.g., United States) of the user, etc.

The silhouette(s) of the body represented in the 2D image(s) may then be provided to a trained body dimension model, as discussed above, to generate body dimensions for the body represented in the 2D images, as in 1908. In some implementations, the silhouette(s) may be sent directly to the trained body dimension model for processing. In other implementations, as discussed above, the silhouettes, if there are more than one, may be concatenated and/or further processed to generate personalized body features representative of the body and corresponding silhouette. Those personalized body features may then be provided to the trained body dimension model and the body dimension model may generate body dimensions for the body represented in the 2D image(s) based on the received personalized body features.

Finally, the body dimensions determined by the trained body dimension model may be provided, as in 1910. In some implementations, the determined body dimensions may be included in a presentation along with a generated personalized 3D body model of the body, with other body measurements, etc. In other examples, the body dimensions may be used to group or classify the body into a cohort and/or to provide information regarding the body dimensions determined for the body compared to body dimensions of others in the same cohort, having a similar age, gender, etc.

Some implementations of the systems and methods of the present disclosure may also be provided as a computer-executable program product including a non-transitory machine-readable storage medium having stored thereon instructions (in compressed or uncompressed form) that may be used to program a computer (or other electronic device) to perform processes or methods described herein. The machine-readable storage media of the present disclosure may include, but is not limited to, hard drives, floppy diskettes, optical disks, CD-ROMs, DVDs, ROMs, RAMs, erasable programmable ROMs ("EPROM"), electrically erasable programmable ROMs ("EEPROM"), flash memory, magnetic or optical cards, solid-state memory devices, or other types of media/machine-readable medium that may be suitable for storing electronic instructions. Further, implementations may also be provided as a computer executable program product that includes a transitory machine-readable signal (in compressed or uncompressed form). Examples of machine-readable signals, whether modulated using a carrier or not, may include, but are not limited to, signals that a computer system or machine hosting or running a computer program can be configured to access, or including signals that may be downloaded through the Internet or other networks.

Although the disclosure has been described herein using exemplary techniques, components, and/or processes for implementing the systems and methods of the present disclosure, it should be understood by those skilled in the art that other techniques, components, and/or processes or other combinations and sequences of the techniques, components, and/or processes described herein may be used or performed that achieve the same function(s) and/or result(s) described herein and which are included within the scope of the present disclosure.

Additionally, in accordance with the present disclosure, the training of machine learning tools (e.g., artificial neural networks or other classifiers) and the use of the trained machine learning tools to detect body pose, determine body point locations, determine body direction, to generate personalized 3D body models of a body based on one or more 2D body images of that body, etc., may occur on multiple, distributed computing devices, or on a single computing device, as described herein.

Likewise, while the above discussions focus primarily on a personalized 3D body model of a body being generated from multiple 2D body direction images, in some implementations, the personalized 3D body model may be generated based on a single 2D body direction image of the body. In other implementations, two or more 2D direction body images may be used with the disclosed implementations. Likewise, a single 2D body direction image, such as a front view image, may be used to determine body measurements. In general, the more 2D body direction images, the more accurate the final representation and dimensions of the personalized 3D body model may be.

Still further, while the above implementations are described with respect to generating personalized 3D body models of human bodies represented in 2D body images, in other implementations, non-human bodies, such as dogs, cats, or other animals may be modeled in 3D based on 2D images of those bodies. Accordingly, the use of a human body in the disclosed implementations should not be considered limiting.

It should be understood that, unless otherwise explicitly or implicitly indicated herein, any of the features, characteristics, alternatives or modifications described regarding a particular implementation herein may also be applied, used, or incorporated with any other implementation described herein, and that the drawings and detailed description of the present disclosure are intended to cover all modifications, equivalents and alternatives to the various implementations as defined by the appended claims. Moreover, with respect to the one or more methods or processes of the present disclosure described herein, including but not limited to the flow charts shown in FIGS. 6A through 10, 12A, 12B, and 17 through 19, orders in which such methods or processes are presented are not intended to be construed as any limitation on the claimed inventions, and any number of the method or process steps or boxes described herein can be combined in any order and/or in parallel to implement the methods or processes described herein. Also, the drawings herein are not drawn to scale.

Conditional language, such as, among others, "can," "could," "might," or "may," unless specifically stated otherwise, or otherwise understood within the context as used, is generally intended to convey in a permissive manner that certain implementations could include, or have the potential to include, but do not mandate or require, certain features, elements and/or steps. In a similar manner, terms such as "include," "including" and "includes" are generally intended to mean "including, but not limited to." Thus, such conditional language is not generally intended to imply that features, elements and/or steps are in any way required for one or more implementations or that one or more implementations necessarily include logic for deciding, with or without user input or prompting, whether these features, elements and/or steps are included or are to be performed in any particular implementation.

The elements of a method, process, or algorithm described in connection with the implementations disclosed herein can be embodied directly in hardware, in a software module stored in one or more memory devices and executed by one or more processors, or in a combination of the two. A software module can reside in RAM, flash memory, ROM, EPROM, EEPROM, registers, a hard disk, a removable disk, a CD-ROM, a DVD-ROM or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC. The ASIC can reside in a user terminal. In the alternative, the processor and the storage medium can reside as discrete components in a user terminal.

Disjunctive language such as the phrase "at least one of X, Y, or Z," or "at least one of X, Y and Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain implementations require at least one of X, at least one of Y, or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

Language of degree used herein, such as the terms "about," "approximately," "generally," "nearly" or "substantially" as used herein, represent a value, amount, or characteristic close to the stated value, amount, or characteristic that still performs a desired function or achieves a desired result. For example, the terms "about," "approximately," "generally," "nearly" or "substantially" may refer to an amount that is within less than 10% of, within less than 5% of, within less than 1% of, within less than 0.1% of, and within less than 0.01% of the stated amount.

Although the invention has been described and illustrated with respect to illustrative implementations thereof, the foregoing and various other additions and omissions may be made therein and thereto without departing from the spirit and scope of the present disclosure.

What is claimed is:

1. A computer-implemented method, comprising:
receiving, at a remote computing resource and from an application executing on a device, at least one two-dimensional ("2D") body image of a user that includes a representation of at least a portion of a body of the user;
processing, at the remote computing resource, the at least one 2D body image to determine a current body composition of the body of the user, the current body composition indicating at least a current body fat measurement value of the body;
determining a goal body composition for the body, the goal body composition indicating a least a goal body fat measurement value for the body;
determining, at the remote computing resource and based at least in part on the current body composition, a cohort that includes a plurality of data indicative of other bodies who progressed from a starting body composition that is similar to the current body composition to a final body composition that is similar to the goal body composition;
determining, at the remote computing resource and based at least in part on the plurality of data, a trend line between the current body composition and the goal body composition, the trend line indicating a trend in a rate of change of body fat measurement values among the plurality of data between the current body composition and the goal body composition;
determining, at the remote computing resource and based at least in part on the cohort and the trend line, a body change journey duration indicating a duration of time for the body of the user to progress from the current body composition to the goal body composition along the trend line;
sending to the application executing on the device, information indicative of the body change journey duration and the trend line; and
presenting, on a display of the device, at least the body change journey duration and the trend line to the user as illustrative of a body change journey.

2. The computer-implemented method of claim 1, further comprising:
generating, based at least in part on the current body composition, a goal personalized three-dimensional body model of the body, the goal personalized three-dimensional body model representative of a predicted appearance of the body at the goal body fat measurement value and with the goal body composition.

3. The computer-implemented method of claim 1, wherein generating the body change journey includes adjusting the trend line to begin at the current body composition.

4. The computer-implemented method of claim 1, wherein the trend line is a median trend line indicative of a median change in visual body fat values among the plurality of data.

5. The computer-implemented method of claim 4, further comprising:
monitoring a progress of the body as the body progresses through the body change journey, wherein the monitoring includes at least:
determining one or more body measurement values at a point in time during the body change journey duration; and
presenting the one or more body measurement values on the trend line at the point in time.

6. A computing system, comprising:
one or more processors; and
a memory storing program instructions that, when executed by the one or more processors, cause the one or more processors to at least:
determine a goal body measurement value for a body measurement of a body of a user;
receive, from a second computing system that is separate from the computing system, a two-dimensional ("2D") body image that includes a representation of at least a portion of the body of the user;
process at least a portion of the 2D body image to determine a current body measurement value for the body measurement of the body;
determine, based at least in part on the current body measurement value, a cohort that includes a plurality of data indicative of other bodies who progressed from a starting body measurement value that is similar to the current body measurement value;
generate, based at least in part on the cohort and the plurality of data, a trend line indicative of a rate of change in the body measurement as determined from the plurality of data;
generate, based at least in part on the trend line, the current body measurement value and the goal body measurement value, a body change journey that the user can follow to progress from the current body measurement value to the goal body measurement value; and
send, to an application executing on the second computing system, information indicative of the body change journey such that the application executing on the second computing system can present, on a display of the second computing system, at least a portion of the body change journey.

7. The computing system of claim 6, wherein the body change journey includes at least:
a distribution indicating an expected change in the body measurement of the body during the body change journey; and
a duration of the body change journey.

8. The computing system of claim 6, wherein the trend line is indicative of a median trend of a change in the body measurement experienced by the other bodies between a first point in time and a second point in time.

9. The computing system of claim 6, wherein the cohort is determined based at least in part on one or more of:
the current body measurement value, an age of the body, a demographic of the user, a gender of the body, a weight of the body, a height of the body, a medical history of the body, an average sleep duration of the body, an activity level of the body, an exercise level of the body, a body composition of the body, a current activity level of the body, a known health issue of the body, a muscle mass of the body, a fat free mass of the body, or a waist-to-hip ratio of the body.

10. The computing system of claim 6, wherein the goal body measurement value is at least one of a weight of the body, a body fat measurement value of the body, a lean body mass of the body, a muscle mass of the body, a fat free mass of the body, a waist-to-hip ratio of the body, or a body mass index of the body.

11. The computing system of claim 6, wherein the program instructions that, when executed by the one or more processors, further cause the one or more processors to at least:
generate a current personalized 3D body model of the body based at least in part on a current body composition of the body; and
generate a goal personalized 3D body model of the body based at least in part on a goal body composition of the body; and
wherein the current personalized 3D body model is different than the goal personalized 3D body model.

12. The computing system of claim 6, wherein the program instructions that, when executed by the one or more processors, further cause the one or more processors to at least:
determine a predicted body measurement value for the body measurement at a point in time during the body change journey;
obtain an actual body measurement value of the body measurement at the point in time;
determine a difference between the predicted body measurement value and the actual body measurement value; and
adjust, based at least in part on the difference, the body change journey.

13. The computing system of claim 12, wherein the program instructions that, when executed by the one or more processors to adjust the body change journey, further cause the one or more processors to at least:
adjust the trend line of the body change journey or adjust a duration of the body change journey.

14. The computing system of claim 6, wherein the program instructions that, when executed by the one or more processors, further cause the one or more processors to at least:
determine one or more ranges above or below the trend line of the body change journey, the one or more ranges indicative of changes experienced by a percentage of the other bodies of the cohort;
determine an intervention corresponding to at least some of the percentage of bodies of the cohort; and
present at least one of the one or more ranges and an indication of the intervention.

15. The computing system of claim 6, wherein the program instructions that, when executed by the one or more processors, further cause the one or more processors to at least:
determine, during a duration of the body change journey, an actual progress of the body;

determine, based at least in part on a comparison of the actual progress of the body with a predicted progress of the body, that the body is not progressing as predicted; and in response to determination that the body is not progressing as predicted, change at least one of a trend line of the body change journey or the duration of the body change journey.

16. A method, comprising:

receiving, at a first computing device and from a second computing device that is separate from the first computing device, a two-dimensional ("2D") body image of a user that includes a representation of at least a portion of a body of the user;

determining, at the first computing device and based at least in part on the 2D body image, a current body composition of a body, the current body composition indicating at least one current body measurement value of the body;

determining a goal body measurement value that is different than the at least one current body measurement value;

determining, at the first computing device, a cohort for the body, wherein the cohort includes a plurality of data indicative of other bodies that progressed from a starting body composition that is similar to the current body composition;

generating, at the first computing device and based at least in part on the current body composition and the cohort, a body change journey to be followed to change the at least one current body measurement value of the body to the goal body measurement value, the body change journey having a time duration;

determining, at the first computing device and based at least in part on the plurality of data of the cohort:
a trend line indicative of an expected change in at least one body measurement between the current body measurement value and the goal body measurement value during the time duration of the body change journey; and a range above the trend line indicative of a range of changes in the at least one body measurement value that is above the trend line and between the current body measurement value and the goal body measurement value during the time duration of the body change journey; and sending to the second computing device, information indicative of the body change journey, the trend line and the range above the trend line such that the second computing device can present the trend line, the range above the trend line, and the information indicative of the body change journey.

17. The method of claim 16, wherein the body change journey indicates at least one of an intensity of the body change journey or a likelihood of success in completing the body change journey.

18. The method of claim 16, further comprising:

receiving, during the body change journey, an actual body measurement value of the body;

adjusting, based at least in part on the actual body measurement value, the trend line for a remainder of the body change journey to produce an adjusted trend line; and presenting the adjusted trend line.

19. The method of claim 16, further comprising:

determining at least one intervention that, if implemented during the body change journey, is predicted to alter a progress of the body toward the goal body measurement value; and presenting an indication of the intervention.

20. The method of claim 19, wherein the intervention is determined based at least in part on at least a portion of the plurality of data of the cohort.

* * * * *